US011553161B2

(12) United States Patent
Greco et al.

(10) Patent No.: US 11,553,161 B2
(45) Date of Patent: Jan. 10, 2023

(54) ELECTRONIC PATIENT SITTER MANAGEMENT SYSTEM AND METHOD FOR IMPLEMENTING

(71) Applicant: CareView Communications, Inc., Lewisville, TX (US)

(72) Inventors: Sam Anthony Greco, Flower Mound, TX (US); Steven Gail Johnson, Highland Village, TX (US); Matthew Cameron Clark, Frisco, TX (US); Derek Stevan del Carpio, Corinth, TX (US)

(73) Assignee: Care View Communications, Inc., Lewisville, TX (US)

( * ) Notice: Subject to any disclaimer, the term of this patent is extended or adjusted under 35 U.S.C. 154(b) by 0 days.

(21) Appl. No.: 17/335,137

(22) Filed: Jun. 1, 2021

(65) Prior Publication Data

US 2021/0289172 A1    Sep. 16, 2021

Related U.S. Application Data

(63) Continuation of application No. 16/787,840, filed on Feb. 11, 2020, now Pat. No. 11,057,589, which is a (Continued)

(51) Int. Cl.
*H04N 7/18* (2006.01)
*G16Z 99/00* (2019.01)
(Continued)

(52) U.S. Cl.
CPC ......... *H04N 7/181* (2013.01); *G08B 21/0227* (2013.01); *G16H 30/20* (2018.01);
(Continued)

(58) Field of Classification Search
CPC .......................... G06F 19/3418; G06F 19/327
See application file for complete search history.

(56) References Cited

U.S. PATENT DOCUMENTS

| 2007/0136102 A1* | 6/2007 | Rodgers | ................. | G06Q 10/10 |
| | | | | 705/3 |
| 2007/0194939 A1* | 8/2007 | Alvarez | ................. | A61B 5/411 |
| | | | | 348/E7.086 |

(Continued)

*Primary Examiner* — Jerry T Jean Baptiste
(74) *Attorney, Agent, or Firm* — Meister Seelig & Fein LLP

(57) ABSTRACT

An electronic sitter management system coupled to patient surveillance network having a plurality of video cameras, each camera transmitting a stream of surveillance video of a respective patient room. The sitter management system includes at least one sitter management device and a plurality of sitter devices. Each device being assigned a plurality of patient rooms and capable of receiving a plurality of streams of surveillance video for the corresponding plurality of patient rooms and simultaneously displaying a plurality of video images of the corresponding plurality of patient rooms. Each device is also capable of transmitting sitter device availability information to the sitter management device. The sitter management device being capable of recognizing a sitter device being unavailable and reassigning the plurality of patient rooms previously assigned to the unavailable device to other of the plurality of sitter devices that are available.

20 Claims, 36 Drawing Sheets

Enhanced Sitter Patient Screen with Zoom in (Landscape)

Related U.S. Application Data continuation of application No. 16/027,480, filed on Jul. 5, 2018, now Pat. No. 10,630,941, which is a continuation of application No. 15/707,192, filed on Sep. 18, 2017, now Pat. No. 10,044,989, which is a continuation of application No. 13/714,587, filed on Dec. 14, 2012, now Pat. No. 9,794,523.

(60) Provisional application No. 61/709,129, filed on Oct. 2, 2012, provisional application No. 61/577,634, filed on Dec. 19, 2011.

(51) Int. Cl.
  *G08B 21/02* (2006.01)
  *G16H 40/67* (2018.01)
  *G16H 30/20* (2018.01)
  *G16H 40/20* (2018.01)

(52) U.S. Cl.
  CPC ............. *G16H 40/67* (2018.01); *G16Z 99/00* (2019.02); *G16H 40/20* (2018.01)

(56) References Cited

U.S. PATENT DOCUMENTS

| | | | | |
|---|---|---|---|---|
| 2010/0134609 A1* | 6/2010 | Johnson | ................. | G16H 10/60 |
| | | | | 348/77 |
| 2011/0242317 A1* | 10/2011 | Wengrovitz | ........... | H04N 7/181 |
| | | | | 348/E7.091 |
| 2011/0306926 A1* | 12/2011 | Woo | ....................... | G06Q 10/10 |
| | | | | 345/173 |

* cited by examiner

Sitter Management Network

INITIAL SITTER MONITORING MODE GROUPS

EQUAL DISTRIBUTION WITH BLUEPRINT-TYPE ROLLOVER POLICY INVOKED

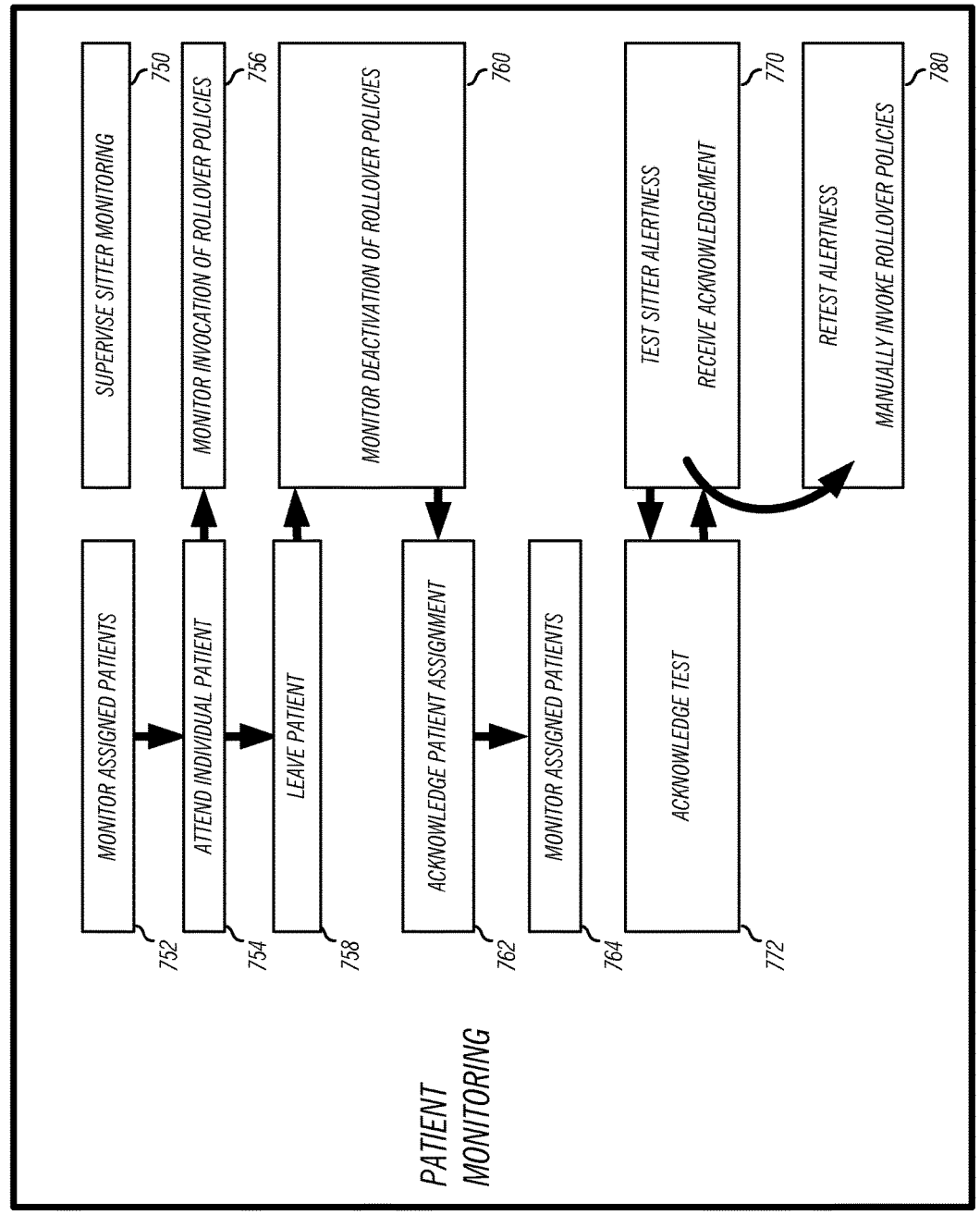

SITTER DISTRIBUTION AND PATIENT ASSIGNMENT

SITTER DISTRIBUTION AND PATIENT ASSIGNMENT

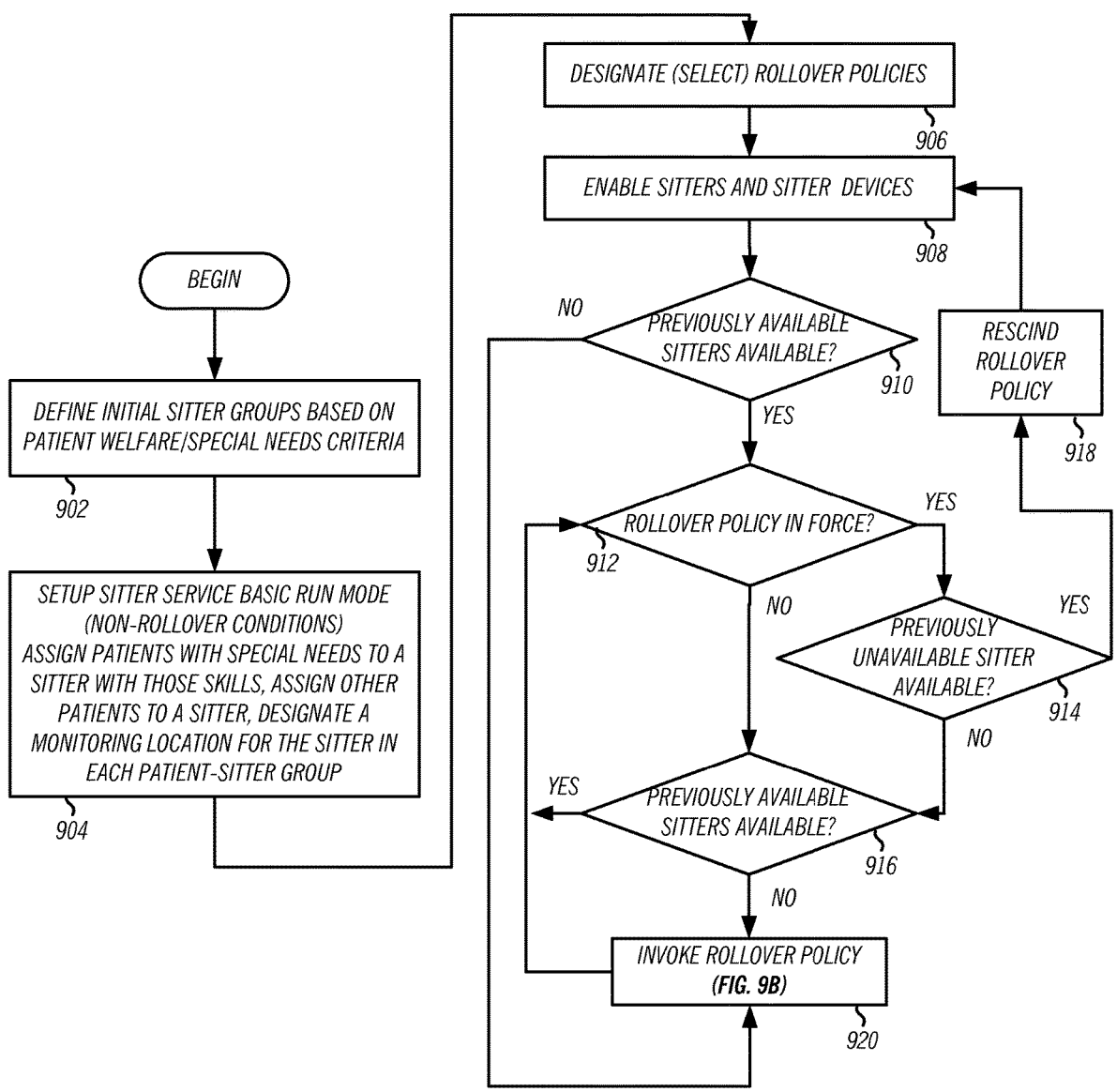

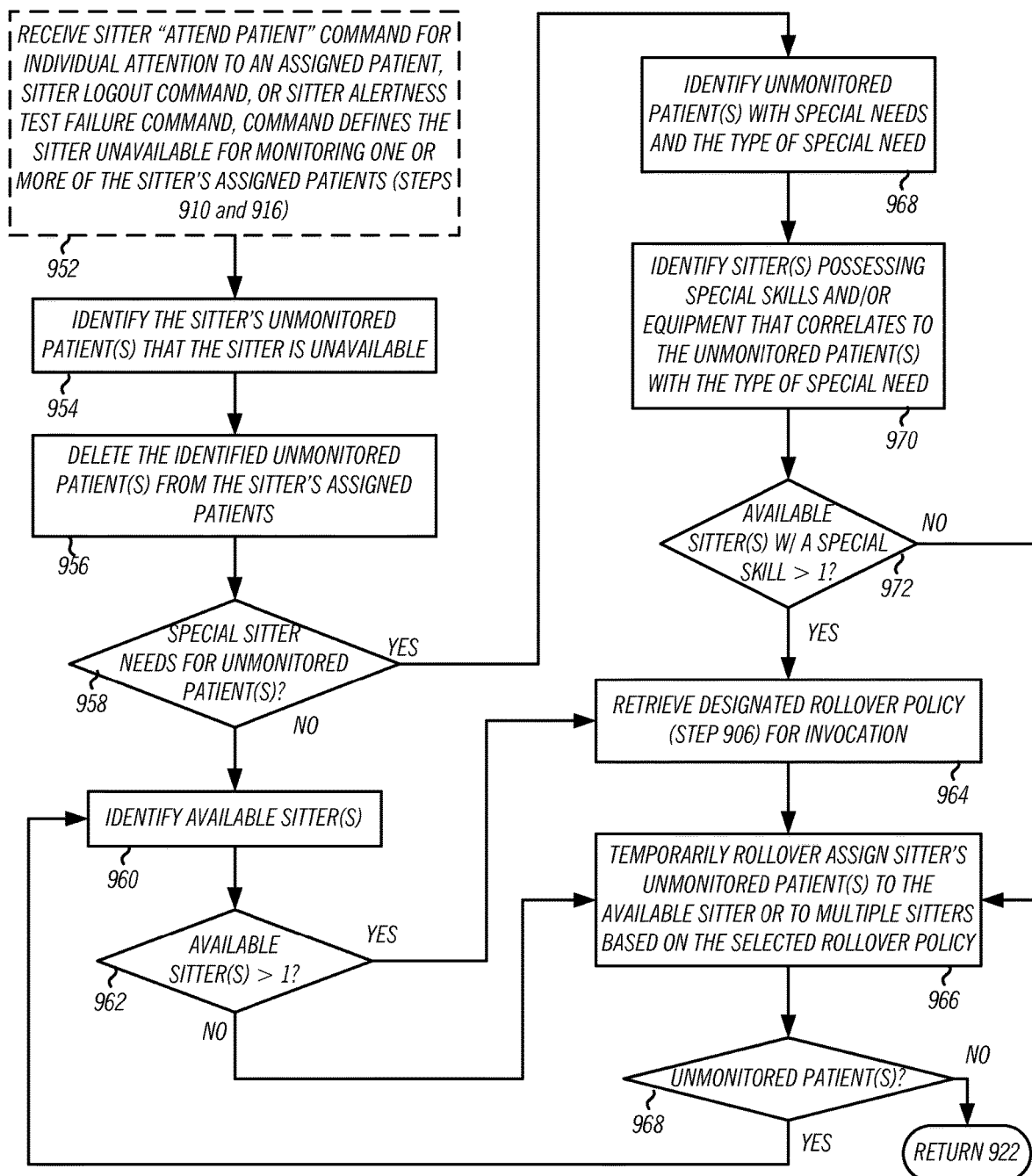

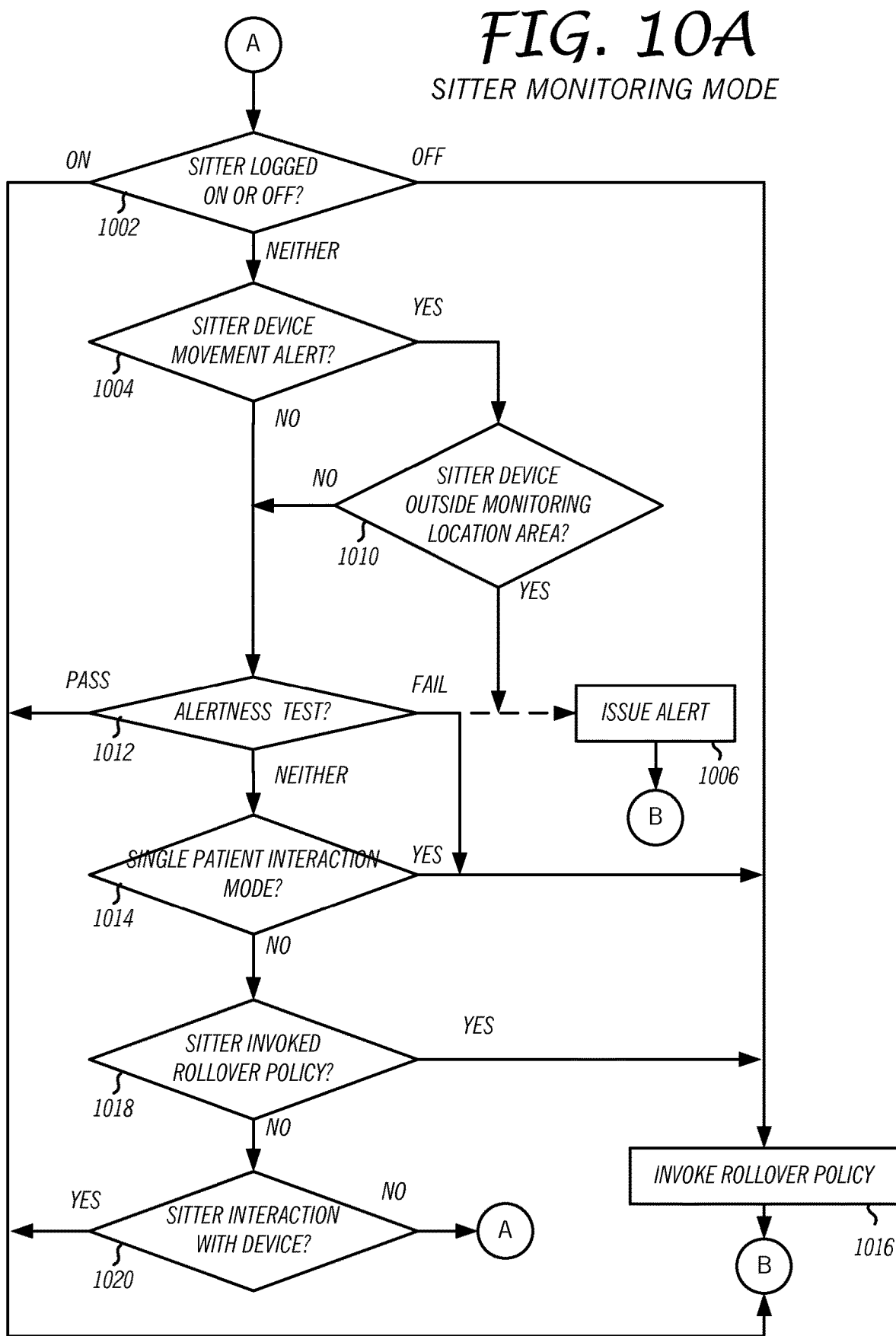

SITTER MONITORING MODE

Administrator Assignment Screen (Landscape)

Administrator Assignment Screen Showing Patient Assignments for Sitter One (Landscape)

Administrator Assignment Screen Showing Patient Assignments for Sitter Two (Landscape)

Administrator Monitor Mode Screen Showing Sitter Activity (Landscape)

Sitter Login Screen (Landscape)

Sitter ID/Password Login Screen (Landscape)

Sitter Registration Login Screen (Landscape)

Sitter Login Verification Screen (Waiting Assignment)
(Landscape)

Sitter Main Screen (Post Assignment) (Landscape)

Sitter Monitoring Screen (Portrait)

Sitter Monitoring Screen (Landscape)

Enhanced Sitter Patient Management Screen (Portrait)

Enhanced Sitter Patient Management Screen (Landscape)

Enhanced Sitter Patient Screen with Zoom In (Landscape)

Enhanced Sitter Patient Screen with Zoom In showing Virtual Bed Rails (Landscape)

Sitter Main Screen with Virtual Bed Rails (Landscape)

Sitter Patient Attend Screen with Assignment (Landscape)

Sitter Patient Attend Screen (Landscape)

Sitter Main Screen Showing Rollover Patient from RollOver Sitter (Landscape)

Sitter Main Screen Showing Patient Motion Alarm (Landscape)

Sitter Main Screen Showing Virtual Bed Rail Alarm (Landscape)

Sitter Main Screen Showing Sitter Response to Alertness Test (Landscape)

ELECTRONIC PATIENT SITTER MANAGEMENT SYSTEM AND METHOD FOR IMPLEMENTING

The present application is related to and claims priority from the following copending U.S. patent applications: U.S. Provisional Patent Application No. 61/577,634, entitled Electronic Patient Sitter Management System and Method for Implementing and U.S. Provisional Patent Application No. 61/709,129, entitled Electronic Patient Sitter Management System and Method for Implementing filed Oct. 2, 2012, which are assigned to the assignee of the present invention. The above identified applications are incorporated by reference herein in their entirety.

BACKGROUND OF THE INVENTION

The present invention relates generally to monitoring patient surveillance video using a sitter's patient monitoring device. More particularly, the present invention relates to an electronic patient sitter management system, and method and software program product for managing a plurality of sitter's patient monitoring devices for monitoring real time surveillance patient room video based on the availability of the sitter's patient monitoring devices to the electronic patient sitter management system.

At times, patients and/or residents in a heath care facility (HCF), which may be a hospital, convalescent facility, nursing home, long term care facility, a rehabilitation facility, or the like, will need managed assistance that does not rise to the level of that typically offered by a HCF professional, i.e., a doctor, counselor, nurse, or even a nurse aide, however, the patient must be continuously monitored for conditions that might indicate the immediate need for intervention by a HCF professional. Such situations include, but are not limited to, patient's that are in a demented, depressed, impaired or incapacitated mental state in which the patient can not be trusted to make cognitive decisions concerning her own welfare, best interest or safety. Examples include, patients under sedation or other medications that reduce the cognitive abilities or patient's motor skills, or under or recovering from any medical procedure or diagnostic procedure utilizing such medications, patients recovering from surgery, a general anesthesia (or some local anesthetics that might impair the patient's mental capacity or motor skills), suicidal or deeply depressed patients, patients in the initial or critical stages of substance abuse treatment where sobriety must be independently verified and other similar situations.

In the prior art, these types of patients were handled in one of two ways: remote monitoring of patients at a predesigned HCF station, such as a nurse station, by HCF professionals on duty at that station and by a sitter stationed with the patient, typically in the same room as the patient (a local sitter).

Monitoring patients by HCF professionals on duty at a predesigned HCF station is described in U.S. Pat. No. 7,477,285 to Johnson, entitled Non-Intrusive Data Transmission Network for Use in an Enterprise Facility and Method for Implementing, which is assigned to the assignee of the present invention, and to a lesser extent each of U.S. patent applications: Ser. No. 12/589,654 entitled System and Method for Predicting Patient Falls, Ser. No. 12/589,654 System and Method for Documenting Patient Procedures, Ser. No. 12/804,774 entitled System and Method for Using a Video Monitoring System to Prevent and Manage Decubitus Ulcers in Patients and Ser. No. 61/513,523 entitled Noise Correcting Patient Fall Risk State System and Method for Predicting Patient Falls, each assigned to the assignee of the present invention and all of which are incorporated herein by reference in their entireties. These patient monitoring systems involve implementing a patient surveillance system in which a surveillance video camera is strategically positioned in patients' rooms and which is connected to a surveillance network. The surveillance network is further connected to a nurse monitoring device located at the predesigned HCF station. FIG. 1 illustrates a view from image 100 of such a monitoring device. Notice surveillance image 100 shows the real time surveillance video images a plurality of patient rooms, typically all of the patient rooms under the charge of that particular HCF station. Surveillance image 100 shows patient rooms 300 through 318 under the charge of the HCF professionals assigned to that particular HCF station. Optimally, the nurse monitoring device will allow HCF professionals to repopulate, reorganize and resize the individual video frames corresponding to the respective patient rooms. In so doing, image frames corresponding to patients requiring more attention, such as those designated for sitter services, can be situated to more prominent positions within surveillance image 100, such as to the upper image frame rows, enlarged, enhanced or otherwise visually designated as being selected for special sitter service from the attending HCF professionals at the particular HCF station.

While monitoring patients by HCF professionals on duty at a predesigned HCF station has certain advantages to other patient monitoring strategies (i.e., the local sitter option), it is extremely expensive for the HCF to devote one or more skilled HCF professionals to mundane sitter duties. Moreover, because the intent of sitter services is to provide uninterrupted monitoring to patients in need of that service, having charge skilled HCF professionals such as nurses performing sitter services is problematic because in critical situations these professional often leave their monitoring duties. For instance, the HCF professionals on duty may be required to perform more immediate tasks involving other patients, such as personally attending to patients in their respective patient rooms, thereby leaving other sitter patients unmonitored, sometimes for extended periods of time. Additionally, even though the predesigned HCF stations are centrally located to the patients' rooms under the care of that station, HCF professionals may be required to traverse long distances or through multiple facility corridors in order to reach a sitter patient needing assistance. Finally, another problem with using a skilled HCF professional for sitter responsibilities is that of attention to the monitor. Monitoring surveillance video can be extremely monotonous. Skilled HCF professionals often feel underutilized in sitter monitoring roles and become complacent, and often attempt to multitask to their other duties at the expense of the sitter patients.

Consequently, even though patient monitoring systems of the type discussed in the aforementioned specifications are important advancements in patient care and safety, they are generally not preferred over the use of local sitters, for the reasons given above. Most HCFs have reverted to designated patient-sitter arrangements, such as the local sitter option.

Here it should be mentioned that typically, a sitter of the type utilized in the local sitter option, has three primary functions: monitor patient under the sitter's care for any action that might indicate a sitter response is needed; respond to the patient; and alert a skilled HCF professional if the sitter response is inadequate or if the patient action reflects a need for intervention by a skilled HCF professional. Typically, the maximum response authorized by a sitter to a patient is to verbally reassure the patient of her surroundings, or to warn the patient that her actions may be dangerous, harmful or otherwise contrary to the patient orders. If any other response is necessary, the sitter must immediately alert a skilled HCF professional, typically by calling a nurse to the patient's room. Hence, it is the sitter's responsibility to take a position in the patient room, visually monitor that patient and, using the "nurse call button" or similar device, alert a skilled HCF professional if the patient situation dictates. In so doing, the HCF can assign sitter duties to relatively unskilled personnel and not the more skilled and rigorously trained skilled HCF professional staff. Hence, although the overall cost of sitting service to the HCF may not decrease appreciably, at least the skilled HCF professional is freed from sitter responsibilities to do more important work, and, patients needing sitting services are monitoring continuously, irrespective of the workload of the skilled HCF professional staff. Other shortcomings of the local sitter option are that the flex-sitter must be available to take shifts with relatively short notice since the sitter workload for a HCF may vary widely from one shift to the next and, additionally, floating sitters must be available to relieve local sitters for breaks, personal time and lunch.

Here again, the cost to the HCF of sitter service can be astronomical. What is needed is a sitter management system which enables a more cost effective approach to sitter care of patients, while not sacrificing or even increasing the standard of care to the patients.

BRIEF SUMMARY OF THE INVENTION

The present invention is directed to an electronic sitter management system coupled to patient surveillance network having a plurality of video cameras, each camera transmitting a stream of surveillance video of a respective patient room system, and method and software product for implementing. The sitter management system includes at least one sitter management device and a plurality of sitter monitoring devices. Each sitter monitoring device being assigned a plurality of patient rooms and capable of receiving a plurality of streams of surveillance video for the corresponding plurality of patient rooms and simultaneously displaying a plurality of video images of the corresponding plurality of patient rooms. Each device is also capable of transmitting sitter device availability information to the sitter management device. The sitter management device being capable of recognizing a sitter device being unavailable and reassigning the plurality of patient rooms previously assigned to the unavailable device to other of the plurality of sitter devices that are available.

The sitter management device initially assigns each of the patient room surveillance videos to display on specific sitter monitoring devices. Whenever a sitter monitoring device becomes unavailable to display patient room surveillance videos, such as when the sitter is interacting with a single patient, the unmonitored patient room surveillance videos are rolled over to other sitter monitoring devices that are available to receive video. Several rollover methods for distributing the unmonitored patient room surveillance videos can be employed: Blast is where the unmonitored patient room surveillance videos are reassigned to all other sitters that are currently available; Round robin distribution is where the unmonitored patient room surveillance videos are reassigned to other sitters based on the next available sitter on a utilization list; Equal distribution is where the unmonitored patient room surveillance videos are reassigned to other sitters based on equalizing sitter loading; Blueprint is where the unmonitored patient room surveillance videos are reassigned to other sitters within a specific range based on the hospital blueprint; Wi-Fi proximity is where the unmonitored patient room surveillance videos are reassigned to other sitters within a specific range based on what wireless access point their device is connected to; GPS is where the unmonitored patient room surveillance videos are reassigned to other sitters based on proximity using the device's GPS; and No rollover is where the unmonitored patient room surveillance videos are not reassigned to other sitters.

From time to time, sitter monitor devices receive alertness tests for checking the attentiveness of the sitter. If the sitter responds promptly to the test, the test is merely logged. If the sitter does not respond, then the electronic sitter management system takes action to protect the patients being monitored by the sitter. Initially, the electronic sitter management system may issue and alert to the sitter's manager and to the sitter, reminding the sitter. Alternatively, the electronic sitter management system may consider the sitter monitor device to be unavailable and invoke the rollover policies. In that case, the sitter monitor device is unauthorized and the patients being monitored are reassigned to other sitters using one of the rollover methods.

Additionally, the sitter monitoring device logs all important events or interactions by the sitter. Typically, the events are merely written to a log that is viewable by the sitter's manager at the sitter management device. However, in certain cases, sitter events, corresponding data and patient surveillance video may be flagged for recordation in the patient's medical records. This data may include notes and comments entered on the sitter monitoring device by the sitter.

An electronic sitter management system coupled to patient surveillance network, the patient surveillance network comprising a plurality of video cameras for transmitting a stream of patient surveillance video for each of the respective patient rooms, each of the plurality of video cameras located in a patient room and aimed at an interior of the respective patient room. The electronic sitter management system comprising a plurality of sitter monitor devices, and each sitter monitor device comprising a video display for displaying at least one stream of patient surveillance video transmitted from one of the plurality of video cameras located in the patient room, a sitter interface object for receiving a sitter interaction and for generating a sitter interaction signal, a device availability information generator for receiving the sitter interaction signal and generating one of availability information for designating the sitter monitor device as being available to receive the at least one stream of patient surveillance video and unavailability information for designating the sitter monitor device as being unavailable to receive the at least one stream of patient surveillance video and a network connection for receiving the at least one stream of patient surveillance video transmitted from one of the plurality of video cameras located in the patient room and for transmitting the one of availability information and unavailability information.

The electronic sitter management system also comprising a sitter management device comprising a patient assignment component for assigning a first stream of patient surveillance video for a first patient room for display on a first sitter monitor device of the plurality of sitter monitor devices, and for assigning a second stream of patient surveillance video for a second patient room for display on a second sitter monitor device of the plurality of sitter monitor devices, and for assigning a third stream of patient surveillance video for a third patient room for display on a third sitter monitor device of the plurality of sitter monitor devices, and a rollover patient assignment component for receiving first unavailability information for designating the first sitter monitor device as being unavailable to receive the first stream of patient surveillance video for the first patient room for display on the first sitter monitor device and for rollover assigning the first stream of patient surveillance video from the first sitter monitor device.

The rollover patient assignment component of the electronic sitter management system for rollover assigning the first stream of patient surveillance video from the first sitter monitor device to the second sitter monitor device, wherein the second video display of the second sitter monitor device simultaneously displays the second stream of patient surveillance video for the second patient room and the first stream of patient surveillance video for the first patient room.

The rollover patient assignment component of the electronic sitter management system for assigning the first stream of patient surveillance video from the second sitter monitor device to the first sitter monitor device, wherein the second video display of the second sitter monitor device displays the second stream of patient surveillance video for the second patient room and the first video display of the first sitter monitor device displays the first stream of patient surveillance video for the first patient room.

BRIEF DESCRIPTION OF THE SEVERAL VIEWS OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIGS. 7A and 7B are a flowchart depicting the high level method for implementing the electronic patient sitter management service in accordance with an exemplary embodiment of the present invention;

FIGS. 9A and 9B illustrate a flowchart for a process directed to establishing a sitter rollover assignment policy and invoking those rollover policies in accordance with an exemplary embodiment of the present invention;

FIGS. 10A and 10B depict a flowchart of method performed by the electronic patient sitter management system for logging events and issuing alerts and rollover policy in accordance with exemplary embodiments of the present invention;

Figure 1:
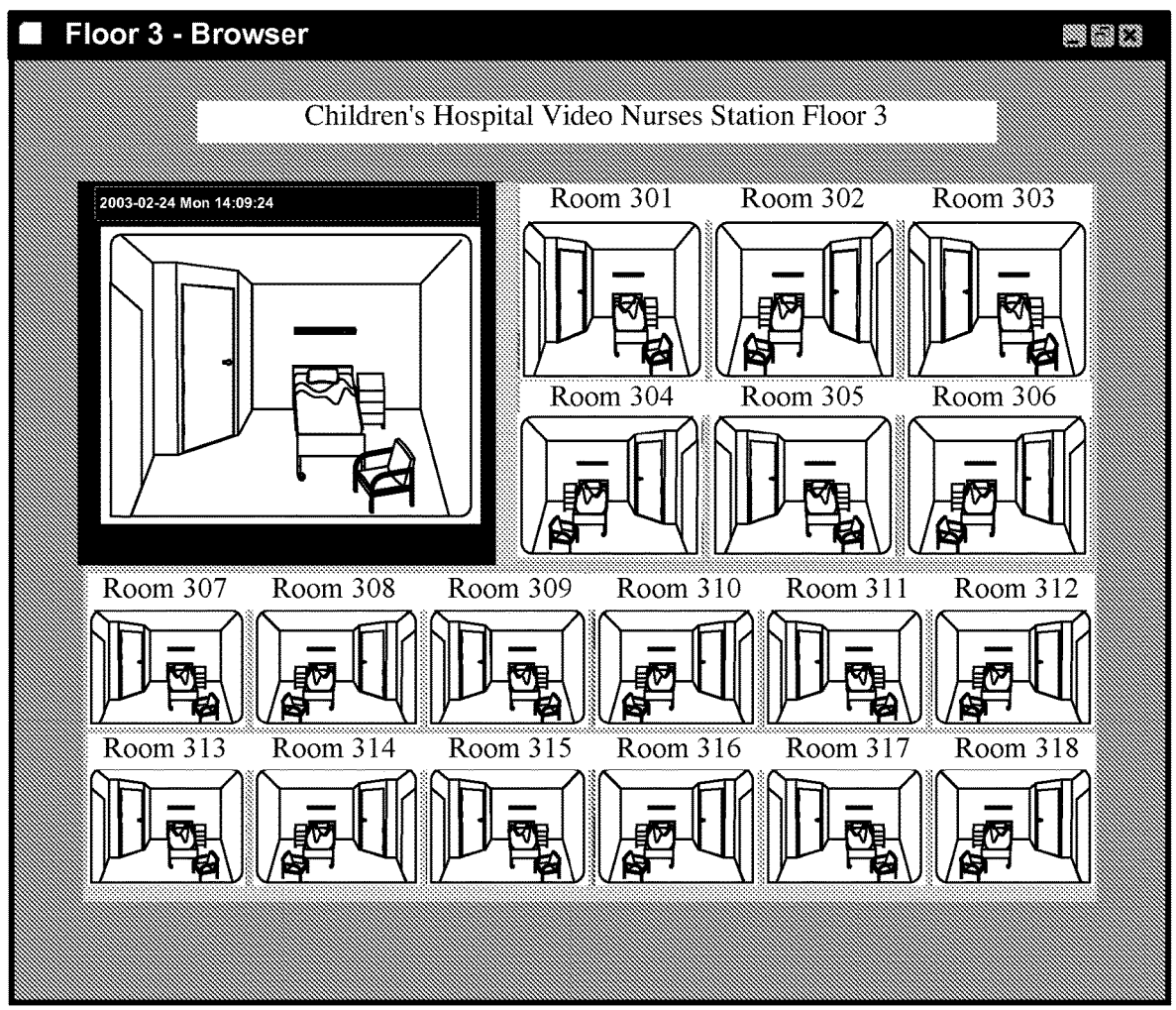
FIG. 1 illustrates a view from a monitoring device positioned at a nurse station as is known in the prior art.

Other features of the present invention will be apparent from the accompanying drawings and from the following detailed description.

DETAILED DESCRIPTION OF THE INVENTION

Element Reference Number Designations

| | |
|---|---|
| 200: Patient surveillance system | 415: Secondary nonvolatile memory |
| 202: Patient room video surveillance cameras/set top boxes | 417: Television/Monitor |
| | 418: Medical procedure remote interface |
| 204: Medical records | 422: Medical procedure interface |
| 206: Entertainment services | 424: Patient vital signs monitoring device |
| 208: System administration | 426: Pillow speaker interface |
| 210: Data transmission network | 450: HCF professional station (nurse station) |
| 212: HCF professional stations | 460: HCF surveillance/monitor device (nurse surveillance/monitor device) |
| 216: Patient monitoring | 470: Patient monitoring sub-system |
| 218: Security | 461: Processor unit |
| 220: Internet services | 462: Network controller |
| 222: Motion sensing | 463: Video processor controller |
| 224: Virtual Bed Rails Service | 464: Primary nonvolatile |
| 300: Patient surveillance system | 465: Secondary nonvolatile memory |
| 302: Touch screen | 467: Monitor/Touch screen |
| 304: webcam | 468: Audio |
| 352: Patient sitter services | 469: Manual interface device |
| 353: Sitter app | 500: HCF |
| 354: Sitter manager app | 506: ICU |
| 355: Sitter management software | 508: Corridor |
| 356: Wireless access point | 561: Group 1 sitter device |
| 360: Sitter device | 562: Group 2 sitter device |
| 361: Sitter (patient monitoring) device | 563: Group 3 sitter device |
| 362: Sitter (patient monitoring) device | 564: Group 4 sitter device |
| 363: Sitter (patient monitoring) device | 600: HCF |
| 36n: Sitter (patient monitoring) device | 661: Sitter device assigned to group 1 |
| 400: Patient room | 662: Sitter device assigned to group 2 |
| 402: Patient surveillance sub-system | 663: Sitter device assigned to group 3 |
| 410: Camera control device | 664: Sitter device assigned to group 4 |
| 411: Processor unit | |
| 412: Network controller | |
| 413: Video processor controller | |
| 414: Primary nonvolatile | |

In the following description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following description is, therefore, not to be taken in a limiting sense. For clarity of exposition, like features shown in the accompanying drawings are indicated with like reference numerals and similar features as shown in alternate embodiments in the drawings are indicated with similar reference numerals.

In view of the shortcomings in sitter services described above, an electronic patient sitter management system and method for implementing is presented below in accordance with various exemplary embodiments of the present invention. An exemplary sitter management system comprises patient surveillance system (for example, of the type discussed above in U.S. Pat. No. 7,477,285 and U.S. application Ser. Nos. 12/589,654, 12/804,774 and 61/513,523), a plurality of sitters (these personnel generally have relatively little medical training), each sitter is assigned a mobile computer, tablet, or smart phone (device) that is capable of receiving real time patient surveillance video generated by the patient surveillance system, for patients' rooms assigned to the respective sitter, and a sitter management device. Optimally, the presently described sitter management system is designed to manage the sitter-patient workload such that the need for intervention by higher skilled HCF professionals is minimized. In so doing, the HCF professionals are free to devote their medical talents to more appropriate tasks, commiserate with their respective skill sets.

One aim of the presently described electronic patient sitter management system and method is to efficiently distribute the sitter workload from the inefficient and expensive local sitter paradigm to more dynamic and efficient electronically managed sitter monitoring system. In accordance with one exemplary embodiment of the present invention, the electronic patient sitter management system ensures that all patients in need of sitter services are continually monitored by a sitter. In accordance with another exemplary embodiment of the present invention, the electronic patient sitter management system enables one sitter to simultaneously and continuously monitor multiple patients. In accordance with still another exemplary embodiment of the present invention, patients that are assigned to sitters that become unavailable for monitoring are temporarily and automatically rolled over to other sitters that are available for sitter monitoring duties. In accordance with still another exemplary embodiment of the present invention, the electronic patient sitter management system allows sitter managers, either manually, autonomously or both, to test and verify the sitter's alertness, verify and track sitter locations, communicate with and visually monitor the sitters. In accordance with still another exemplary embodiment of the present invention, the electronic patient sitter management system automatically logs patient and/or sitter events that may be important in evaluating a sitter's performance or for the patient's medical records.

Figure 2:
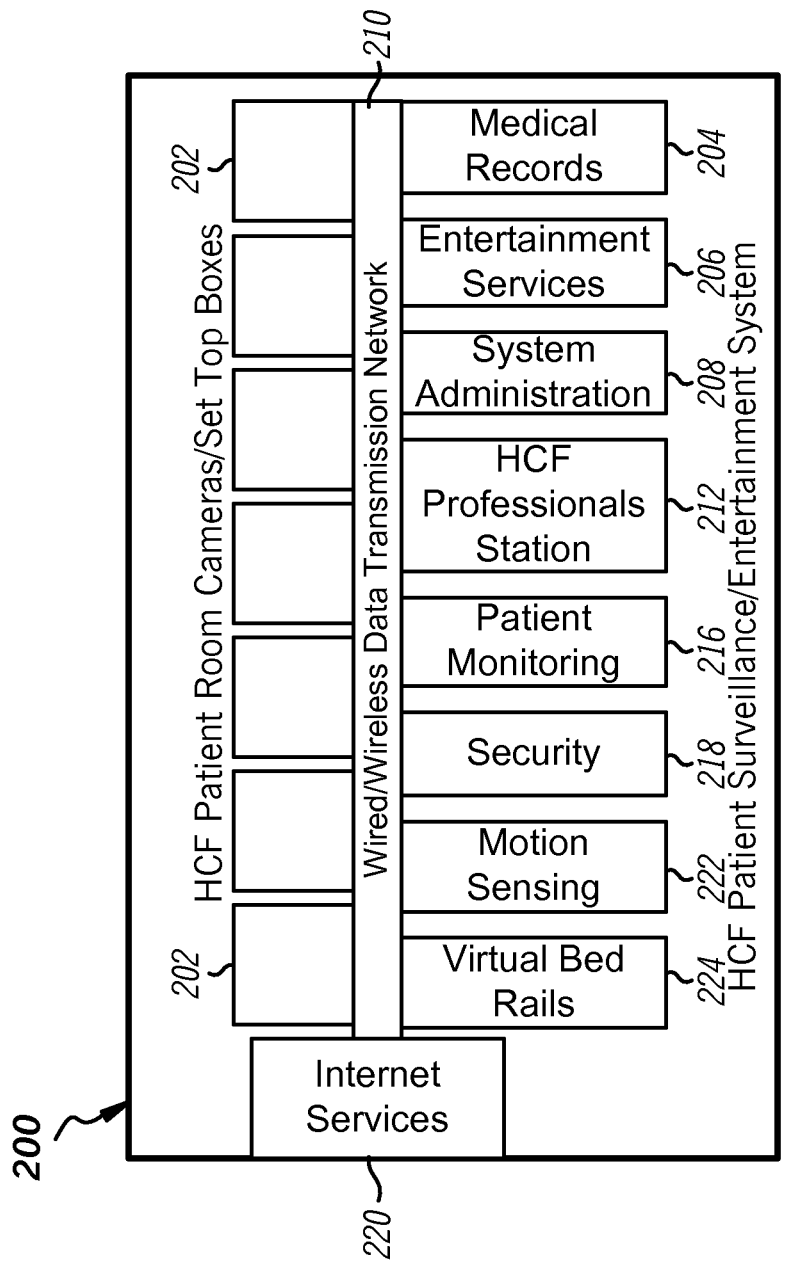
FIG. 2 is a diagram of the logical structure of an advanced patient surveillance system.
Figure 3:
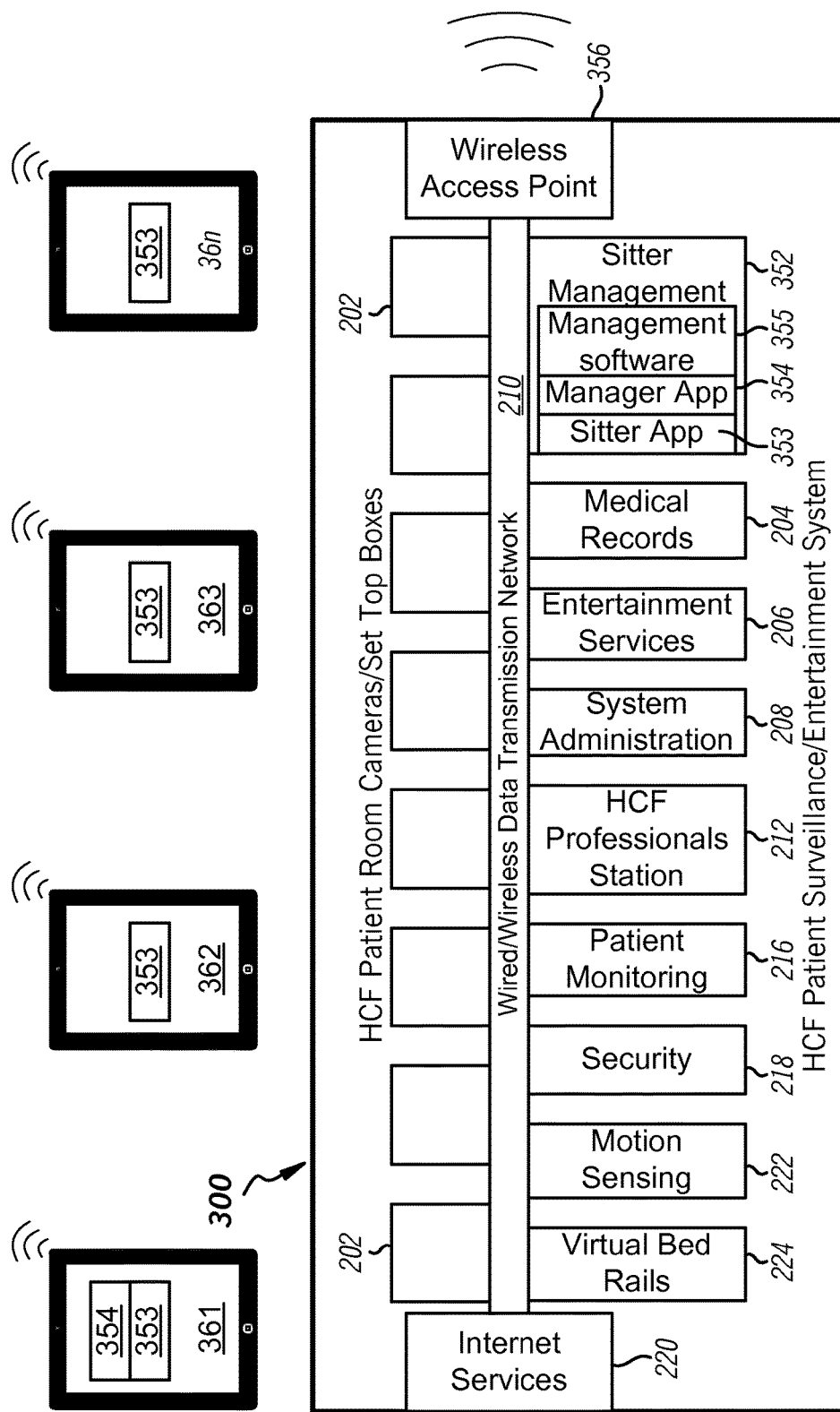
FIG. 3 is a diagram of the logical structure of an advanced patient surveillance system with an electronic patient sitter management system implemented thereon.

The presently described electronic patient sitter management system may be more completely understood by comparing the logical structure of the sitter management system with the logical structure of a patient surveillance system as previously discussed. FIG. 2 is a diagram of the logical structure of an advanced patient surveillance system and FIG. 3 is a diagram of the logical structure of an advanced patient surveillance system with an electronic patient sitter management system implemented thereon. The components represented within the figures may be implemented as physical structures or as nonphysical elements such as applications, services or the like. Typically, patient surveillance system 200 comprises a plurality of patient room video surveillance cameras 202, which may be incorporated in or with set top boxes in patient rooms (see FIGS. 4 and 5, for example). For simplicity in describing the invention, patient room video surveillance cameras 202 may be referred to alternatively as set top boxes 202, which include video cameras and or video capabilities. Each of patient room video surveillance cameras 202 is connected to data transmission network 210 for bidirectional communication with, for example, one or more monitoring and/or control devices located at HCF professional stations 212, system administration 208, security 218 or other patient surveillance management nodes (not shown). For completeness, these elements are further depicted with regard to an HCF in FIGS. 4 and 5. Also present are a plurality of HCF services that may be resident in each of patient room video surveillance cameras (set top boxes 202), or in the monitoring and/or control devices (such as the nurse monitoring device discussed above, referred to below as HCF surveillance/monitor device 460 (nurse surveillance/monitor device 460) of patient monitoring sub-system 470 with regard to FIGS. 4 and 5). These services include, but are not limited to, medical records 204 for receiving and storing patient medical records, such as patient surveillance video, entertainment services 206 coupled to the patient's set top box for patient entertainment, system administration 208 for controlling and implementing administration policies (usually the HCF's network servers located at the HCF administration facilities), applications and software for, for example, patient surveillance system 200, HCF professional station 212 for receiving and viewing patient surveillance video in real time and for communicating and controlling service in patient room video surveillance cameras 202, security 218 for monitoring the security of patient surveillance system 200 and the patients, motion sensing service 222 for detecting motion within a video stream from patient room video surveillance cameras 202 and, optimally, for discriminating patient movements from motion in the video, and finally, virtual bed rails services (or chair rails) 224 for detecting patients movements and predicting a potential patient fall from those patient movements. Finally, patient surveillance system 200 includes Internet service 220 which enables patients and HCF professionals access to the Internet.

Patient surveillance system 300 shown in FIG. 3, comprises all of the service/hardware elements discussed above, and integrates an electronic patient sitter management system in accordance with an exemplary embodiment of the present invention. Basically, the presently described electronic patient sitter management system is a sitter management service that interacts with and communicates with a plurality of remotely located devices used by sitters in the HCF. These sitter management devices comprises, for example, sitter's patient monitoring devices 361, 362, 363 through 36n (referred to alternatively as "sitter devices," "wireless sitter devices" and sitter device(s) 360) and are primarily used by sitters for displaying a plurality of real time surveillance videos taken from a plurality of patient's rooms (and other relevant information). Each of sitter devices 360 contains a network connection for connecting to data transmission network 210, optimally wirelessly linked via one or more wireless access points 356. This enables each of sitter devices 360 to receive real time patient surveillance video and other pertinent real-time patient information, from one or more of patient room video surveillance cameras 202 that are assigned to the particular sitter logged onto the sitter device.

Also comprising the electronic patient sitter management system is sitter management service 352, which essentially comprises three subservices or software applications that interact with one-another and other HCF devices and equipment: sitter application(s) 353 for use by a sitter on, for example sitter device 360; sitter manager application 354 for use by a sitter manager on, for example, nurse surveillance/monitor device 460, and sitter management software 355 that is under the control of a sitter manager and/or system administrators that essential invokes sitter policies and manages the separate applications and access to HCF devices and equipment based on those policies. Sitter management software 355 is executed on, for example, an HCF network server located at system administration facilities 208. Essentially, sitter management software 355 runs in the background to support sitter app 353 and sitter manager app 354 which are each running on unique devices, usually mobile, and remotely from sitter management software 355. While sitter management software 355 is resident on a physical device of some type, it is relatively unimportant for the practice of the present invention which device or where the device might be physically located. For instance, sitter management software 355 will most probably be deployed remotely from the sitters and/or sitter managers on a network server located in system administration 208 (see FIG. 5 for a representation of system administration 208 within HFC 500). However, sitter management software 355 may also be resident on devices at HCF surveillance/monitor device 460 of patient monitoring sub-system 470 located at, for example, HCF professional station 450 (nurse station 450 (again with regard to FIGS. 4 and 5). HCF professional station 450 is typically a personal computer, but might be any type of special purpose patient surveillance and control device. More particularly, because the computational requirements of sitter management software 355 are relatively meager, sitter management software 355 might also reside on one of sitter devices 361, 362, 363 through 36n that is under the control of a sitter manager.

Sitter app 353, on the other hand, is operated by and under the control of a sitter for monitoring the sitter's assigned patients and typically runs on one or all of sitter devices 361, 362, 363 through 36n; the number of authenticated instances of sitter app 353 running at any particular time is dependent on the HCF's sitter demands. These sitter devices, which will be described in greater detail below, are optimally embodied as a light weight wireless computing device of some type, usually a smart device or tablet. Alternatively, it may be possible, although far less desirable, to install instances of sitter app 353 on static devices such as on nurse monitor device 460 (see FIG. 4 below) located at HCF professional stations 212.

Sitter manager app 354 is used by sitter managers to distribute, assign, manage and monitor sitters, and to monitor the sitter's interactions with their respective patients. Sitter manager app 354 may run on virtually any device under the control of a sitter manager. If sitter management is the responsibility of a nurse or other HCF professional, sitter manager app 354 may run on nurse monitor device 460 at HCF professional stations 212. Alternatively, sitter manager app 354 may alternatively run on sitter device 360 that is under the control of a sitter manager. Notably, because instances of sitter app 353 and sitter manager app 354 are secure and require login passwords, the applications may reside, even simultaneously, on virtually any HCF device that can access network 210. Conversely, the HCF administrator may require that a fresh instance of sitter app 353 and/or sitter manager app 354 be downloaded from sitter management software 355 at each login. This flexibility enables HCF administrators and other HCF professionals to install the app, especially sitter manager app 354, on their personal smart devices for monitoring and/or managing sitter.

Optionally, a sitter should be authenticated on one of sitter devices 360 before the electronic patient sitter management system will consider the sitter for patient assignments. The initial set up and assignment involves the sitter taking possession of one of sitter devices 360, on which they are asked to register/log in to the system (see FIGS. 7A, 7B, 8A and 8B, below). Once logged in, they are assigned one or more patients/rooms from a remote management console (sitter management service 352). Optionally, patients and room assignments to each sitter are recommended based on specific needs of the patient, the sitter's experience or other qualifications and existing conditions.

If sitter device 360 is lost or stolen, the authentication is revoked and the information on the device is automatically either locked, wiped, or "bricked". Depending on policy and security requirements, one or more of the following authentication methods may be implemented. The Username/Password method is preferred where the sitter is prompted for a unique username and password in order to log in. Once logged in, any patients attached to their account are available for them to monitor (see FIGS. 7A, 7B, 8A and 8B discussed below along with screen presentations examples in all of FIGS. 11-18). Any events or actions that occur are attached to their account in the audit log (also discussed below in great detail). The Hardware Device ID method where the device's unique identifier, such as wireless MAC address or UDID, is used to validate, authenticate, and assign patients. Again, any events or actions that occur are attached to the device in the audit log (event logging is discussed below). The Assigned Device ID method where the device's manually assigned identifier, such as "Device #13", is used to validate, authenticate, and assign patients. Any events or actions that occur are attached to the device in the audit log (event logging is discussed below).

As will be understood from the following description, the presently described electronic patient sitter management system enables HCFs the ability to monitor multiple patients using a single sitter, while simultaneously managing and monitoring the performance of individual sitters, or the entire group of sitters logged on to the sitter management service at any one time. The presently described electronic patient sitter management system offers the flexibility to allow for single patient interaction by a sitter without sacrificing patient monitoring of other patients assigned to that sitter. This flexibility also enables sitters' ample opportunities for scheduled and unscheduled rest breaks. Additionally, the present electronic patient sitter management system is infinitely reconfigurable for adapting to any unforeseen and emergency events that might be encountered by the sitters or by the sitter management system. The present electronic patient sitter management system is relatively uncomplicated and as such can be readily adapted to any HCF having a patient monitoring or surveillance system. Alternatively, the present electronic patient sitter management system might be configured as a stand alone sitter-patient monitoring system by using wireless (or even wired) surveillance cameras (WIFI, Bluetooth, wireless IP or the like), positioned in patient rooms. These features will be more apparent with a discussion of an exemplary physical structure for implementing the present electronic patient sitter management system.

Figure 4:
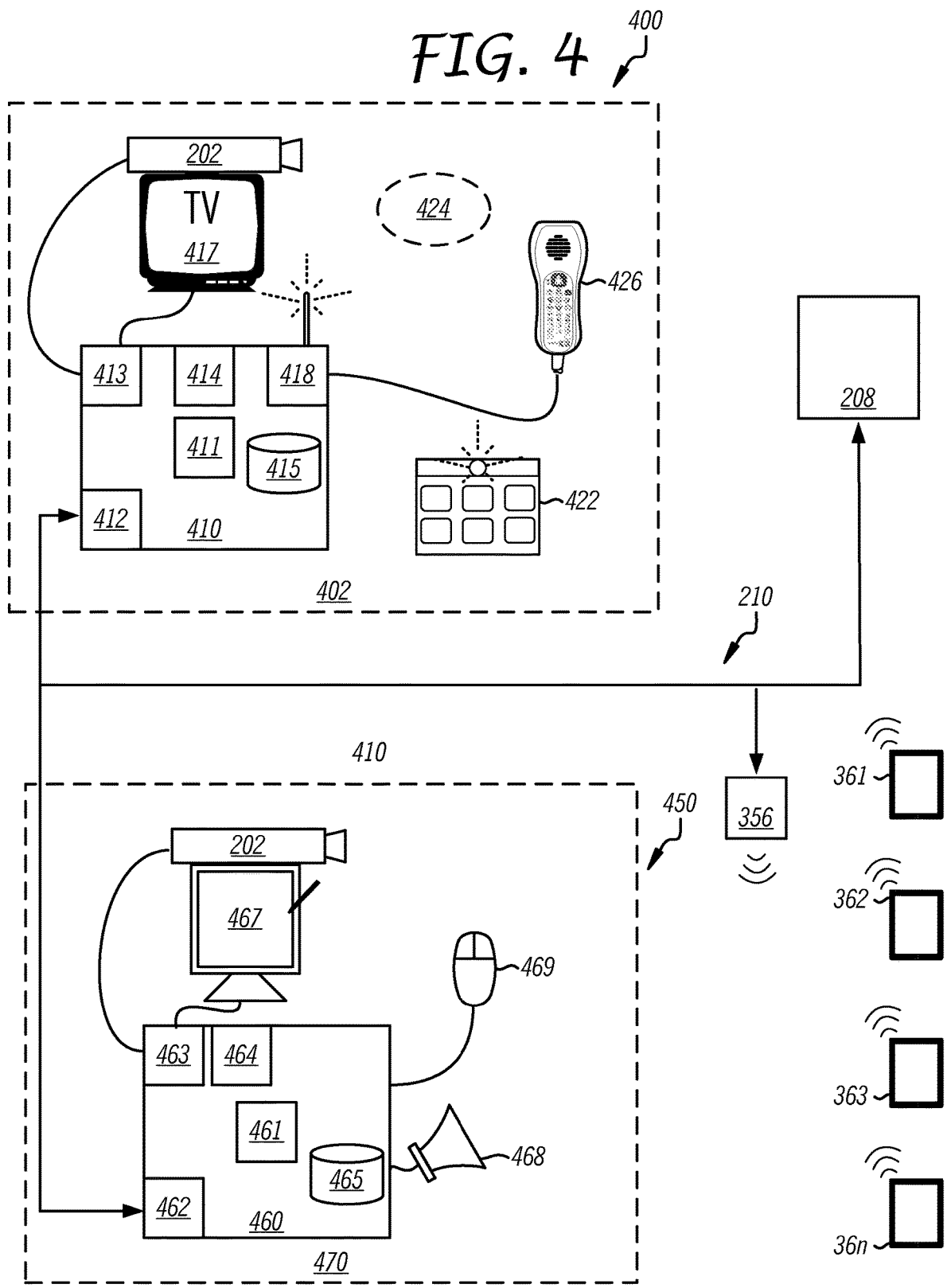
FIG. 4 is a diagram of an exemplary patient monitoring system showing improvements for implementing the present electronic patient sitter management system in accordance with one exemplary embodiment of the present invention.
Figure 5:
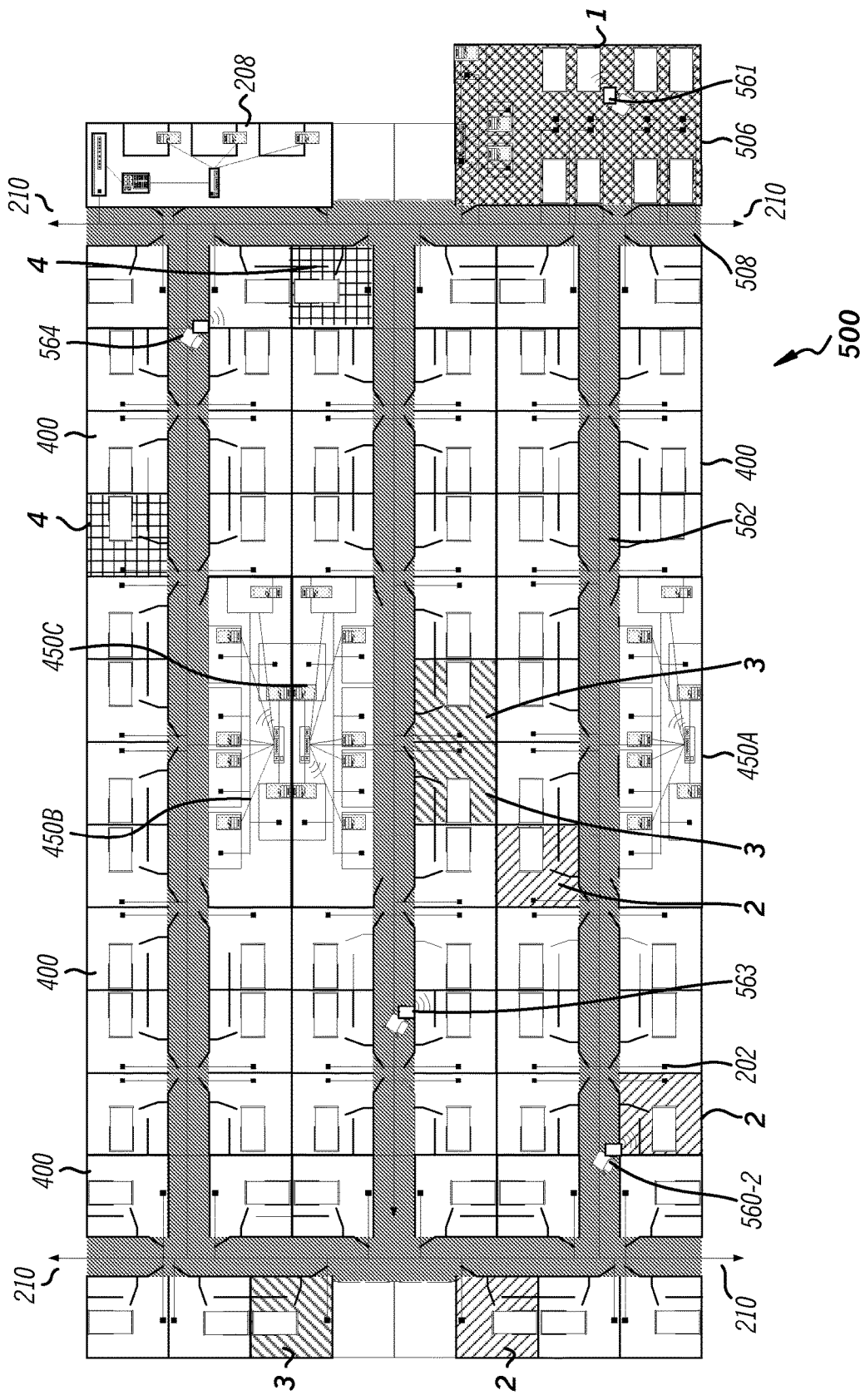
FIG. 5 is a topological view of a healthcare facility including patient rooms, multiple HCF stations, an ICU and corridors with a sitter management system implemented therein in accordance with various exemplary embodiments of the present invention.

FIG. 4 is a diagram of some exemplary components that may be considered for implementing the present electronic patient sitter management system in accordance with one exemplary embodiment of the present invention. Typically, the present electronic patient sitter management system is implemented in a patient surveillance network (a portion of or all of HCF data transmission network 210 represented in FIGS. 2 through 6), which usually comprises at least patient surveillance sub-system 402 and patient monitoring sub-system 470. As may be appreciated, the present electronic patient sitter management system may also be implemented across several physical locations, such as patient rooms 400 (containing patient surveillance sub-system 402), nurse station 450 (containing patient monitoring sub-system 470) or on a network server located at system administration 208. The separate sub-systems may also be realized in virtually any location in the HCF, such as the offices for patient administration, billing, medical records and network administration, depending on the duties of the particular location. FIG. 5, which will be discussed further below, is a diagram of an exemplary HCF in which the present electronic patient sitter management system may be implemented.

The components that are typically located in patient surveillance sub-system 402, such as in patient room 400, and accessible by the electronic patient sitter management system, includes camera control device 410 (which correlates to set top box 202 discussed above with regard to FIGS. 2 and 3) that is usually juxtaposed to television 417, but is not essential to the practice of the present invention (see FIG. 5). In most patient rooms 400, television/video monitor 417 is installed at a central location which is also a highly advantageous viewpoint location for installing surveillance camera 202. Additionally, an optional microphone (not shown) may be disposed on surveillance camera 202, camera control device 410 or connected as a separate peripheral for capturing audio in the surveillance area. Hence, for many installations, camera control device 410, television 417 and surveillance camera 202 are loosely coupled together as a unit. In any case, camera control device 410 provides the local processing, storage and network connections for the surveillance peripherals and for the present patient medical procedure documentation system. Here it should be mentioned that much of the functionality of the present invention may be embodied in a standard personal computer, however, other aspects of the present invention may require supplemental video processing and/or storage capacity. Furthermore, as may be appreciated from the description of the set-top box in copending U.S. patent application Ser. Nos. 10/735,307 and 12/151,452, camera control device 410 may also have CATV, Internet, PSTN and other capabilities that are not traditionally found in a standard personal computer.

With further regard to camera control device 410, processor unit 411 diagrammatically represents all the processing capacity, RAM and ROM memory, busses and the physical framework for storing and executing instructions for operating the other components of the control unit. Network controller 412 provides a connection to wired and/or wireless HCF distribution network 210 and to other devices connected to the HCF network, such as nurse monitor device 460 of patient monitoring sub-system 470. Video processor 413 comprises any video processing capabilities necessary for capturing, processing and/or displaying any video and/or patient medical procedure documentation screens. Video processor 413 may be integrated in a general purpose processing system or supplement the video processing capabilities of the general purpose processing system. As such, video processor 413 is responsible for receiving the captured video frames from video camera 202, analyzing video for motion (see copending U.S. patent application Ser. Nos. 10/735,307 and 12/151,452), prioritizing video frames based on content or external factors (such as labeling the frames as documentation for a patient medical procedure) and compiling medical procedure information screens for display on the local monitor, such as TV 417 (see FIG. 10).

Camera control device 410 also comprises receiver/interrogator and device communication interface 418 for communicating with a medical procedure sensing device (which may be embodied as a manual or autonomous remote interface for sensing an event indicative of the commencement of a patient medical procedure). Optimally, receiver/interrogator and device communication interface 418 provides multiple communications ports for connecting with various input devices, such as medical procedure interface 422 and/or pillow speaker interface 426. One other purpose for device communication interface 418 (or a similar device embodied within patient surveillance sub-system 402) is to interface with various patient medical sensing and monitoring devices (referred to hereinafter as vital signs monitoring devices 424) for creating visual display of a patient's vital signs (or other pertinent patient data) on sitter device 360. Those patient vital signs data that can be presented simultaneously with and superimposed on the patient's surveillance video for real time patient monitoring of patient vital signs by a sitter or the sitter's manager. Hence, medical device communication interface 418 may communicate with multiple types of patient medical sensors and vital signs monitoring devices 424, e.g., patient monitors, blood pressure monitors, sleep monitors, capnographs, fetal monitors, and the like for sensing and monitoring various bodily functions, i.e., heart rate, respiration, blood pressure, electrocardiogram, electroencephalogram and respiration gases to mention a few. These devices may be specially designed for interfacing with patient surveillance sub-system 402 and/or medical device communication interface 418 of camera control device 410 or might instead be legacy devices adapted with a specialized interface for communicating with medical device communication interface 418.

Patient medical sensors and vital signs monitoring devices 424 may operate autonomously (usually by sensing the presence of an HC professional through autonomous sensing devices) or manually by receiving manually invoked communication from a HCF professional on its interface. In either case, the aim is for camera control device 410 to receive supplemental information indicative of the commencement (and possibly termination) of a patient medical procedure. The receipt of this information enables camera control device 410 to flag any subsequently captured A/V data as documentation for the information indicative of a patient medical procedure. Hence, that A/V data may be prioritized and/or backed up locally for access in the future. To that end, camera control device 410 comprises at least one nonvolatile memory for storing A/V data documentation of a patient medical procedure.

As also depicted in FIG. 4, camera control device 410 further comprises primary nonvolatile memory 414 and secondary nonvolatile memory 415, for storing different classes of captured A/V data. The storing operations of camera control device 410 contemplate that the surveillance data received by camera control device 410 may comprise varying degrees of importance. Most surveillance data received by camera control device 410 is of relatively low importance. The surveillance data are simply transmitted to monitoring device 460, in near real time, for temporal monitoring by an HC professional, such as a nurse at nurse station 450. Since that data has a relatively low priority, it will be the first data to be temporally overwritten by fresher surveillance data received at camera control device 410. More important surveillance data received by camera control device 410 may be flagged for further review by an HC professional. This type of data might include A/V data that failed to be immediately transmitted over distribution network 210 due to network bandwidth or operation issues. Various techniques may be applied to this data for achieving a rapid resolution to the problem, such as alarms, frame rate reduction and locally backing up the A/V data. However, for the purposes of the presently described electronic patient sitter management system, it is assumed that the sitter should and will receive patient surveillance video in real-time, albeit at somewhat lower frame rates depending on the amount of data traffic on HCF data network 210.

The operation and protocols of primary nonvolatile memory 414 and secondary nonvolatile memory 415 are an important part of the present patient surveillance system, however, their precise functionality are relatively unimportant for the purposes of describing the present electronic patient sitter management system, and therefore will not be discussed in further detail (see copending U.S. patent application Ser. Nos. 10/735,307 and 12/151,452 for a discussion of primary nonvolatile memory 414 and secondary nonvolatile memory 415).

The present electronic patient sitter management system makes use of the patient surveillance system for sitter operations without the need for modifying the surveillance network or altering the manner in which the patient surveillance system operates. Hence, the HCF need not invest in extravagant modifications to the base patient surveillance network for deploying the sitter management service. Operationally, the presently described electronic patient sitter management system promotes the efficient use of sitter resources by authorizing and de-authorizing sitters to the system, managing patient distributions to authorized sitters, automatically implementing rollover policies (described below) when necessary, coupling sitter communication directly to charge HCF professionals for their respective patients (not necessarily to a single HCF station) and continually testing and verifying the alertness of the authorized sitters. However, it should not be overlooked that the primary function of sitter devices 361, 362, 363-36*n* is to allow the sitter monitoring locations to be different from the patient's room. Moreover, because sitter devices 361, 362, 363-36*n* are wireless and thereby mobile, a sitter may be positioned in an optimum location to each patient's room that is assigned to the sitter.

The deployment and distribution of sitters, along with their sitter devices, is shown on FIG. 5, which is a topological view of HCF 500 including patient rooms 400, HCF stations 450A, 4504B and 450C, ICU 506 and corridors 508. Superimposed on HCF 500 are data transmission network 210, including patient room video surveillance cameras 202 (only representative elements are labeled to reduce clutter). Also superimposed on HCF 500 is the presently described exemplary electronic patient sitter management system in accordance with various exemplary embodiments of the present invention.

For the purposes of discussion, the exemplary electronic patient sitter management system illustrated herein includes four separate sitter managed groups, designated groups 1, 2, 3 and 4. Group 1 encompasses the patients within ICU 506 and is monitored by sitter device 561, which is positioned within ICU 506. A second sitter monitor group, Group 2, is monitored by sitter device 562, which is positioned in the corridor in the upper left of HCF 500. Sitter device 562 is responsible for monitoring three patient rooms, each designated with a "2," surrounding sitter device 562. Likewise, group 3, is monitored by sitter device 563, which is responsible for monitoring the three other patient rooms designated with a "3," and group 4, is monitored by sitter device 564, which is responsible for monitoring the two patient rooms designated with a "4." In this example, each sitter and device (with the exception of ICU) is positioned in a HCF corridor. Alternatively, the sitters could be stationed at the closest of HCF stations 450A, 450B and 450C, in an empty patient room 400 or within the most centrally located patient room of the sitter's monitor group. Importantly, however, the patient group assignment is not static, but may be altered, and patient redistributed to remaining sitters, in the event that a sitter becomes unavailable. The precise mechanism for rollover policies and redistributing patients between available sitters is the subject of the disclosure associated with FIGS. 6A and 6B, however a brief description of the high level operation of the present electronic patient sitter management system and method may be useful prior to discussing rollover conditions and policies.

Figure 7A:
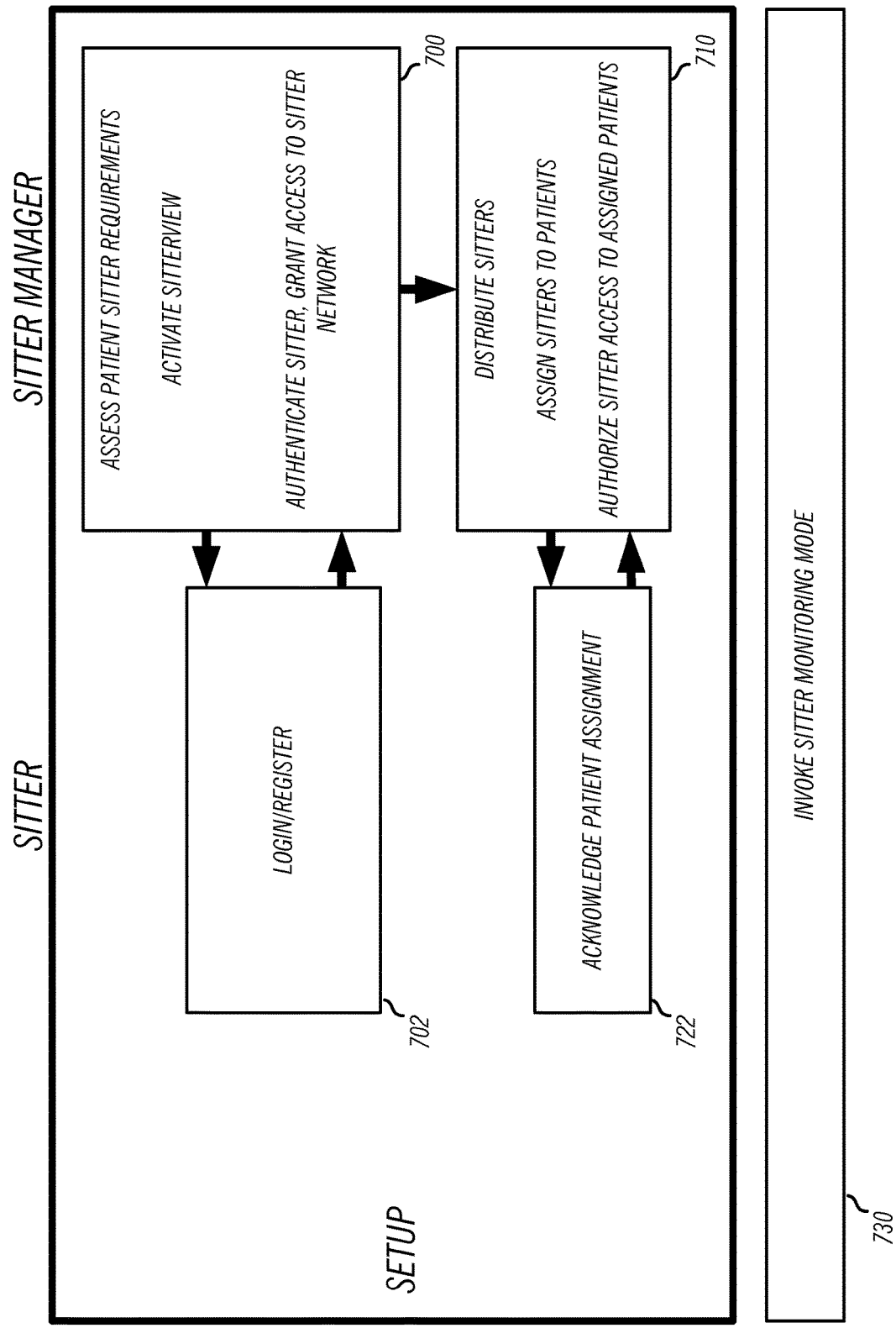

FIGS. 7A and 7B are a flowchart depicting the high level method for implementing the electronic patient sitter management service in accordance with an exemplary embodiment of the present invention. The high level operation may be subdivided into setup operations (mode) and patient monitoring operations (mode). These operations are accomplished at one of sitter device 360 (by the sitter using sitter app 353) or a sitter management device (by a sitter manager/administrator using sitter manager app 354) depending on the type of operation or responsive operation being executed. During the performance of these operations, the sitter(s) and sitter manager will be presented with various unique screens for interacting with sitter management software 355 of the electronic patient sitter management system (exemplary screens are depicted in FIGS. 12-32). Reference will be made to the screens in these figures during the discussion of operations that are relevant to the particular screen. It is expected that the sitter, at least, will view sitter device 360 having sitter app 353 executing therein, while the sitter manager that is responsible for the sitter utilizes a separate device (perhaps anther sitter device), but with sitter manager app 354 executing therein. Both sitter app 353 and sitter manager app 354 operate under the direction of sitter management software 355 of sitter management service 352, regardless of where, or which device, sitter management software 355 executes. As mentioned above, it may be more optimal to integrate sitter manager app 354 into sitter management software 355 for execution on a single device under the control of the sitter manager.

Optimally, sitter device 360 will be a mobile computing device that is wirelessly linked to HCF data network 210 through a secure wireless access point 356 and comprises touch screen 302, webcam 304 and various buttons and user controls for controlling power, speakers, accessing home screen and the like controls that are usually not convenient for use on a touch screen. While the computation requirements for sitter device 360 are only moderate, the device should be able to receive and display multiple video portals of real-time video (usually patient surveillance video) without lag. Exemplary mobile computing devices include the iPad® available from Apple, Inc. of Cupertino, Calif., the ExoPC Slate available from ExoPC of Montreal, Quebec and also the HP Slate available from the Hewlett-Packard Company of Palo Alto, Calif. Importantly, sitter device 360 selected for use should be highly flexible and scalable display capabilities in order to reconfigure information displayed (especially video) on touch screen 302 under various conditions, e.g., portrait or landscape, and in various levels of scaling depending on how many patient rooms are to be displayed, e.g., one, two, three or more patient rooms) while retaining the resolution necessary to make important sitter determinations. Importantly, sitter device 360 might also be embodied in any number of devices, such as a mobile computer, net device, or smart phone (device) without loss of any functionality to the presently described electronic patient sitter management system and method.

The sitter management software 355 component of the electronic sitter management service 352 may reside on an HCF network server located at, for example, system administration 208. Alternatively, sitter management software 355 may reside on devices at HCF surveillance/monitor device 460 of patient monitoring sub-system 470 located at, for example, HCF professional station 450 (nurse station 450 (again with regard to FIGS. 4 and 5). HCF professional station 450 is typically a personal computer, but might be any type of special purpose patient surveillance and control device. More particularly, because the computational requirements of sitter management software 355 are relatively meager, sitter management software 355 might also reside on sitter device 360 that is under the control of a sitter manager as discussed immediately above. As a practical matter, sitter management software 355 is usually installed on a remote device from sitter manager app 354, consequently a sitter manager will rarely interact with sitter management service 352 directly from the device that the service is installed, but from a device supporting sitter manager app 354. More often the sitter manager, similar to the sitter, will interact with sitter management software 355 from a remote location, such as on HCF surveillance/monitor device 460, or on sitter devices 360, that is under the physical control of the manager. Optimally, individual sitter devices 360 and other machines, interact with sitter management software 355 though remote applications, applets, routines or software programs that is resident on the particular devices (i.e., sitter app 353 and sitter manager app 354).

Returning to FIG. 7A, the figure is arranged with sitter tasks in the left column and the sitter manager's interactions (or those automated within sitter management software 355) in the right column. Related tasks/iterations are blocked together for simplifying the discussion of the high level processes. In setup mode, a sitter manager uses sitter manager app 354 to call up sitter management software 355 at one of a remote network server located in system administration 208 from local device such as HCF surveillance/monitor device 460 or even one of sitter devices 360 operated by a sitter manager (see 700). The sitter manager assesses the patient requirements for the HCF, or at least for the patients or areas that the manager is responsible. The sitter manager also considers the available sitters, including the number of sitters and locations of patient rooms needing sitter services, along with any special sitter requirements of the patients or desires for a sitter of a particular gender and perhaps the patient's identity or other factors relevant for the sitter. While many of these tasks may be accomplished automatically by sitter management software 355, it is expected that patient/sitter deployment/distribution/assignments and special sitter assignments will generally be under the privy of a sitter manager and, therefore, can be altered or updated manually by the sitter manager.

Figure 15:
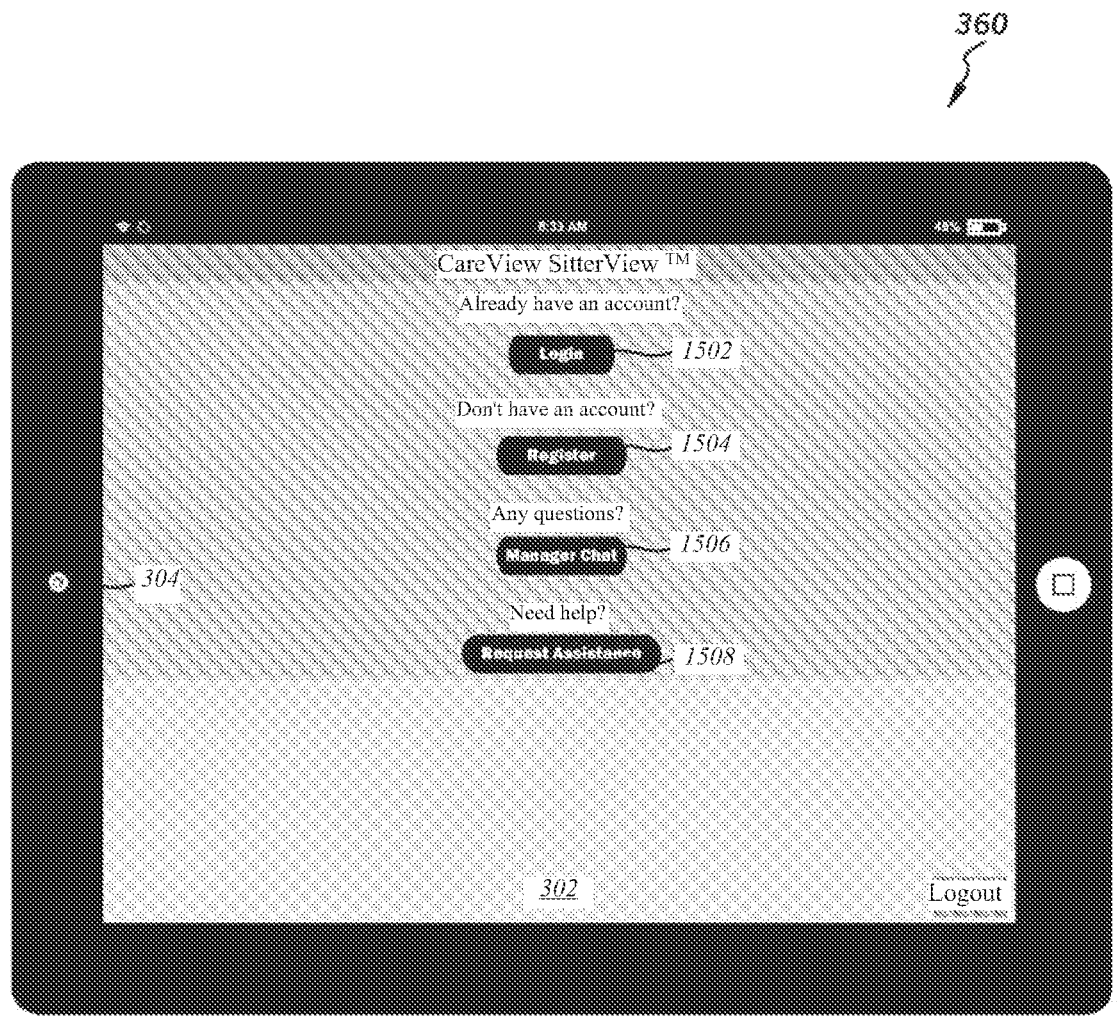
FIGS. 15-18 are diagrams of various sitter log in and registration screens presented on a sitter device and useful for registering and logging on a sitter to the presently described electronic patient sitter management system in accordance with an exemplary embodiment of the present invention.
Figure 16:
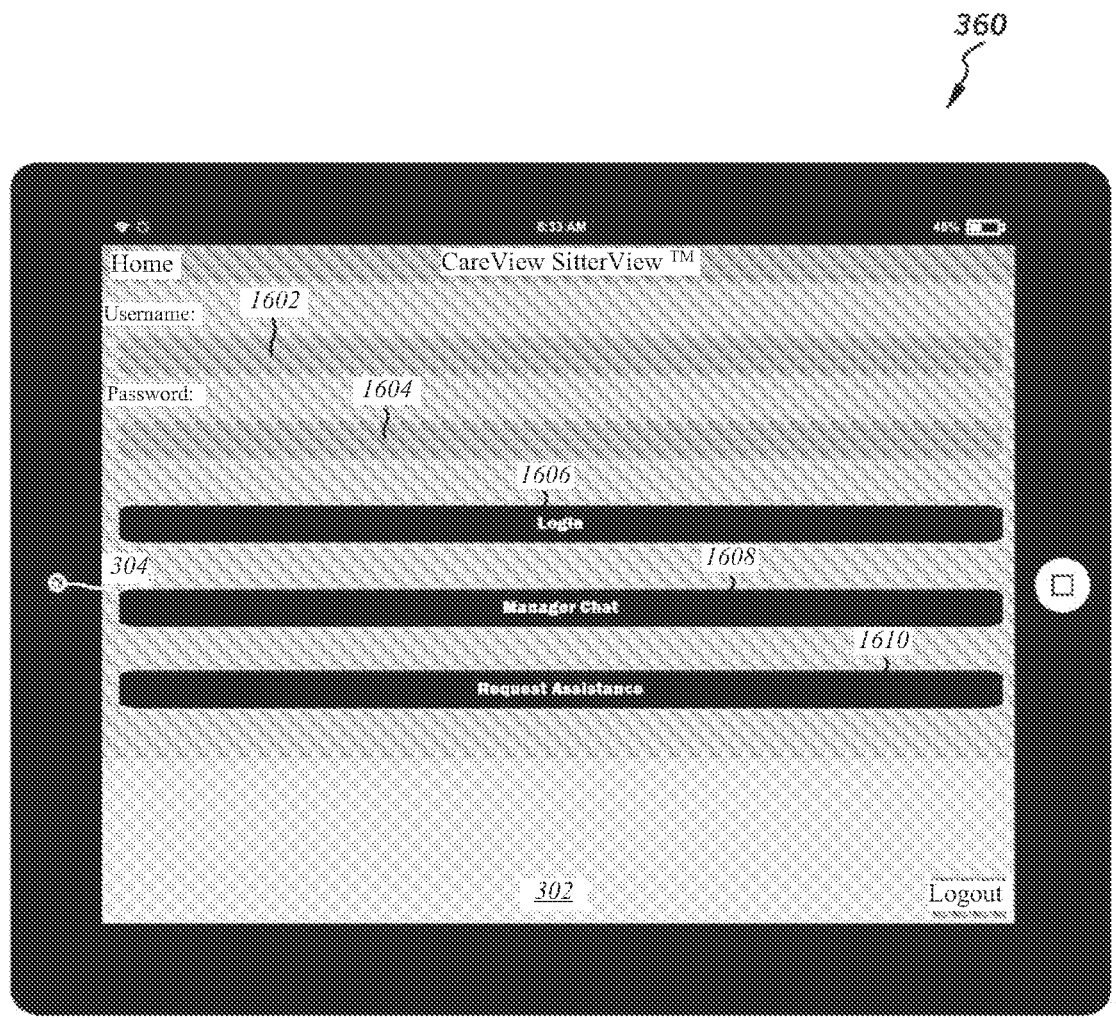
Figure 17:
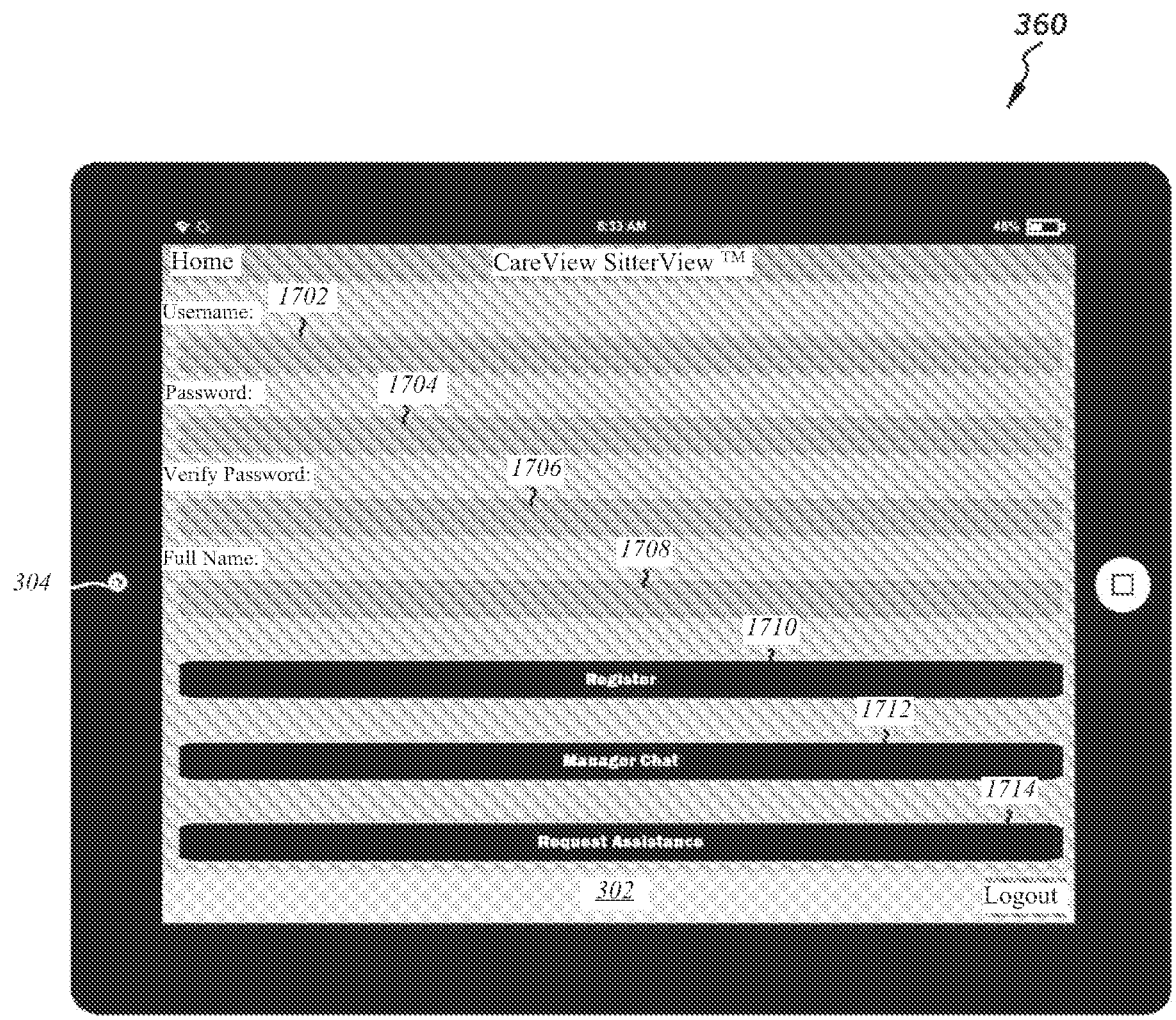

A sitter manager launches electronic patient sitter management service 352 from sitter management software 355 and in response, available sitters are presented with a login/registration selection screen on their respective sitter devices 360 as depicted in FIG. 15 (see 702). Ideally, the login/registration selection screen is user interactive screen with LOGIN button 1502, for registered sitters to login to electronic patient sitter management service 352 and REGISTER button 1504, for unregistered sitters to register with electronic patient sitter management service 352. Optionally, the login/registration selection screen may also contain sitter MANAGER CHAT button 1506 for establishing a chat with the sitter's manager and REQUEST ASSISTANCE button 1508 for requesting assistance with the login. FIG. 16 illustrates a basic sitter login screen with USERNAME entry field 1602, PASSWORD entry field 1604 and LOGIN button 1606. In addition, the login/registration selection screen may also contain MANAGER CHAT button 1608 and REQUEST ASSISTANCE button 1610, as in FIG. 16. FIG. 17 illustrates a sitter registration screen with USERNAME entry field 1702, PASSWORD entry field 1704 and PASSWORD reentry entry field 1706 for the sitter to selected and enter a unique username and password, and also NAME entry field 1708 for the sitter to enter a name that can be correlated to a sitter account resident at sitter management software 355. As an additional security feature, it is expected that sitter management software 355 will not authenticate any sitter registration unless a sitter account has been set up in advance at sitter management software 355 by a sitter manager or administrator. Finally, sitter login screen displays REGISTER button 1710 for the sitter to transmit the sitter's registration information to sitter management software 355 of sitter management service 352. Based on the sitter's entry data (usually by comparison with the names of sitters that may be authorized access to the system) sitter management software 355 either registers the sitter with the system, or rejects the sitter. Here again, in order to expedite and login complications, the login/registration selection screen may also contain sitter MANAGER CHAT button 1712 for establishing a chat with the sitter's manager and REQUEST ASSISTANCE button 1714 for requesting additional assistance with the login. Because a typical sitter is usually not a proficiently trained HCF professional such as a nurse, many sitter screens provide the sitter with an option to invoke a manager chat with the sitter's manager, or more often, provides the sitter with a REQUEST ASSISTANCE button, for summoning help from an appropriate source for the particular screen that the sitter is viewing. Typically, in the patient monitor mode, issuing a REQUEST ASSISTANCE command will solicit a response from an HCF professional in charge of the particular patient room being monitored, or from the sitter's manager.

Figure 18:

Upon authorization of the sitter by sitter management software 355, sitter app 353 receives a sitter login verification screen which displays a sitter name and login, as depicted in FIG. 18, and once patients are assigned to the sitter displays the assigned patient names (not shown). The purpose of the sitter login verification screen is to acknowledge the sitter's login with login identification box 1802 and to provide the sitter with temporal news and relevant information. The sitter login verification screen may also display pertinent information, news, policy and procedure changes and any special considerations or warning that might be useful to a sitter during his work shift.

With regard to the sitter manager, as sitters are granted access to sitter management service 352, the authorized sitter's names are displayed as, for example, labels on, or proximate to interactive buttons in sitter block 1100 on the manager's administrative view and sitter tool screen (see FIG. 11), shown in sitter block 1100 as SITTER1 button 1102 and SITTER2 button 1104. Here, the sitter manager assigns the sitters to patients depending on patient and HCF criteria, such as the patient's needs (medical and personal care), the location of the patients' room within the HCF (see the patient assignment block 710) and perhaps based on the patient's gender or the patient's preference for a sitter of a particular gender. By selecting one of SITTER1 button 1102 or SITTER2 button 1104, the sitter manager can view information relevant to the selected sitter, along with sitter management tools as can be appreciated from the exemplary manager's administrative view and sitter tool screen illustrated in FIG. 12. Here, the interface shows authorization tool block 1210 and sitter room assignment tool block 1220, in addition to sitter block 1100. Within the authorization tool block 1210 is LOG OUT SITTER button 1212 for forcibly de-authorizing a sitter from sitter management service 352. In sitter room assignment tool block 1220 is displayed a plurality of patient rooms. It should be appreciated that in a large or even moderately sized HCF, several HCF professionals may be designated as sitter managers. Typically, these managers will be assigned areas of the HCF (e.g., floors, corridors or wings) that are proximate to the HCF professionals' duty station. Once a sitter manager logs in, sitter management service 352 will populate the manager's assignments screen with patient rooms under her supervision and needing sitter services. In sitter room assignment tool block 1220, these patient rooms are presented as ROOM # buttons 1222 through 1234, each identifying a unique room number and having an assignment verification in the form of small block that is textured with a character or color in response to a sitter assignment being made for the room. The sitter manager uses this screen to assign sitters to patient rooms.

Notice from the exemplary manager's administrative view and sitter tool screen that the sitter manager has selected SITTER1 button 1102 because, in response to the manager's gesture, the texture of the button has echoed a change in texture. Notice also that the texture of a ROOM # button correlates to that of the sitter assigned to that specific room, for example ROOM 301 button 1232 and ROOM 302 button 1234 have the identical texture as SITTER1 button 1102. In addition, a check character has been placed in the assignment verification box for patient rooms 301 and 302, indicating that the sitter manager has manually assigned sitter one to patient rooms 301 and 302. Conversely, ROOM 300 button 1222, ROOM 303 button 1224, ROOM 304 button 1228, ROOM 305 button 1230 and ROOM 306 button 1226 are each textured differently from ROOM 301 button 1232 and ROOM 302 buttons 1234, indicating that sitter one is not assigned to those rooms.

Figure 13:
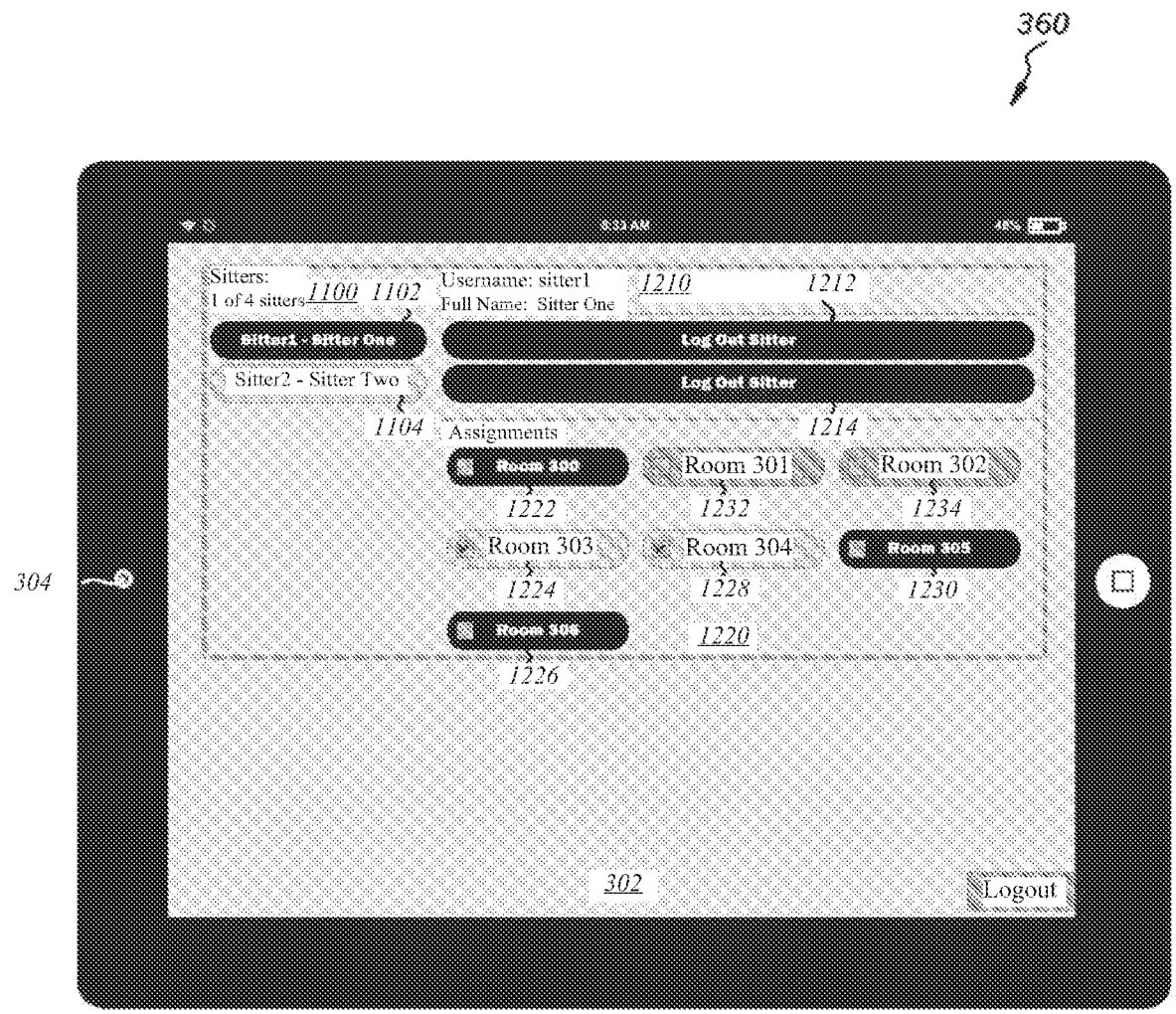
FIG. 13 is a diagram of a sitter manager patient assignment screen showing the assignments of other patients to other specifically identified sitters in accordance with an exemplary embodiment of the present invention.

Turning now to exemplary manager's administrative view and sitter tool screen shown in FIG. 13, it can be appreciated that the sitter manager has already selected SITTER2 button 1104 and in response that button is displayed in a highlighted condition on the screen with the active texture. By contrast, unselected SITTER1 button 1102 displays an inactive texture on the screen. Here again the sitter manager has selected two patient rooms for assignment to sitter two as depicted therein, as may be appreciated from the textures of ROOM 303 button 1224 and ROOM 304 button 1228 correlating to that the texture of SITTER2 button 1104. This selection by the sitter manager is further apparent from the assignment verification boxes on those buttons being filled with check characters that visually acknowledge the selections. In this assignment state, ROOM 301 button 1232 and ROOM 302 buttons 1234 have an altogether different texture from the active or inactive textures displayed on the other room button. This texture represents that the sitter manager has previously assigned those rooms to a sitter (in this case sitter one as discussed with reference to FIG. 12). ROOM 300 button 1222, ROOM 305 button 1230 and ROOM 306 button 1226 remain textured as being inactivate and not assigned.

Once at least one patient room has been assigned to a sitter, sitter management service 352 proceeds into the sitter monitoring mode for those assignments (see 730). Patient monitoring mode tasks/iterations are blocked together and depicted in FIG. 7B. Here, the sitter monitors his assigned patients on sitter devices 360 (see 752) and the sitter manager who is responsible for the sitters, supervises the sitter monitoring operations of the sitters (see 750). The primary function of sitter app 353 on sitter devices 360 is to display information relating to patient rooms assigned to a particular sitter in a manner that is most useful for the sitter for real-time monitoring of the condition of patients residing within the assigned patient rooms.

Figure 19:
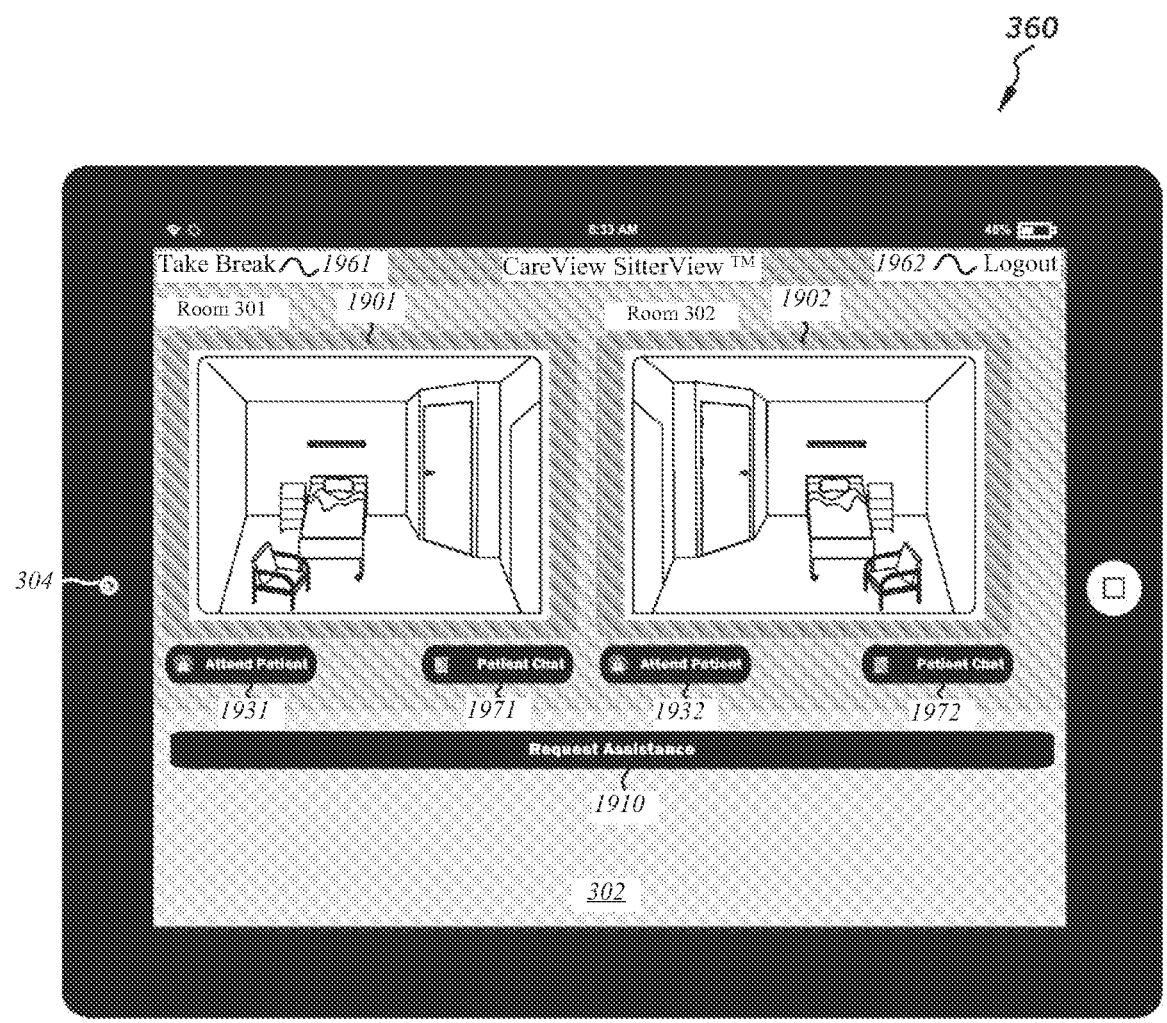
FIG. 19 is a diagram of a sitter main monitoring screen presented on a sitter device in landscape presentation mode and useful for presenting a sitter with real-time surveillance video of the sitter's assigned patients and sitter/patient tools associated with the patients in accordance with an exemplary embodiment of the present invention.
Figure 20:
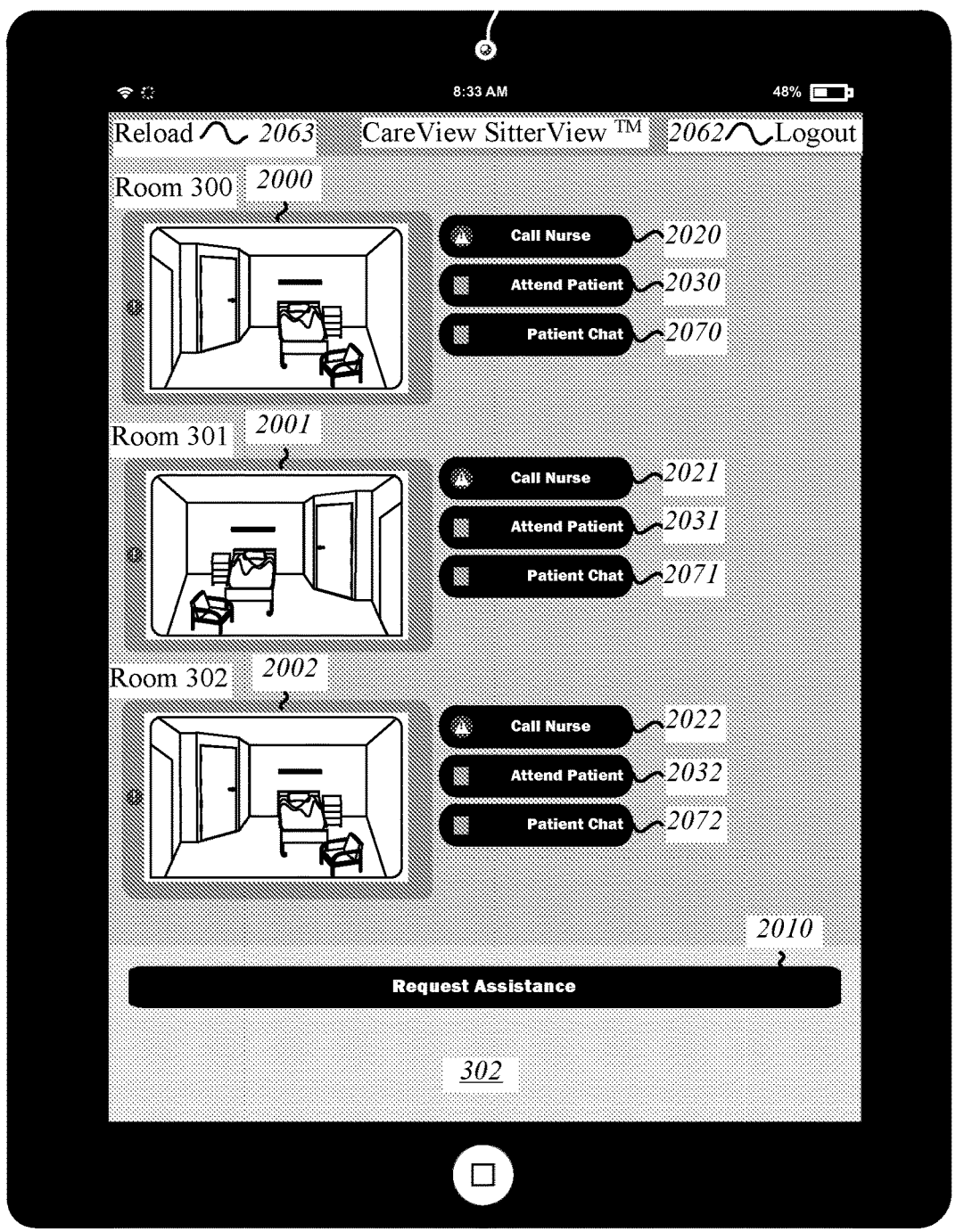
FIG. 20 is a diagram of a sitter main monitoring screen presented on a sitter device in portrait presentation mode and useful for presenting a sitter with real-time surveillance video of the sitter's assigned patients and sitter/patient tools associated with the patients in accordance with an exemplary embodiment of the present invention.

FIGS. 19 and 20 illustrate two exemplary post assignment sitter main patient monitoring screens. FIG. 19 depicts real-time surveillance video of patient rooms 301 and 302 in room surveillance frames 1901 and 1902 respectively, along with patient management tools corresponding to each assigned patient room for use by the sitter, in a landscape presentation form. Optimally, room surveillance frames 1901 and 1902 are active and interactive screen objects that convey some type of information to the sitter via color, texture or animation, or changes in the color or texture, while simultaneously being receptive for receiving sitter interactions or gestures from the sitter interacting through touch screen 302. Some exemplary patient management tools include ATTEND PATIENT buttons 1931 and 1932 for alerting sitter management software 355 and the sitter manager via sitter manager app 354 that a patient is in need of individual attention. In making an ATTEND PATIENT selection, the sitter is alerting the system that, temporarily, he will not be able to monitor his other assigned patient. Consequently, in response to the sitter selection of one of ATTEND PATIENT buttons 1931 and 1932, sitter management software 355 automatically invokes sitter rollover policies for redistributing the patient assignments from the current sitter, to sitters who are not attending individual patients themselves. Rollover, and the policies associated with sitter assignment rollovers and assignment rollover conditions, as well as recovering from rollover will be discussed below at 756 and 760 and in greater detail with regard to the flowchart depicted in FIGS. 9A and 9B. Although not shown in this illustration, the sitter main screen may display other information and patient management tools, for instance, patient vital sign readings, either as temporal digital data, analog graphic presentation over a predetermines time period, or both.

FIG. 20 depicts an alternative presentation real-time surveillance video in portrait of patient rooms 300, 301 and 302 in room surveillance frames 2000, 2001 and 2002, respectively, along with patient management tools for each assigned patient room. Optimally, surveillance frames 2000, 2001 and 2002 are also interactive and active screen objects or frames that convey some type of information to the viewer, e.g., correspondence to a particular sitter, and alarm, such as patient motion being detected by the surveillance system, virtual bedrails, etc. In accordance with this example, the sitter main patient monitoring screen is present in portrait presentation form with room surveillance frames 2000, 2001 and 2002 arranged accordingly therein. Corresponding to each room surveillance frame is ATTEND PATIENT buttons 2030, 2031 and 2032, similar to that depicted in FIG. 19, but also displays NURSE CALL buttons 2020, 2021 and 2022. Typically, an attending nurse is called from a "nurse call button" located in a patient's room, usually located on a pillow speaker, but a supplemental call button may be optionally provided on the SitterView sitter main patient monitoring screen. Additionally, the SitterView sitter main patient monitoring screen may display other patient information not shown in these figures, such as patient names, patient vital signs or other medical information, special patient care instructions, etc. Within each screen presentation mode, whether landscape presentation form, portrait presentation form or some other presentation form, the patient room surveillance frames automatically arrange themselves in the optimal arrangement and size for viewing the individual patient rooms.

Figure 21:
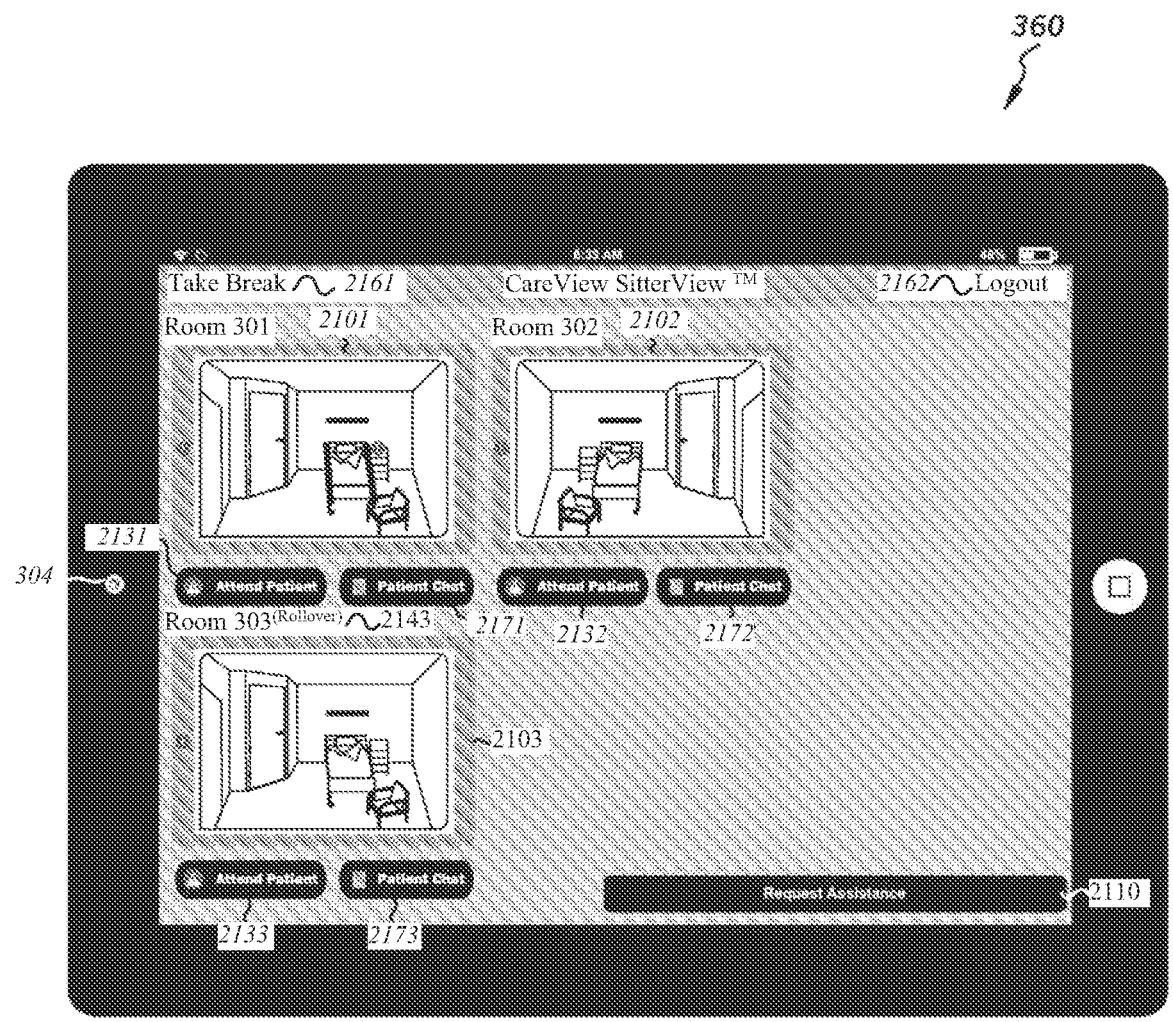
FIG. 21 is a diagram of a sitter main monitoring screen presented in FIG. 20, but on a sitter device in landscape presentation mode, also presenting real-time surveillance video of the sitter's assigned patients and sitter/patient tools associated with the patients in accordance with an exemplary embodiment of the present invention.
Figure 22:
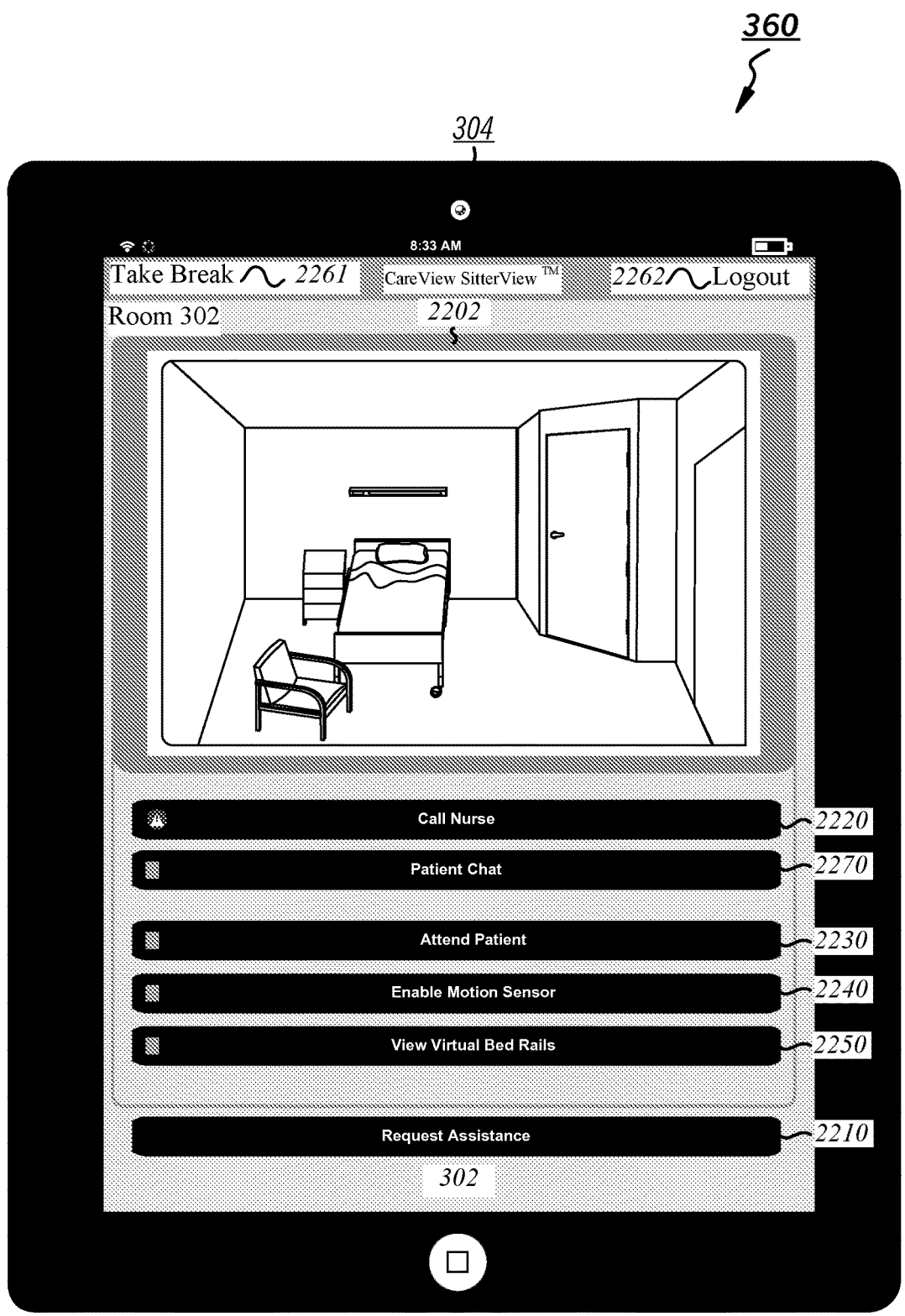
FIG. 22 is a diagram of an enhanced sitter patient monitoring screen presented on a sitter device in portrait presentation mode for isolating surveillance video taken from patient room 302 and also showing various sitter/patient tools associated with that patient in accordance with an exemplary embodiment of the present invention.

By contrast, FIG. 21 depicts an exemplary post assignment sitter main patient monitoring screen for the sitter managing the patient rooms depicted in FIG. 19, with the surveillance video of patient rooms 301 and 302 in room surveillance frames 2101 and 2102 respectively, with patient management buttons 2131 and 2132. Notice however, that patient room 303 is presented in room surveillance frame 2103. From surveillance frame legend 2143, it is apparent that room 303 has been temporarily rollover assigned to this sitter. This patient room was not initially assigned to this sitter, but only temporarily rollover assigned to the sitter in response to that patient's original sitter becoming unavailable to monitor the room 303. Patient assignment rollover will be discussed again with regard to FIGS. 9A and 9B, below.

In a typical sitter's duty shift at a HCF, a sitter will spend the majority of his time monitoring the patients in the patient rooms assigned to him. The only exceptions are usually when the sitter is attending an individual patient, the sitter is on a break or if the sitter becomes distracted. In a typical sitter manager shift at a HCF, a sitter manager will spend some time, but not all, managing the sitters under her charge. One goal of the presently described electronic patient sitter management system is to reduce the workload on the sitter manager sufficiently that the responsibility of sitter management might be relegated to existing HCF professionals, such as a charge nurse or the like. Therefore, the sitter manager's primary responsibility is to monitor sitters, but to more frequently monitor sitters under certain unusual conditions, such as during an assignment rollover. The remainder of FIG. 7B will be briefly discussed regarding each of those sitter conditions and with regard to an exemplary sitter main patient monitoring screen correlating to a condition.

Figure 14:
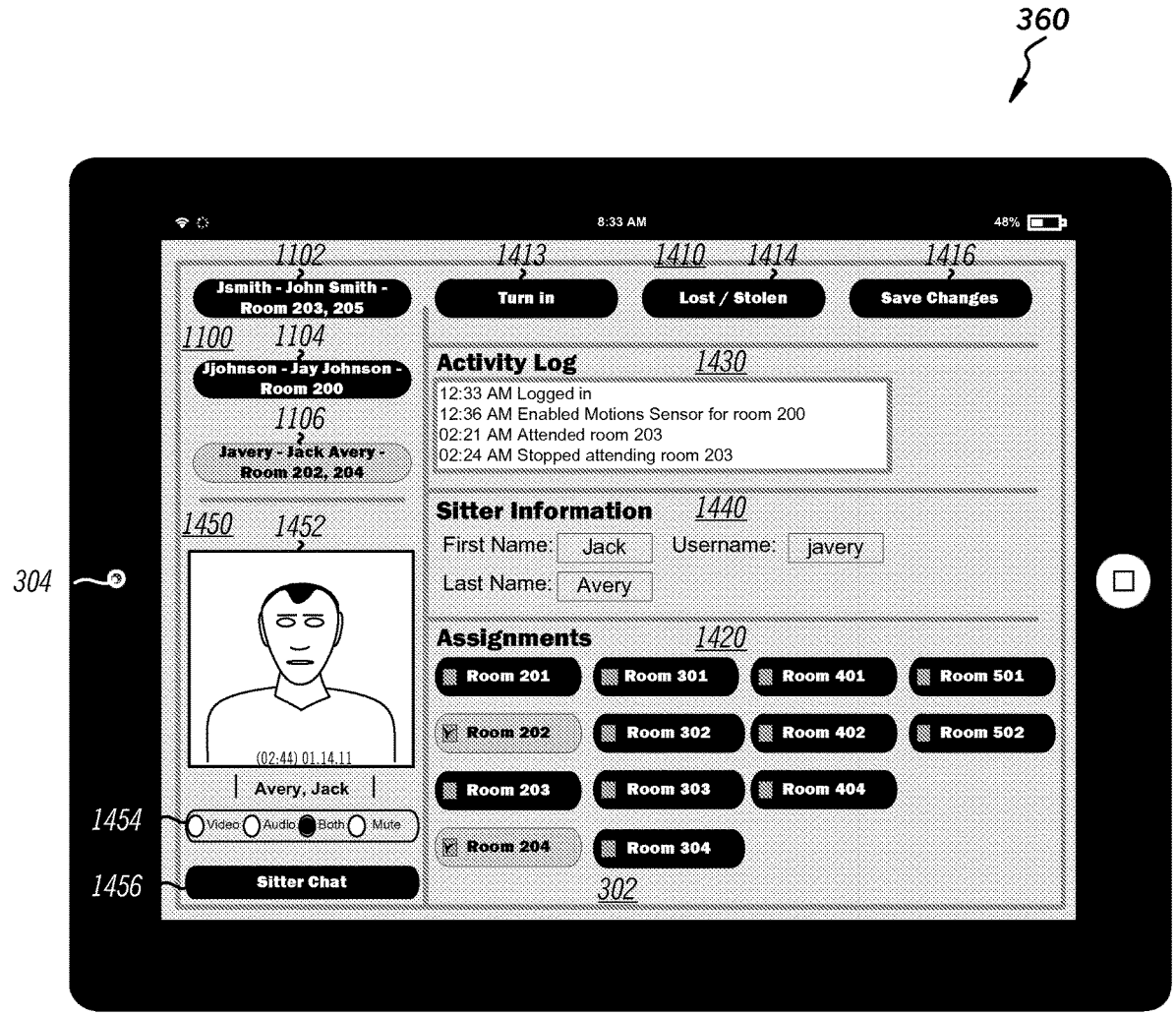
FIG. 14 is a diagram of a sitter manager monitor mode screen for monitoring a specific sitter and showing event log data other information associated with that sitter in accordance with an exemplary embodiment of the present invention.

Supervising sitters under the control of a sitter manager is, in some regards, similar to a sitter monitoring patient rooms assigned to the sitter. Recall that sitter devices 360 may take the form of a mobile computer, tablet, or smart device and as such may be configured with video conferencing capabilities such as a backward facing camera (points toward the user) and a microphone. These capabilities enable the sitter manager to monitor the sitters under her control in the same manner as the sitter utilizes patient room surveillance cameras 202 to monitor patients. FIG. 14 illustrates an exemplary sitter manager administrative view and sitter tool screen similar to those shown in FIGS. 11-13. However, sitter manager administrative view and sitter tool screen depicted in FIG. 14 provides the sitter manager with a more comprehensive view of the information relating to sitters under her control.

Essentially, exemplary sitter manager administrative view and sitter tool screen is divided into five separate sections, sitter identification block 1100, device assignment tools block 1410, sitter room assignment block 1420, sitter activity log 1430, sitter information block 1440 and finally, surveillance block 1450. Sitter identification block 1100 is populated with screen objects associated with all sitters under the control of the manager. In this example, the screen object are depicted as sitter buttons 1102, 1104 and 1106 and the sitter's names, Smith, Johnson and Avery appear as button labels corresponding to a particular sitter. Selecting any of sitter buttons 1102, 1104 and 1106 will result in information relevant to that sitter populating sitter activity log 1430, sitter information block 1440 and surveillance block 1450; the device tool in device assignment tools block 1410 will also correlate to the selected sitter's sitter devices 360. In the present illustrative example, sitter button 1106 that is associated to sitter Jack Avery has been selected and sitter information for Jack Avery is present in sitter information block 1440. This information might include the sitter's full name, username, designated location in the HCF and other information relevant to the sitter and sitter's duties. Alternatively, sitter information block 1440 may also include information identifying any special training or skills possessed by the sitter, such as advanced first aid, CPR, etc., as well as any special HCF equipment assigned to the sitter, such as defibrillators, vital signs monitors, resuscitators, aspirators or the like. With the selection of sitter button 1106, surveillance view of Jack Avery appears in sitter surveillance frame 1452, along with the sitter's name and relevant timestamp information. Below sitter surveillance frame 1452 are surveillance tools for monitoring the sitter, these may include video and audio presentation screen objects. In addition, an activity log of the sitter's recently documented events is present in sitter activity log 1430. Optimally, the log is a rolling display of events that can be traversed by the sitter manager for viewing sitter events recorded by sitter management service 352. Sitter activity log 1430 provides the sitter manager with valuable information concerning the sitter's attention to events. Documenting sitter events will be discussed in greater detail below with regard to the flowchart depicted in FIGS. 10A and 10B. In addition to display information relevant to only the selected sitter, sitter room assignment block 1420 lists all of the patient rooms having sitters. Optimally, patient rooms screen objects may have assignment verification boxes or some other feature for designated rooms that are assigned to a selected sitter. Finally, it should be mentioned that at any time, a sitter manager may access and view any one or all of the post assignment sitter monitoring screens for sitters assigned to her. In so doing, the sitter manager can get a real-time view of the sitter's patients, not just a record of previously occurring events.

Returning to FIG. 7B, the sitter monitor mode continues with the sitter accessing patient surveillance views on various sitter screens for monitoring patient under the sitter's charge (see 752 on FIG. 7B), exemplary sitter screens are depicted in FIGS. 19-32. In large part, the sitter's duties consist of monitoring a patient for any indication that the patient is in need of individual attention, and then provide that attention to that patient. Two particularly useful sitter screens for monitoring a patient are the enhanced sitter patient management screen depicted in FIGS. 22 and 23 and the enhanced sitter patient management screen depicted with patient zoom in as depicted in FIGS. 24 and 25. A sitter navigates to one of the enhanced sitter patient management screens from a post assignment sitter main patient monitoring screen by selecting a patient room for selective scrutiny, such as by clicking on surveillance frame 2102, or its interior video image, for patient room 302 on post assignment sitter main patient monitoring screens illustrated in FIG. 21. In response, an enhanced surveillance video frame for room 302 is presented with patient management tools as can be appreciated from the depictions in FIGS. 22-25.

Firstly, notice each of these exemplary screens presents a sitter with some sitter tools for interacting with sitter management service 352 and ultimately the sitter manager. These tools may include TAKE BREAK button 2161, 2261, 2361, 2461 and 2561 presented in the upper header portion of the post assignment sitter main patient monitoring screens depicted in FIGS. 22-25. This tool enables a sitter to request a break from the sitter manager. In response, the sitter manager may manually grant the sitter a temporary break from his patient monitoring duties and temporarily rollover assign the sitter's patients to other sitters while the sitter remains unavailable (on break). It is expected that the use TAKE BREAK button xx61 will require the sitter to wait for a response from sitter management service 352 before exiting his patient room monitoring assignments. However, in case of an emergency, or in a case where the sitter intends to logoff of sitter management software 355, that sitter uses LOGOUT button 1962, 2062, 2162, 2262, 2362, 2462, 2562, 2662, 2962, 3062, 3162 and 3262 as depicted in the screens presented in FIGS. 19-26 and 29-23. Typically, sitter management service 352 automatically rollover assigns the sitter's patient rooms to other available sitters in response to receiving a sitter logout without intervention from a sitter manager.

Other exemplary sitter tools for interacting with sitter management service 352 might be a RELOAD button 2063 for reloading data and real-time surveillance video frames (such as in the case of a video freeze or the like). Also, enhanced sitter patient management screens present the sitter with patient management screen objects, including ATTEND PATIENT buttons 2230 and 2330, for notifying sitter management service 352 (and the sitter manager) that the sitter will be individually attending the patient in the enhanced display (see 754 on FIG. 7B), and NURSE CALL buttons 2220 and 2320, for calling the attention of the charge nurse to the patient in the enhanced display. Each of these tools is similar to that depicted in FIG. 19 above. In addition, the enhanced sitter patient management screens also present the sitter with certain patient tools designed to aid the sitter in his patient monitoring duties, these include enabling a motion sensor associated with the patient room, depicted as ENABLE MOTION SENSOR buttons 2240, 2340, 2440 and 2540 and for viewing the superimposed virtual bed rail 2352, 2354, 2552 and 2554 on FIGS. 23 and 25, respectively, depicted as VIEW VIRTUAL BED RAILS buttons 2250 and 2350, and ENABLE VIRTUAL BED RAILS buttons 2450 and 2550. Interaction of ENABLE MOTION SENSOR buttons 2240, 2340, 2440 and 2540 invokes motion sensing service 222 for the selected patient room that alerts the sitter to any movement detected with the selected patient's room. Optimally, the motion alert is an audible in combination with a visual alert corresponding to the patient room throwing the alert, for instance, the flashing of room surveillance frames 2200, 2300, 2400 and 2500, or other visual cue to identify the correct patient room. With regard to VIEW VIRTUAL BED RAILS buttons 2250, 2350, 2450 and 2550, U.S. patent application Ser. No. 12/589,654 entitled System and Method for Predicting Patient Falls and Ser. No. 61/513,523 entitled Noise Correcting Patient Fall Risk State System and Method for Predicting Patient Falls, describe a mechanism for detecting patient falls by defining a set of virtual bed rails around the patient. Typically, virtual bed rails service 224, is set up by a HCF professional and not the sitter, however viewing virtual bed rails 2352, 2354, 2552 and 2554 superimposed on the patient surveillance video confirms to the sitter that motion sensing service 222 has been activated properly. In some case, the sitter may be granted authority to initiate virtual bed rails service 224, as well as position and/or reposition virtual bed rail objects 2352, 2354, 2552 and 2554 on the video frame.

Figure 23:
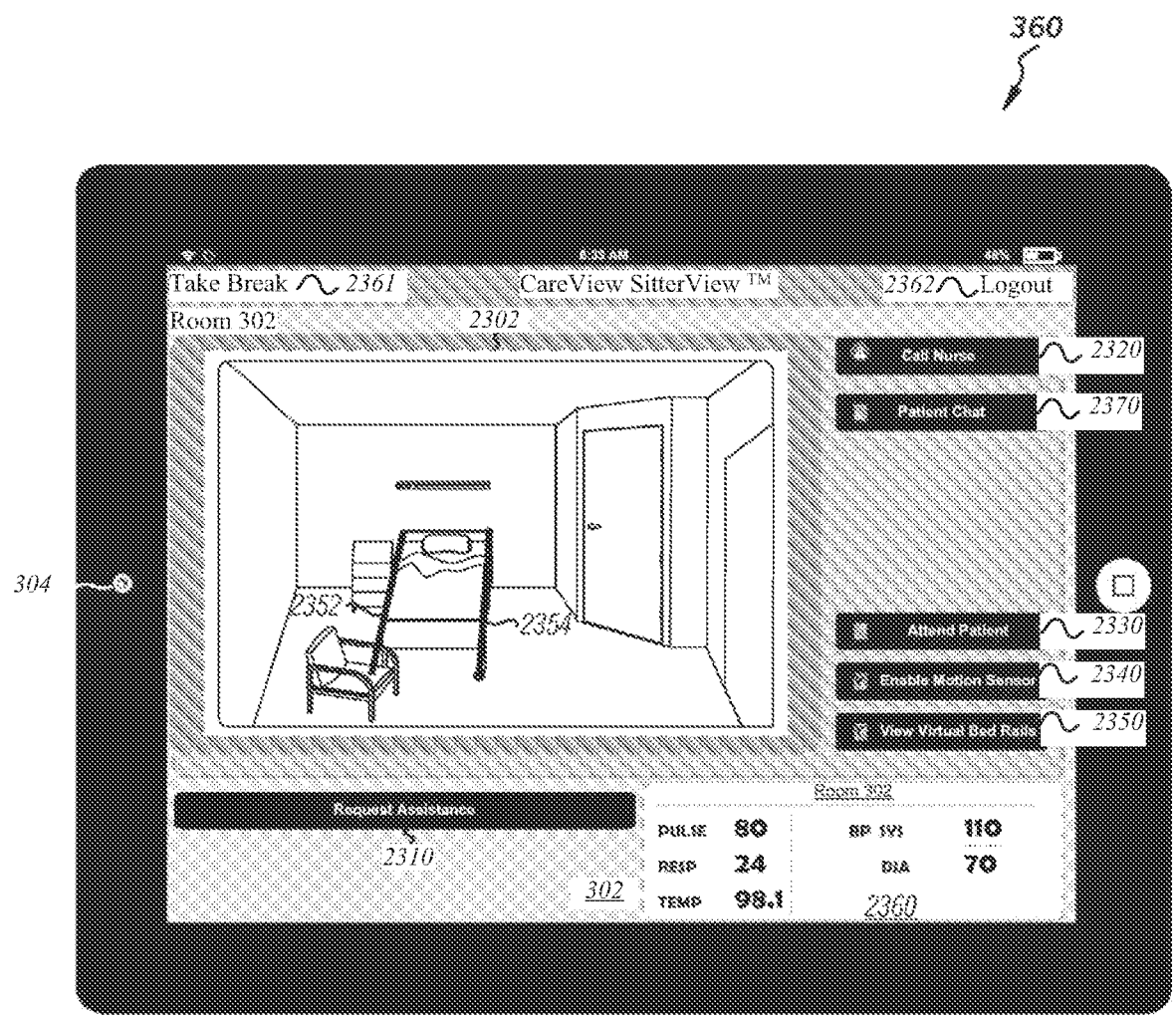
FIG. 23 is a diagram of an enhanced sitter patient monitoring screen presented in FIG. 22, but presented on a sitter device in landscape presentation mode for isolating surveillance video taken from patient room 302, showing various sitter/patient tools associated with that patient, but also showing real-time patient vital signs medical data in accordance with an exemplary embodiment of the present invention.
Figure 24:
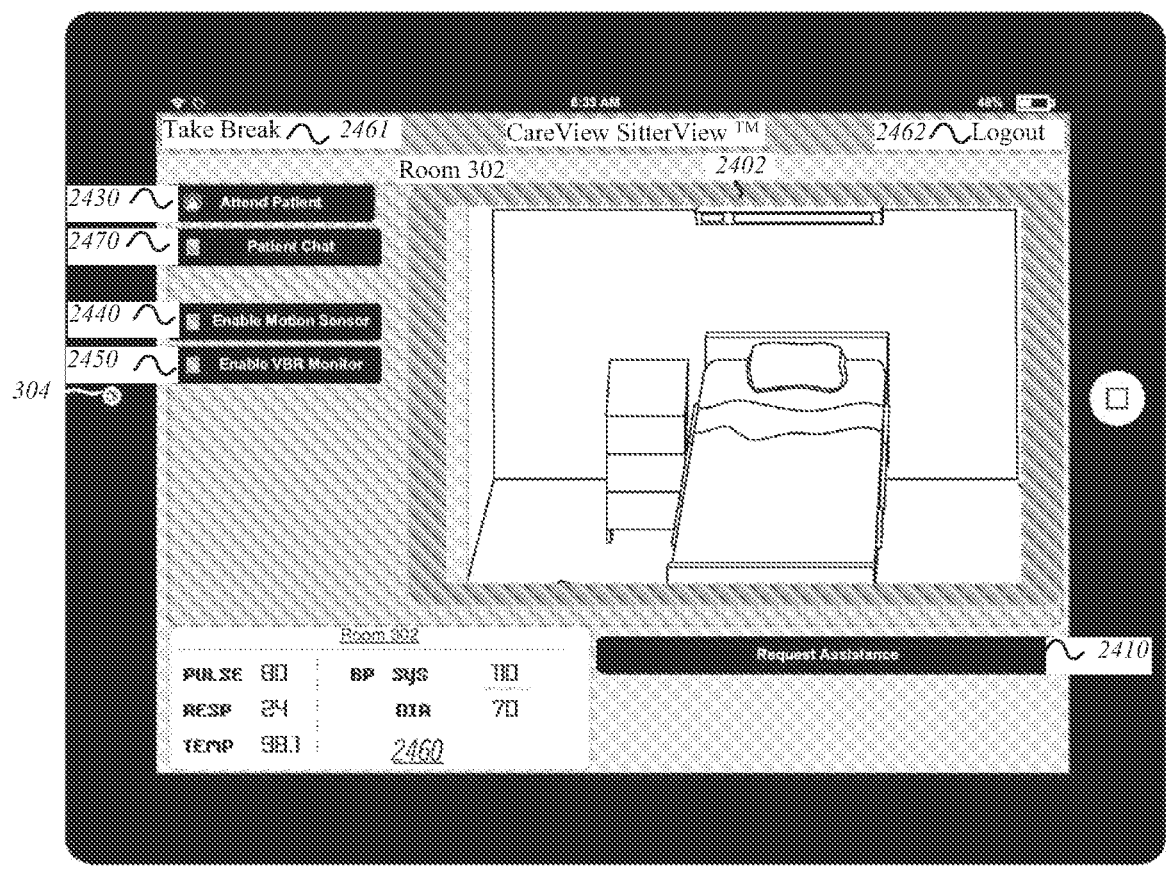
FIG. 24 is a diagram of an enhanced sitter patient monitoring screen presented in FIGS. 22 and 23, presented on a sitter device in landscape presentation mode for zooming in on the patient bed from surveillance video taken from patient room 302 and also showing various sitter/patient tools and vital signs medical data associated with that patient in accordance with an exemplary embodiment of the present invention.
Figure 25:
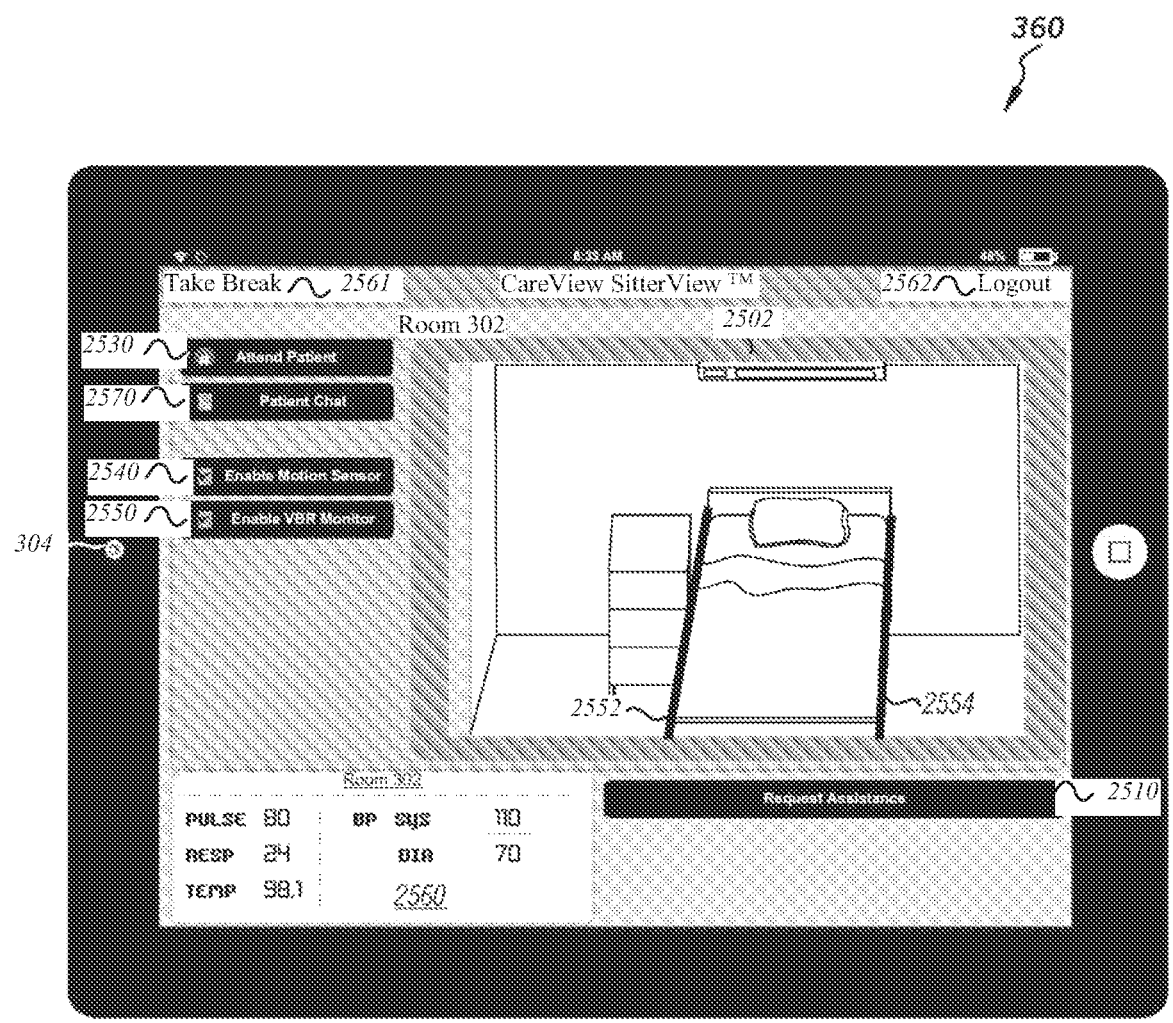
FIG. 25 is a diagram of an enhanced sitter patient monitoring screen for zooming in on the patient bed from surveillance video taken from patient room 302 and also presented in FIG. 24, the enhanced sitter patient monitoring screen is presented on a sitter device in landscape presentation mode, showing various sitter/patient tools and vital signs medical data associated with that patient, but also depicting a pair of virtual bed rails objects graphically overlaid on the patient bed in accordance with an exemplary embodiment of the present invention.

In addition to the above, notice in FIGS. 23-25 that enhanced sitter patient management screens also present the sitter with real-time patient vital sign readings in exemplary patient vital signs box 2360, 2460 and 2560. Although any patient reading from one of vital signs monitoring devices 424 may be presented in the enhanced sitter patient management screens for the sitter, as either temporal digital data, analog graphic presentation over a predetermined time period, or both, here only the digital readings for pulse, blood pressure (systolic and diastolic), respiration rate and temperature are displayed.

In any case, the enhanced sitter patient management screens can be further optimized for viewing only the patient therein using a zoom in feature on the surveillance video. Typically, this is accomplished using the diagonal finger spreading gesture across the selected surveillance video within one of room surveillance frames 2200 and 2300 (FIGS. 22 and 23, respectively) on touch screen 302 which results in the zoomed in surveillance video displayed in room surveillance frames 2400 and 2500 (FIGS. 24 and 25, respectively).

With particular attention to the sitter attending an individual patient (see 752 on FIG. 7B), frequently the sitter will be required to render individual and personal attention to a particular patient being monitored by that sitter. The sitter may determine that one of the assigned patients needs individual attention from the real-time video, or from an automated alarm associated with the assigned patient's room. As discussed immediately above, the presently described electronic patient sitter management system places a high premium on automated features for aiding the sitter and sitter manager. One such feature is the use of motion sensors, referred to in FIGS. 22-25 as ENABLE MOTION SENSOR buttons 2240, 2340, 2440 and 2540. Another automated feature usable by a sitter is the virtual bed rails movement detection, referred to in FIGS. 23 and 25 for viewing the superimposed virtual bed rail 2352, 2354, 2552 and 2554. Typically, a motion detector is a device that, when activated, issues an alert (or alarm) if motion is detected in the detection area, i.e., a patient's room, for instance. The virtual bed rails are also a type of motion detector, however this detector is a specialized for discriminating patient movement that anticipates a patient fall from a surveillance video. As described in the US patent applications identified above, a set of virtual rails are placed on the surveillance video proximate to an area containing a patient, such as a patient's bed, chair, commode, etc. The placement of these virtual rails is accomplished by HCF professionals, such as a nurse, usually not a sitter, but in some situations a sitter may be authorized to set up or modify the location of the virtual bed (chair) rails without assistance from another HCF professional.

Figure 30:
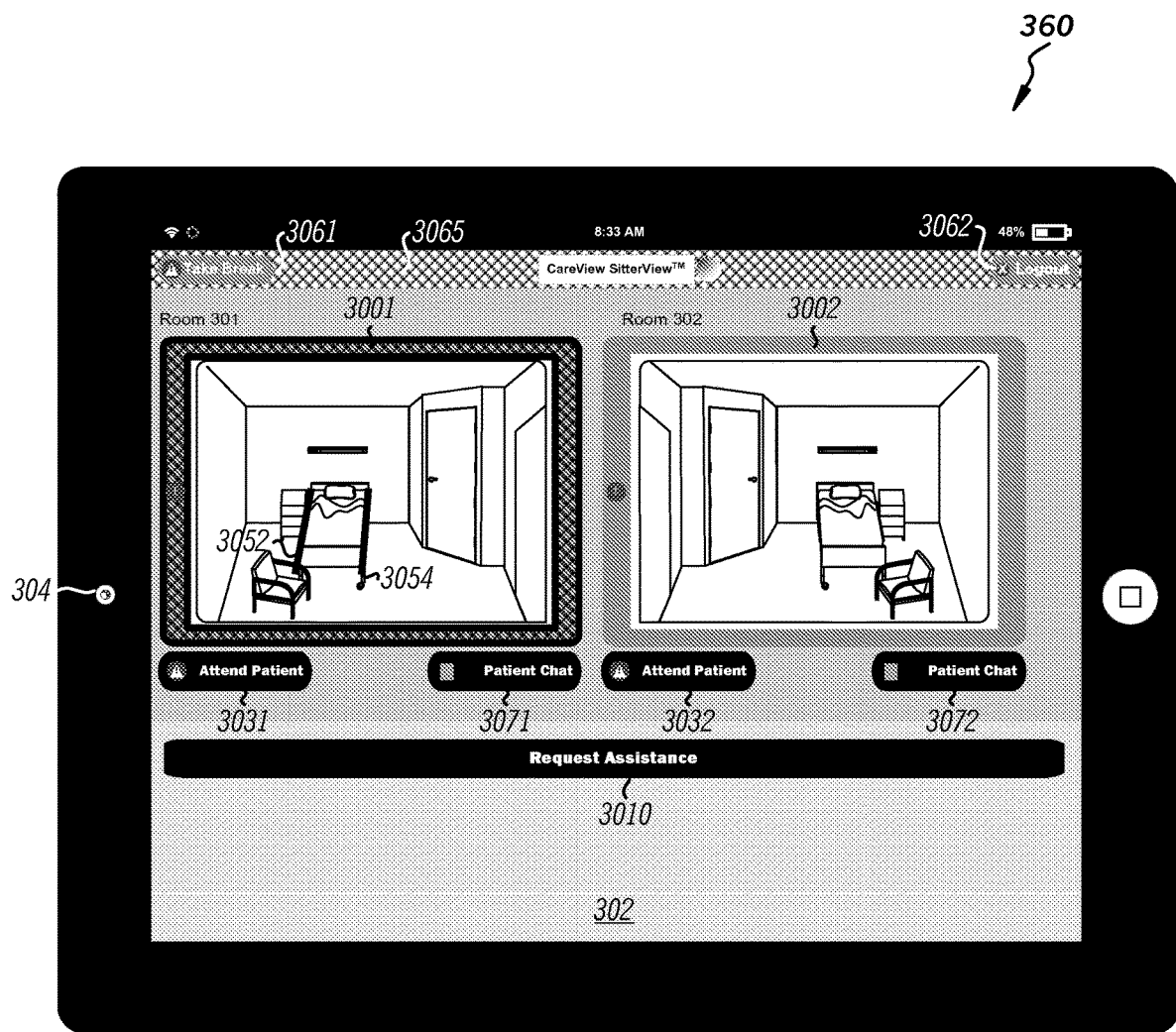
FIG. 30 is a diagram of a sitter main monitoring screen on a sitter device in landscape presentation mode, also presenting real-time surveillance video of the sitter's assigned patients and sitter/patient tools associated with the patients and further showing one patient room triggering a motion sensor alarm in accordance with an exemplary embodiment of the present invention.
Figure 31:
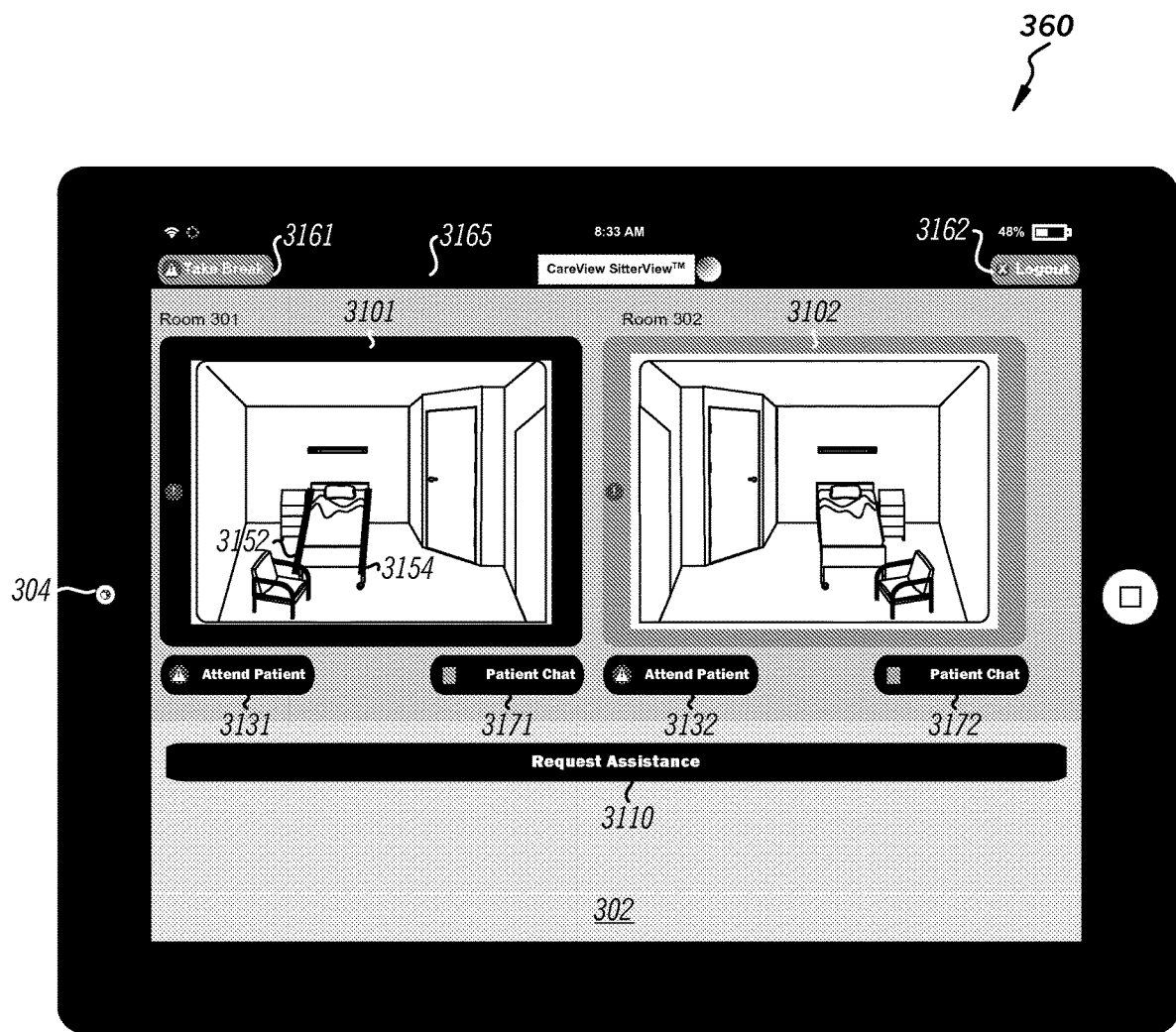
FIG. 31 is a diagram of a sitter main monitoring screen on a sitter device in landscape presentation mode, also presenting real-time surveillance video of the sitter's assigned patients and sitter/patient tools associated with the patients and further showing one patient triggering a virtual bed rail fall detection alarm in accordance with an exemplary embodiment of the present invention.
Figure 32:
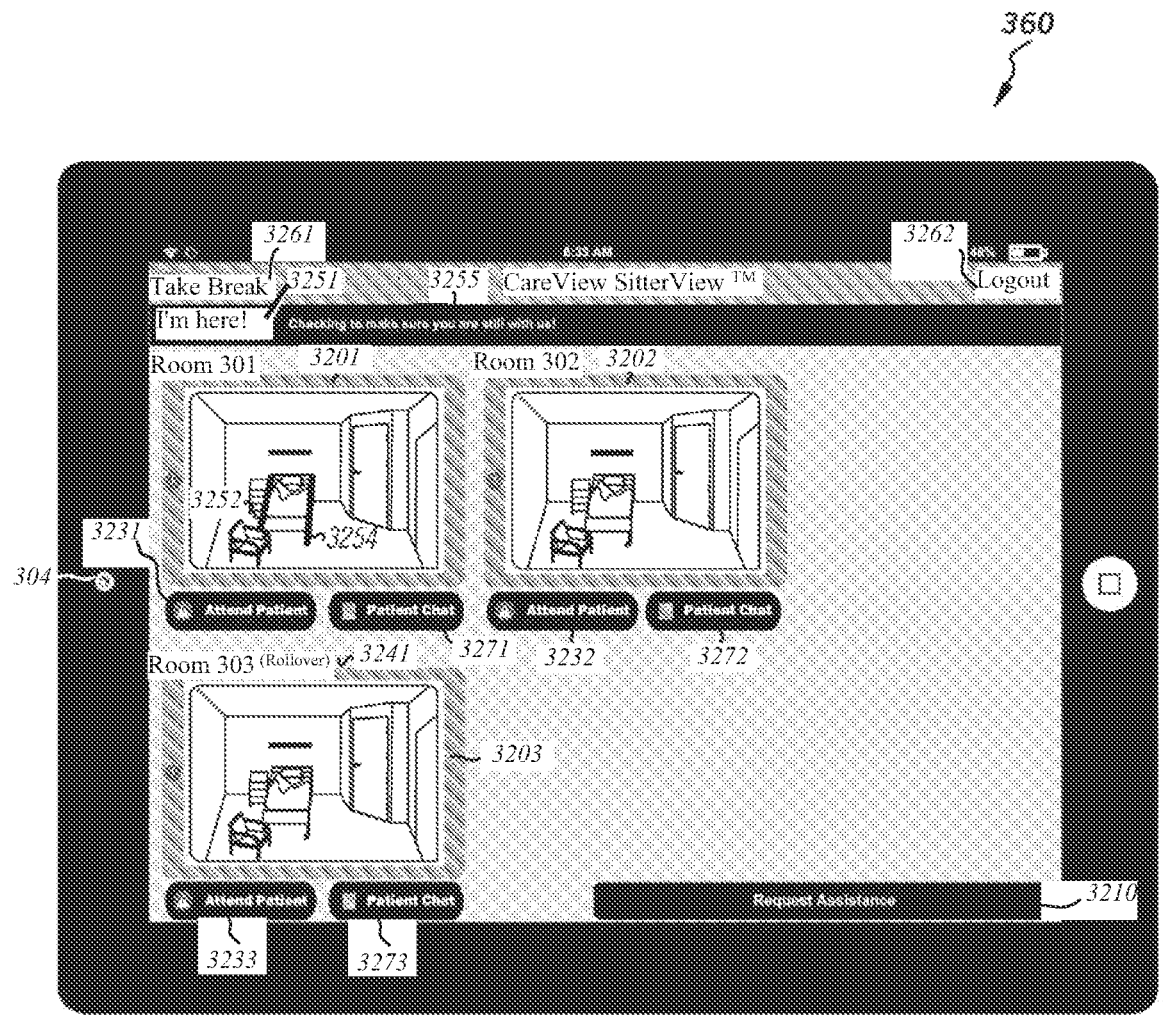
FIG. 32 is a diagram of a sitter main monitoring screen on a sitter device in landscape presentation mode, also presenting real-time surveillance video of the sitter's assigned patients and sitter/patient tools associated with the patients and further showing a sitter alertness test and sitter response objects useful for randomly testing a sitters alertness during sitting shifts in accordance with an exemplary embodiment of the present invention.

Once a motion detection device has been activated, either a sensor or virtual bed rails, the sitter will receive alarms whenever motion is detected by the motion sensing device. The motion alarm may be visual, audible or preferably a combination of visual and audible. In accordance with various exemplary embodiments of the present invention, a motion alarm should offer the sitter information as to which motion sensor triggered the alarm. For example, notice in FIGS. 30 and 31, the sitter main monitoring screen is noticeably different from that depicted in FIG. 26, and sitter main monitoring screen depicted in FIG. 30 is different from that depicted in FIG. 31. Sitter main monitoring screen depicted in FIG. 30 shows sitter management service 352 in a motion detection state precipitated by a room motion sensor in patient room 301, while FIG. 31 shows sitter management service 352 in a patient fall detection state precipitated by virtual bed rails video analysis for a patient in a patient bed in room 301. Essentially, in FIG. 30 room surveillance frame 3001 and warning screen bar 3065 are textured with a high visibility, usually animated, texture designating that the motion detector in patient room 301 has been triggered. By contrast, in response to detecting a potential patient fall via the virtual bed rails analysis, room surveillance frame 3101 and warning screen bar 3165 are textured with an even more attention grabbing texture, high visibility and usually animated, for designating that the patient room 301 has made movements that usually proceed a fall. In addition to the visual alerts, sitter management service 352 may also issue a unique audible alarm for the type of alert.

With further reference to blocks 754/756, responding to a motion alarm usually requires immediate action from the sitter. Typically, the sitter action takes one of two forms, oral communication between the sitter and patient (patient chat function between sitter device 360 and HCF patient set top box 202), and/or the sitter rendering immediate individual attention to the patient. Patient chat, or more correctly, sitter to patient chat, is preferred because it does not require the sitter to leave his monitoring station to render individual attention to a patient, hence the sitter does not become unavailable for monitoring his other assigned patients. Patient chat is invoked by the sitter through the use of PATIENT CHAT buttons 2270, 2370, 2470, 2570 and 2671 and 2672 depicted in FIGS. 22-26. Each patient chat screen object is associated with an individual patient room for communication with that room. If the patient responds appropriately to the sitter chat inquiry, the patient may not require the individual attention of the sitter. Often, however, patient chat is ineffective because the patient may not be able to communicate to the sitter (the patient may be sleeping, recovering from an anesthetic or may be otherwise incapacitated) and the patient may still require individual attention from the assigned sitter.

Figure 26:
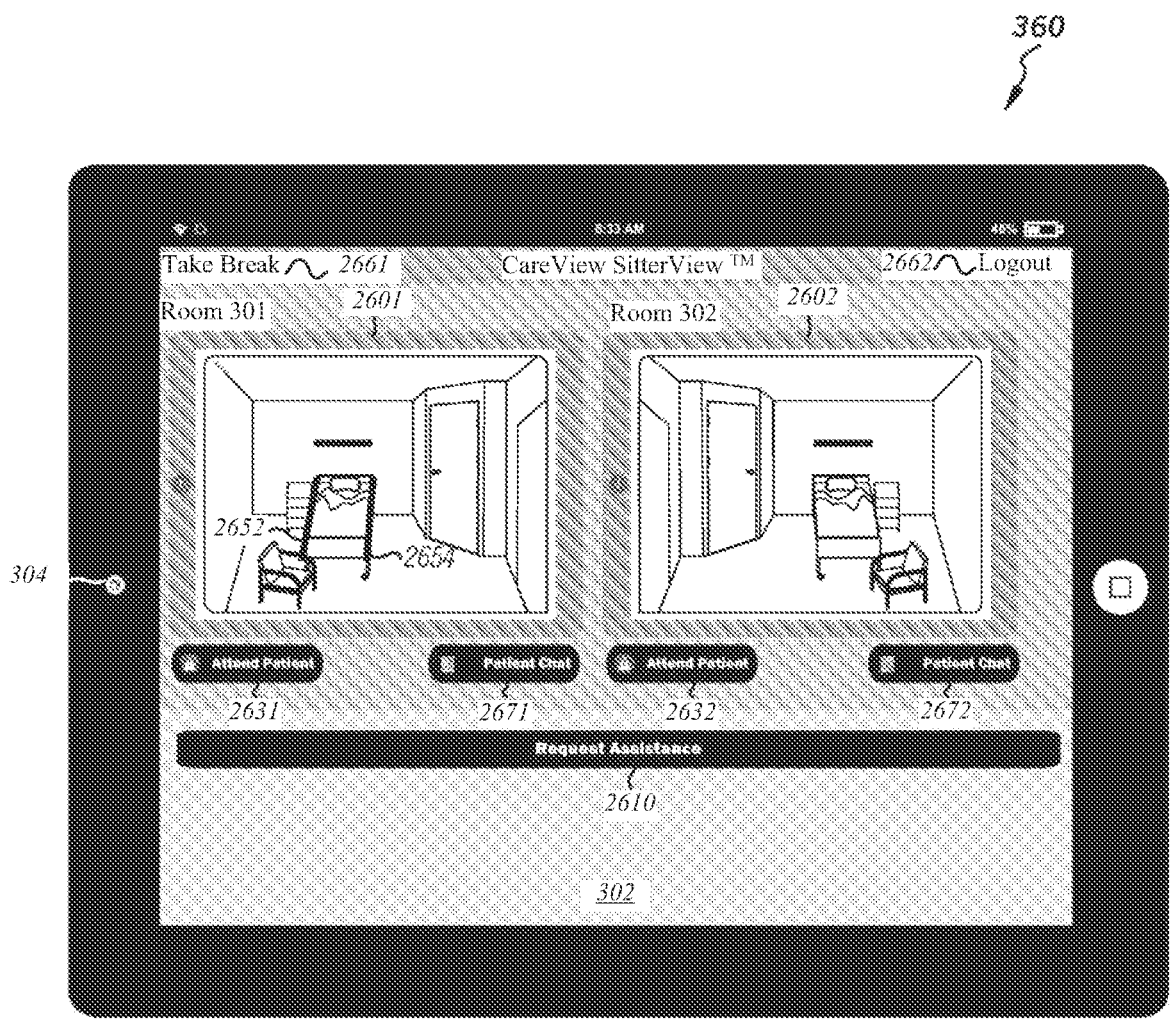
FIG. 26 is a diagram of a sitter main monitoring screen presented on a sitter device in landscape presentation mode useful for monitoring real-time surveillance video of patients assigned to a sitter, showing various sitter/patient tools and depicting a pair of virtual bed rails objects graphically overlaid on one patient bed in accordance with an exemplary embodiment of the present invention.
Figure 27:
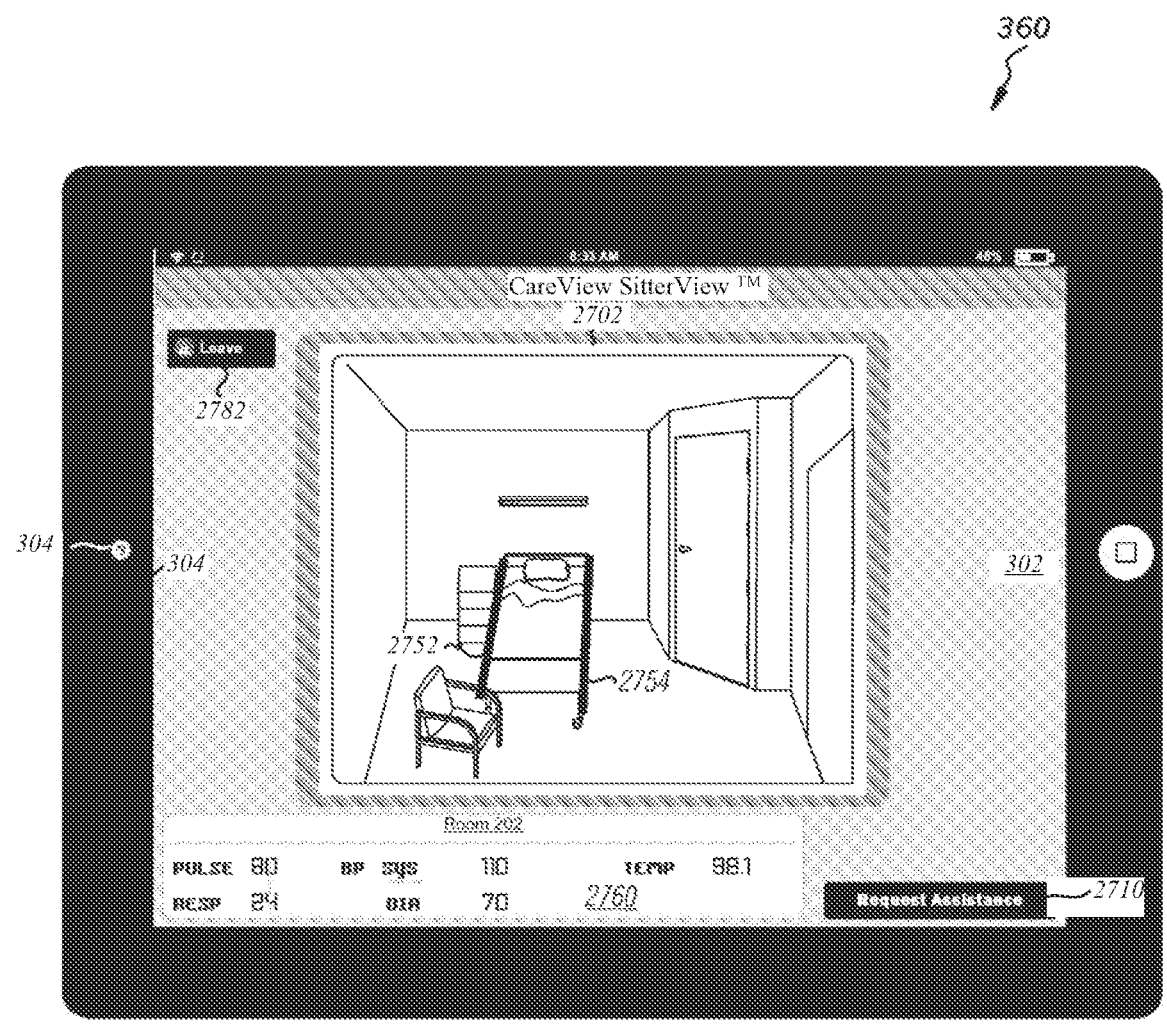
FIG. 27 is a diagram of a sitter patient attend monitoring screen for showing real-time surveillance video of a patient under individual care of the sitter, the screen is presented on a sitter device in landscape presentation mode, showing vital signs medical data associated with that patient and also depicting a pair of virtual bed rails objects graphically overlaid on the patient bed in accordance with an exemplary embodiment of the present invention.

As discussed above, once the sitter chooses to provide individual attention to a patient (i.e., leaves his monitoring station), the sitter is effectively unavailable for monitoring any other patients that are under his care. This condition is unacceptable for the HCF, therefore, the sitter's other patient assignments must be rolled over to other sitters that are available for patient monitoring. A sitter's ability to attend an individual patient cannot wait for an acknowledgement from a sitter manager, hence, rolling over patient assignments is essentially an automatic function of sitter management service 352, as will be discussed with regard to FIGS. 9, 10A and 10B below. Initially, the sitter will be monitoring his patients in his assigned patient rooms, such as viewing patient rooms 301 and 302 in surveillance frames 2601 and 2602 on post assignment sitter main patient monitoring screen depicted in FIG. 26. In the event that a sitter detects a condition or an alarm that requires his individual attention to a patient, the sitter next actuates the ATTEND PATIENT button for that patient's room, for instance one of ATTEND PATIENT buttons 2631 and 2632 (see 754). As a result, sitter management service 352 invokes the rollover policies (see 756) and the sitter is presented a sitter attend patient screen as depicted in FIG. 27 for the patient receiving individual attention, in this case patient room 302. Here, sitter management service 352 (or sitter manager app 354 commands sitter app 353) clears the sitter device 360 of all patient room surveillance frames other than the patient designated by the sitter for individual attention, see room surveillance frame 2702 displayed on sitter device 360 in FIG. 27. The sitter attend patient screen displays an enhanced surveillance video of the attended patient in surveillance frames 2601, exemplary patient vital signs box 2760 and patient tools, in the present case the sole LEAVE button 2782 for notifying sitter management service 352 that the sitter is leaving the individual attention of the patient in room 302.

With further regard to sitter management service 352 at 756, the sitters remaining patients are temporarily rollover assigned between available sitters. Those patients are automatically presented in the post assignment sitter main patient monitoring screens of the rollover assigned sitters. See for example FIG. 29, where a sitter has been assigned patient rooms 400 and 404 and presented surveillance videos in room surveillance frames 2900 and 2904, and corresponding ATTEND buttons 2930 and 2934, and where the rollover policies of sitter management service 352 issue rollover alert 2912 to alert the sitter that patient room 301 has been temporarily rollover assigned to him. With alert 2941, is presented surveillance frame 2901 and ATTEND button 2931 for the rollover assignment for monitoring the rollover assigned patient. Note that sitter management service 352 attempts to keep sitter loading approximately equivalent to all sitters (equally distribute the patients among sitters), so that if the attending sitter had been assigned other patients, those patients would most likely be temporarily rollover assigned to over available sitters. Note also that sitter management service 352 alerts the sitter's manager of the rollover. The sitter manager may then, in response, monitor the rollover policies and progress at any of sitter manager screens, or take other manually invoked action as the sitter manager deems appropriate for the situation.

Figure 28:
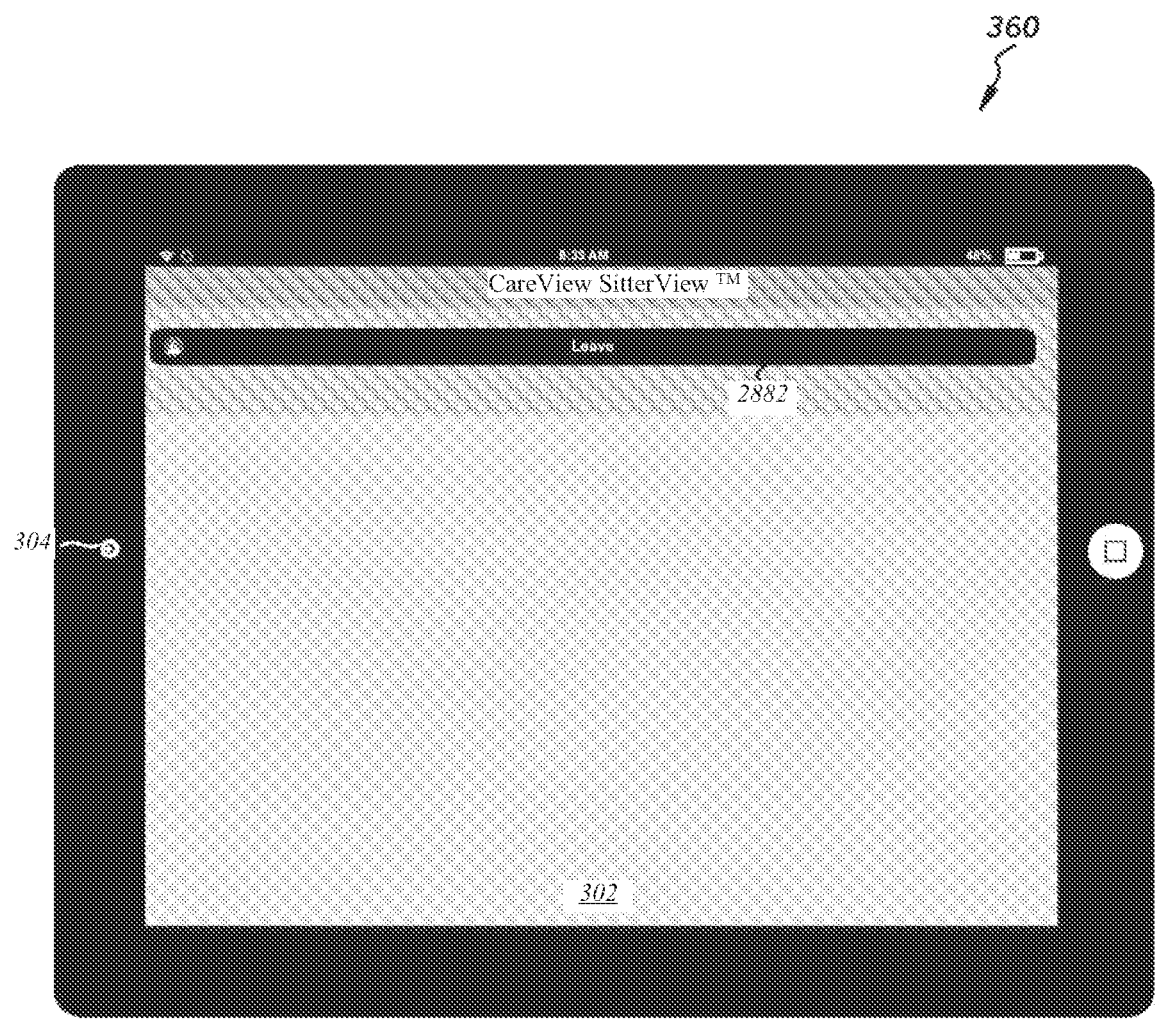
FIG. 28 is a diagram of a sitter patient attend screen showing a LEAVE screen object for acknowledging that the sitter intends to leave individual patent attend mode and begin monitoring his other assigned patients in accordance with an exemplary embodiment of the present invention.

Once the sitter's attending tasks are completed with regards to an individual patient (or the sitter is relieved in the patient's room by an HCF professional), the sitter leaves the patient's room and returns to his assigned station for continuing his sitter tasks. Typically, the sitter notifies sitter management service 352 he is available by clicking LEAVE button 2782 (shown on FIG. 27, see also 758) and in response sitter management service 352 deactivates the rollover policies (see 760). Alternatively, LEAVE button 2882 may be presented as a sole choice in a sitter patient attend screen as depicted in FIG. 28, see 762 or as an acknowledgement function the sitter selecting LEAVE button 2782 shown on FIG. 27.

Figure 29:
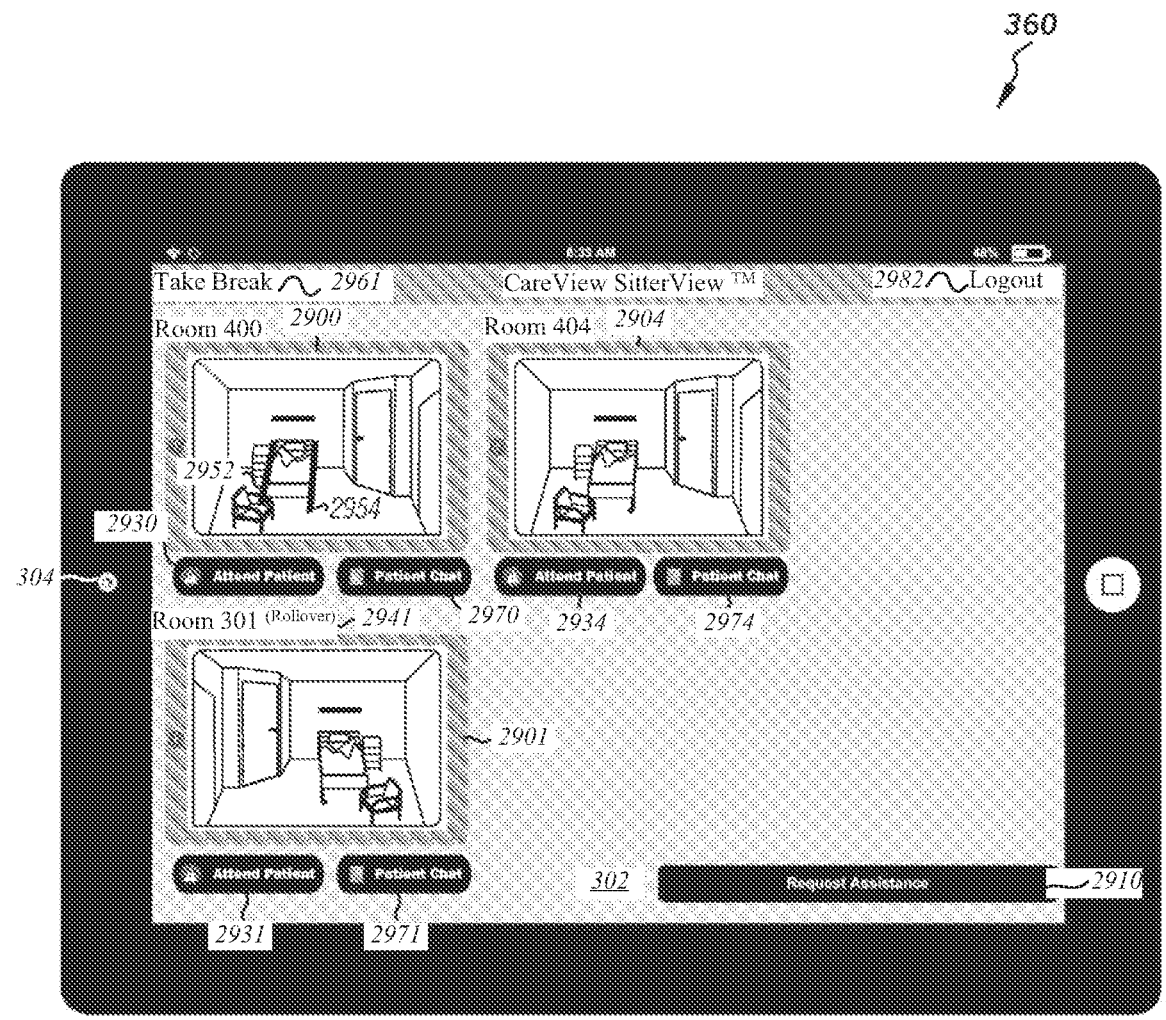
FIG. 29 is a diagram of a sitter main monitoring screen on a sitter device in landscape presentation mode, also presenting real-time surveillance video of the sitter's assigned patients and one temporary rollover assigned patient and sitter/patient tools associated with the patients and temporary rollover assigned patient in accordance with an exemplary embodiment of the present invention.

In any case, in response to receiving the LEAVE command from a sitter, sitter management service 352 rescinds the rollover assignments. The sitter is then presented with the surveillance videos for each of his originally assigned patient rooms in his post assignment sitter main patient monitoring screen, such as illustrated in FIG. 26 or FIG. 29 (assuming the sitter also has a temporary rollover patient assignment of his own). The sitter manager may verify that the rollover policies have been deactivated or the present state of the rollover by merely accessing a post assignment sitter main patient monitoring screen for one of the affected sitters, see 760. The sitter then returns to his patient monitoring duties, see 764.

Finally, it should be appreciated that the sitter must remain alert during the entire extent of his patient monitoring shift. If the sitter's attention wanes, then patients may be in jeopardy. Sitter alertness is tested in several ways (see 770 and FIG. 32), first by the sitter manager merely monitoring a surveillance video of the sitter taken by sitter device 360, see sitter surveillance frame 1452 in FIG. 14. Alternatively, for more interactive sitter response, the sitter manage may initiate a sitter chat with a sitter to inquire on the condition of a particular sitter, see SITTER CHAT button 1456 in FIG. 14. However the drawback of either of these options s that the sitter manager must be manually involved in the alertness test. Alternatively then, sitter management service 352 may issue an automated alertness test to any or all of the sitters logged in (see 770). In response, sitter management service 352 issues a sitter alertness in the form of exemplary alertness test screen bar 3255 (see FIG. 32), with sitter alertness response button 3251 (see 770). Subsequent to sitter management service 352 issuing a sitter alertness test, the sitter is allowed an appropriate time period for interacting with sitter alertness response button 3251. If sitter management service 352 receives an acknowledgement response from the sitter (see 772), the alertness test is complete. If not, sitter management service 352 must take remedial action, such as altering the sitter's manager, an HCF professional(s) in charge of the patients assigned to the sitter and/or considering the inattentive sitter as being unavailable for his patient monitoring duties and invoking the rollover policies (see 780). In the event that the sitter does not acknowledge the alertness test, the sitter manager may, manually, invoke another alertness test, initiate a sitter chat or some combination of the two prior to manually invoking the rollover assignment policies for the sitter's assigned patients.

With regard to the deployment, distribution and assignment of sitters within an HCF, sitters should be matched to patients based on the patients' sitter requirements or needs, and the sitters should be deployed about a facility based on achieving an adequate sitter response time to the sitter's assigned patients. Sitter-patient should be approximately equivalent for sitter-patient groups and should be the maximum sitter response times between sitter managed patient groups (referred to hereinafter synonymously as sitter groups). Ideally, each sitter managed patient group should have approximately the same number of patients and the maximum distance between the sitter and farthest two patients in a sitter group should also be approximately equal (this assumes that the locations of sitters' patient monitoring stations is not stationary (or fixed), but floating based on the locations of the patients rooms). The aim of the presently described electronic patient sitter management system and method is not to find a particular vantage point to view patient doors, but it is intended to find the most optimal location of a sitter's patient monitoring station in order to reduce the time it takes for the sitter to reach the sitter's patients (in some optimum locations for sitter patient monitoring stations, the sitter's patient room doors might not even be visible). The concept of sitter optimal deployment and distribution for reducing sitter response time is represented diagrammatically in FIGS. 5, 6A and 6B.

FIG. 5 is a topological view of HCF 500 including patient rooms 400, HCF stations 450A, 4504B and 4504C, ICU 506 and corridors 508. Superimposed on HCF 500 are data transmission network 210, including patient room video surveillance cameras/set top boxes 202 (only representative elements are labeled to reduce clutter within the figure). Also superimposed on HCF 500 is the presently described exemplary implementation of the electronic patient sitter management system and method for implementing in accordance with various exemplary embodiments of the present invention. For the purposes of discussion, the exemplary electronic patient sitter management system illustrated herein includes four separate sitter managed (monitor) patient groups, designated groups 1, 2, 3 and 4. Group 1 encompasses the sitter patients within ICU 506 and is monitored by sitter device 561, which is positioned within ICU 506. A second sitter managed patient group, Group 2, is monitored by sitter device 562, which is positioned in the corridor in the upper left of HCF 500. The sitter controlling sitter device 562 is responsible for monitoring three patient rooms, each designated with a "2," and surrounding the position of sitter device 562 represented in the figure. Likewise, Group 3, is monitored by sitter device 563, which is responsible for monitoring the three other patient rooms designated with a "3," and Group 4, is monitored by sitter device 564, which is responsible for monitoring the two patient rooms designated with a "4." In this example, the monitoring station locations of each sitter and device (with the exception of ICU) are flexible and currently located in corridor positions in an HCF. Alternatively, the monitoring station locations could be fixed or stationary with the sitters could be stationed within the HCF with predetermined HCF department rooms, such as at the closest of HCF stations 450A, 450B and 450C, in an empty patient room 400 or within the most centrally located patient room of the sitter's monitor group. Prior art local sitter systems placed a sitter in the room of a patient assigned to the sitter. One advantage of the presently described electronic patient sitter management system and method is that the location of sitter monitoring stations may be anywhere within the HCF, keeping sitters out of patient rooms is sometimes advantageous, but not always necessary.

With regard to rollover condition and policies, one major shortcoming of the prior art sitter systems was its inflexibility to changing in the sitters that are unavailable for performing sitter duties. If a sitter goes on break, lunch or is otherwise unavailable, the usual response of the prior art local sitter is to replace the sitter with a HCF professional until the sitter becomes available for his duties, or another sitter could be made available for monitoring the first sitter's patient. While covering for unavailable sitters might seem to be a rather random and non-repeating condition, even a medium sized HCF, eight or ten patients might require sitter services in addition to the ICU. As a practical matter, eight sitter patients might require that more than one flex sitter be staffed for replacing sitters for ordinary and scheduled breaks, lunches and personal time. If more than one sitter becomes simultaneously unavailable, the prior art local sitter system was prone to failure and placing patients in jeopardy of not being monitored due to sitter staffing.

For the purposes of describing the present invention, whenever a sitter that has been assigned a patient is not available to monitor that patient, a "rollover condition" exists because that sitter's patient assignment must be rolled over to other sitters or HCF professionals. In the prior art local sitter system where a sitter is assigned to and positioned adjacent to each patient needing sitter services, a flex sitter is constantly moving from patient room to patient room, thus, the prior art local sitter system is constantly in some state of rollover, with regard to at least one patient.

However, sitters in the presently described electronic patient sitter management system are responsible for monitoring multiple patients simultaneously and their monitoring station is not located in a room of most of their patients (at best the sitter monitoring station is located in only a single patient room). Therefore, when a patient needs individual attention from a sitter, that sitter is unavailable to monitor the remaining patients in the sitter's patient management group. This creates an even more critical condition than the prior art since multiple patients are likely not being monitored if a sitter is unavailable. Consequently, rollover policies should be implemented, within the electronic patient sitter management system, that are immediately and automatically invoked whenever a sitter becomes unavailable to monitor patients. Optimally, the rollover policy implemented should be best suited for the particular HCF implementing the policy, maintaining equal patient distribution and/or sitter/patient ratios (sitter loading), the layout of the HCF, the number of patients needing sitting services and the number of sitter patients having special needs, and the like. Implementation of a temporary patient assignment rollover is described below with regard to the description of the sitter rollover mode method described in FIGS. 9A and 9B in accordance with an exemplary embodiment of the present invention.

An exemplary rollover condition is an attempt by the described electronic patient sitter management system to distribute patients from an unavailable sitter, either to another sitter or some other entity. Typically, a particular rollover policy to be invoked (or at least a group of candidate rollover policies) is selected in advance, depending on objectives, layout and policies of the HCF, needs of the sitter patients and the scale of the sitter operation, one or more of the following rollover policies can be used.

"Blast" is a rollover policy where the remaining patients from a sitter's monitoring group are reassigned to all other sitters that are currently available, that is those that are actively monitoring patients. When the electronic patient sitter management system invokes the Blast rollover policy, rollover patients can appear in multiple devices depending on the number of available sitters. Once the sitter denotes they are leaving the single patient interaction mode on the sitters' device, the previously distributed rollover assigned patients return to the original sitter and are removed from the other sitters' sitter devices. The Blast rollover policy is extremely advantageous for handling short term and regular rollover events such as handling sitter breaks.

"Round Robin Distribution" is a rollover policy where the remaining patients are distributed to the other sitters using a round robin until they are completely distributed to other available sitters. Once the sitter denotes they are leaving the single patient interaction, the previously distributed rollover patients return to the original sitter and are removed from the others.

"Equal Distribution" is a rollover policy where the remaining patients are equally distributed to other sitters, taking into account how many patients each of the sitters are already monitoring. Sitters with the least number of patients receive the rollover patients, attempting to keep the same number of patients per sitter. Once the sitter denotes they are leaving the single patient interaction, the previously distributed rollover patients return to the original sitter and are removed from the others.

"Blueprint" is a rollover policy where the patients are sent to other sitters within a specific range based on the hospital blueprint. More specifically, this policy uses the distance from one patient room to another, in conjunction with what sitters are assigned to patients in those rooms, to determine which sitters should be close enough to handle the patients that are rolled over. The Blueprint rollover policy is very advantageous in keeping sitter response times below a threshold level of adequacy. Once the sitter denotes they are leaving the single patient interaction, the previously distributed rollover patients return to the original sitter and are removed from the others.

"Wi-Fi Proximity" rollover policy is where the patients are sent to other sitters within a specific range based on what wireless access point their device is connected to. It checks for other sitters using the same or nearby wireless access point to deduce sitters that are close enough to handle the patients that are rolled over. Once the sitter denotes they are leaving the single patient interaction, the previously distributed rollover patients return to the original sitter and are removed from the others.

"GPS" rollover policy is where the patients are sent to other sitters based on proximity using the device's GPS. This policy accounts for latitude, longitude, and altitude in order to discern the location and floor of sitters that are close enough to handle the patients that are rolled over. Once the sitter denotes they are leaving the single patient interaction, the previously distributed rollover patients return to the original sitter and are removed from the others.

"No Rollover" is a policy where the remaining patients are not rolled over to anyone. In effect, the other patients that were being monitored simply go unmonitored during the period that their sitter is unavailable for sitter monitoring duties. Obviously, this policy is the least desirable of the rollover policies, but in some cases is necessary. The No Rollover policy is often the result of all other rollover policies failing under the circumstance, such as when multiple sitters are simultaneously interacting with separate single patients.

It should be mentioned that under certain circumstances, especially under Wi-Fi Proximity and GPS rollover policies, a sitter may be required to reposition to better serve the patients being monitored. In other situations, one or more of a sitter's patients may be reassigned to other sitters in order to effectively implement the rollover policies and balance the sitter's loads with patient's closest to the sitter's initial monitoring group.

Figure 6A:
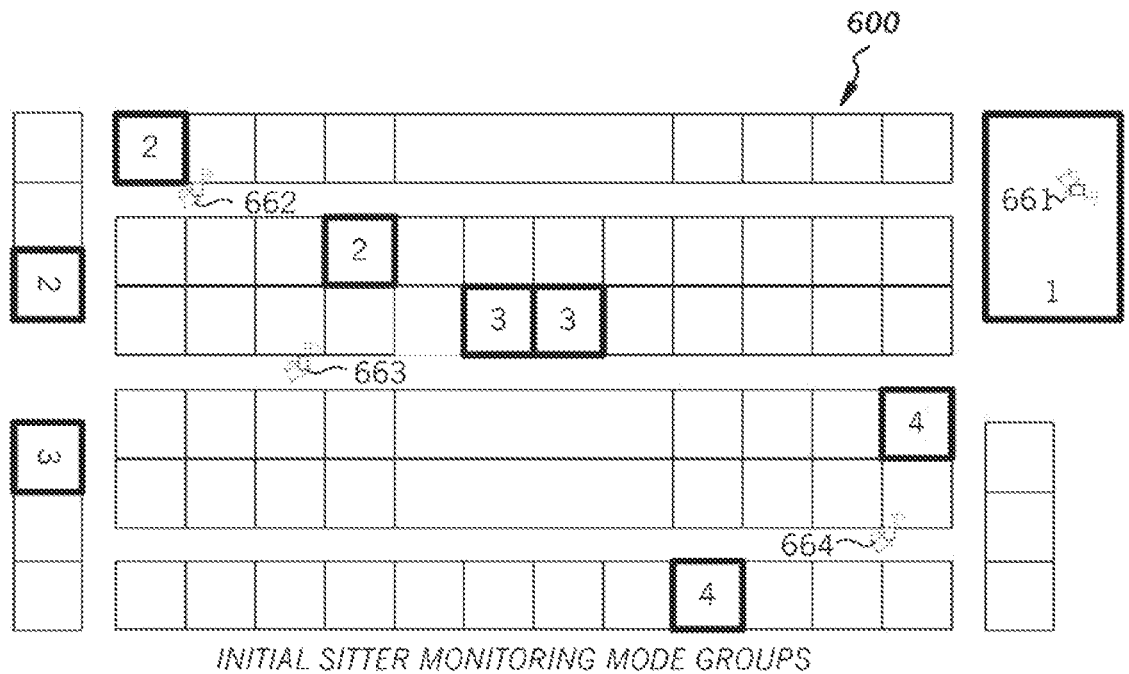
FIGS. 6A and 6B graphically represent the redistribution of patients from one sitter group to another sitter group based on a sitter becoming unavailable in accordance with various exemplary embodiments of the present invention.
Figure 6B:
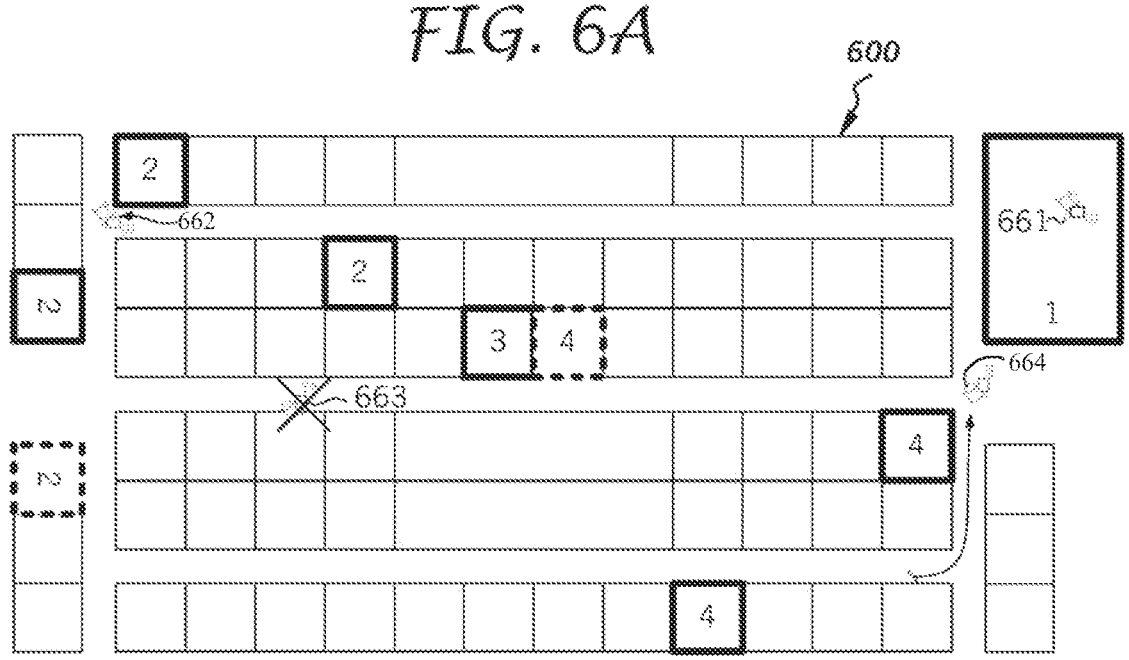

FIGS. 6A and 6B graphically represent the redistribution of patients from one sitter group to another sitter group based on a sitter becoming unavailable, such as when a sitter issues an ATTEND PATIENT command for interacting with a single patient. FIG. 6A shows HCF 600 with the presently described electronic patient sitter management system implementing therein in an initial patient assignment state (or some state), subsequent to patients being assigned to sitters and sitter/patient groups being defined as described above with regard to the flowchart depicted in FIGS. 8A and 8B. HCF 600 is identical to HCF 500 in that four separate sitter managed groups are defined with Group 1 encompassing the patients within ICU and is monitored by sitter device 661, Group 2 being monitored by sitter device 662 that is positioned in the corridor centrally located to the patient rooms of Group 2, likewise, groups 3 and 4. FIG. 6B shows the new patient/sitter groups with sitter device 663 becoming unavailable by providing personal interaction with a single patient (labeled "3"). In response, the presently described electronic patient sitter management system invokes its predetermined rollover policies for the event. Here, HCF 600 shows the resultant patient distribution subsequent to the Equal Distribution rollover policy for redistributing patients equally between sitters 662 and 664 with regard to distance using one of the WI-FI, GPS or Blueprint rollover policies. Notice one patient from Group 3 is assigned to each of Groups 2 and 4, while both sitters 662 and 664 relocate their positions based on some distance criteria.

As a sidebar it should be noted that in some cases, all of a sitter's patients are reassigned to other available sitters, such as when a sitter is determined to be inattentive to the sitter's assigned patients, or when the sitter fails the alertness test. Surveillance can be brutally boring causing the sitter's attention to turn from the monitoring screen. If undetected, the patient may be in jeopardy. In accordance with one exemplary embodiment of the present invention the presently described electronic patient sitter management system detects inattentive sitters by issuing random alertness tests. The alertness test prompts the sitter to respond at random intervals. The test can be as simple as a dialog box prompting the sitter to push a button. If the sitter fails to pass the test, the incident is logged and reported to a remote station. Depending on the severity, frequency and history of the sitter, failing the alertness may cause the electronic patient sitter management system to list the sitter as unavailable, de-authorize the sitter's device and invoke a rollover policy, automatically. Alternately, or in addition, the sitter device may contain a motion and or position sensor that evaluates the position and orientation of the device and logs changes that indicate that the sitter device has been moved. If the device remains stationary over a long period of time, the electronic patient sitter management system may issue an alertness test, or issue tests more frequently. Moreover, the sitter device may also be configured with video (webcam). From that, a sitter manager can monitor real time video from the device. It is not expected that the sitter will also be in the view angle of the camera, but will from time to time, allowing the manager a glimpse of the sitter.

Figure 8A:
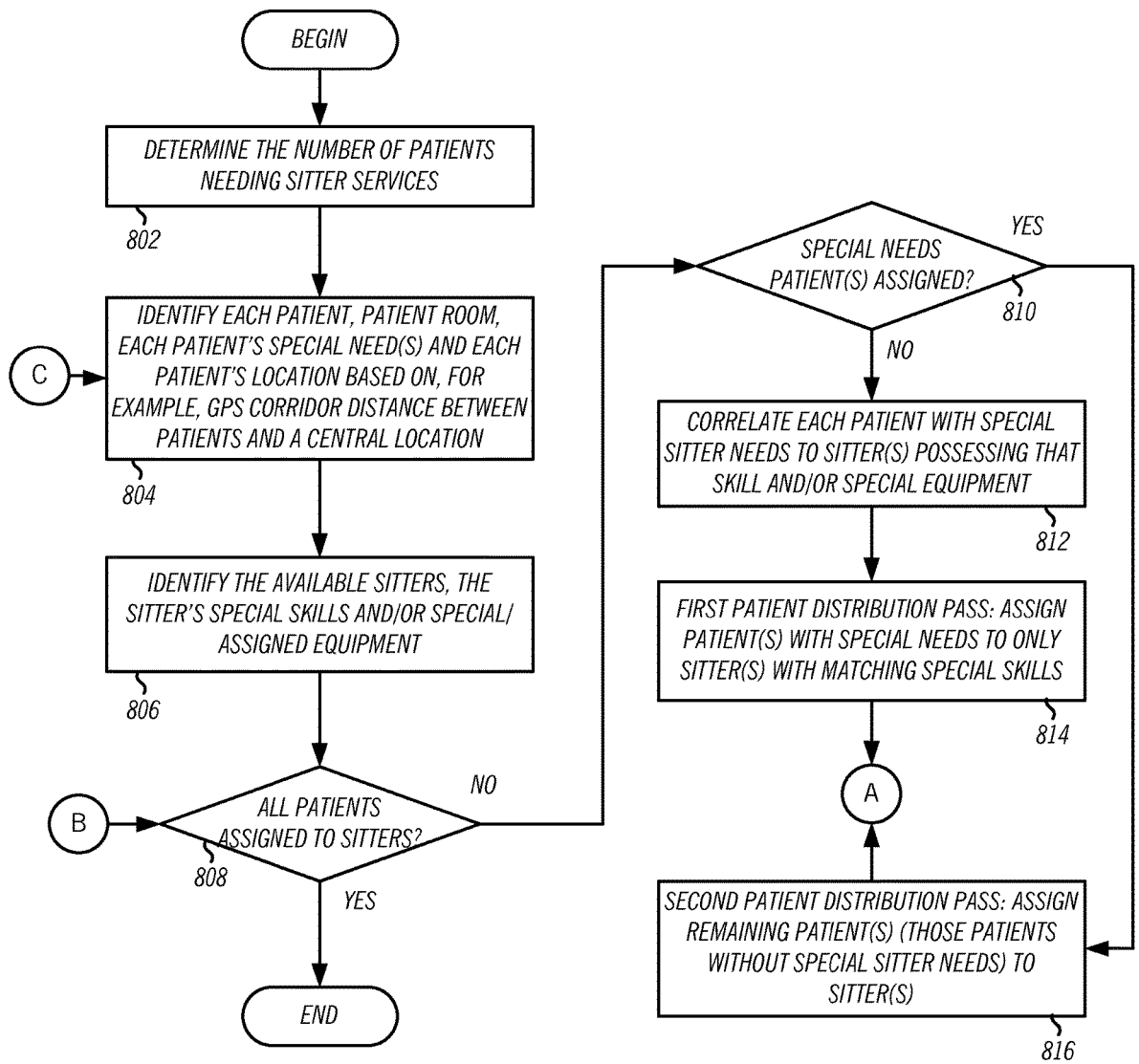
FIGS. 8A and 8B depict a flowchart for a method for setting sitter distributions and sitter assignments within the electronic patient sitter management system in accordance with one exemplary embodiment of the present invention.
Figure 8B:
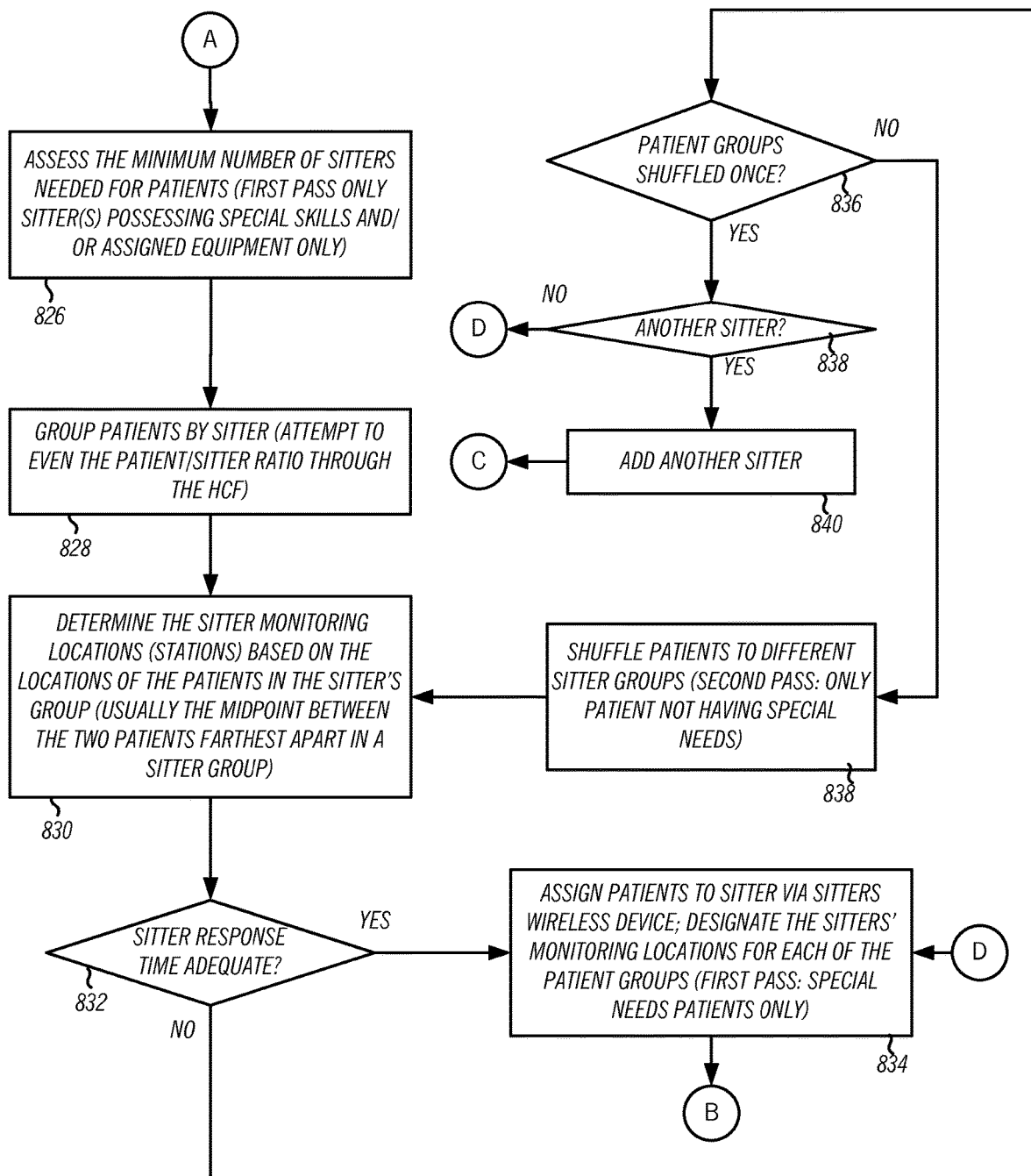

FIGS. 8A, 8B, 9A, 9B, 10A and 10B are flowcharts depicting various methods performed by the presently described electronic patient sitter management system. FIGS. 8A and 8B depict a flowchart for a method for setting sitter distributions and sitter assignments within the electronic patient sitter management system in accordance with one exemplary embodiment of the present invention. As a practical matter, the patients (or patient rooms) are actually assigned to the sitters, however, for ease of describing the present invention, the sitter assignments will be understood as being synonymous to patient sitter assignment or patient assignments. The method of FIGS. 8A and 8B is most often accomplished at shift changes, but may be invoked at anytime. Optimally, this process is automated within sitter management service 352, but might instead be manually executed by a sitter manager, for instance.

The sitter distribution and assignment process begins by assessing the number of patients needing sitter services (step 802) and then proceeds by identifying each patient and locations of the corresponding patient rooms (this is only necessary if one of Wi-Fi Proximity, GPS and/or Blueprint rollover policies will be used, as well as for distributing the sitter stations over the HCF) (step 804). Additionally, if a patient has special sitter needs or sitter requirements, each patient's special sitter needs should also be identified. These special sitter requirements are usually based on some patient welfare criteria, such as those patients requiring a sitter with advanced first aid or CPR training. Alternatively, certain patients may indicate a gender preference for the sitters who are responsible for them. Next, the sitter manager and/or sitter management service 352 identifies the available sitters, each sitter's special skills and training and their gender (step 806). In some HCFs, such as a long term care or rehabilitation facilities, certain sitters may be issued specialized equipment, such as heart defibrillators, vital signs monitors, resuscitators, aspirators or the like. Those sitters and their equipment should also be identified for the distribution and patient assignment process.

Next, the sitters are assigned patients in a two pass sitter distribution and assignment method, the first pass by correlating those patients with special sitter requirements to sitters having those skill or who are assigned specialty equipment for meeting that patient's needs. The second pass is for assigning the sitters to all remaining patients without regard to a sitter's skills or assigned equipment. Optimally, it is expected that the assignment of sitters to patients will be accomplished automatically by sitter management service 352, however, certain patient assignment criteria may be beyond the scope of the sitter management service, requiring the sitter manager to make sitter assignments manually to the patients. Initially, the sitter assignment process tests for unassigned patients (step 808) and then tests for patients with special sitter needs (step 810). If patients with special needs are identified as being unassigned to sitters, each patient with a special need is correlated to a sitter possessing a skill, training, gender or equipment matching that special patient sitter requirement (step 812). Then, sitters with special skills matching the patients' sitter requirements receive patient assignments (step 814) (see FIGS. 9A and 9B below).

Patient sitter assignments is essentially identical for patients having special sitters needs and for those without any special sitter needs, however, it is expected that most patients needing sitter services will usually not have any special sitter requirements. The sitter assignment sub-process is depicted in FIG. 8B and identical for both passes. Initially, the sitter assignment sub-process assesses the number of sitters that should be available for the patient's needing sitter services, the first pass for only those patients with special sitter requirements (step 826). Here, the available sitters have already been identified in step 804 so this step merely confirms to the sitter manager that the sitter staff is adequate to handle the number of patients needing sitter services. Patients are then grouped by sitter, into sitter groups. Optimally, this sitter grouping attempts to keep the patient to sitter ratio approximately equal for all of the available sitters (step 828). Here, it should be mentioned that maintaining patient/sitter ratios is difficult for patients with special sitter requirements because the sitter requirements vary widely between patients as do the sitters' skills and assigned equipment. Additionally, sitters may have designated fixed monitoring stations, such as at a nurse station or the like, or may have floating stations that are determined based on, for example, the locations of the patient's rooms in the sitter's group, i.e., the sitter's assigned patients. In the first instance, patients are grouped to sitters having fixed monitoring stations that are proximately located to the locations of the patients' room. In the second instance, patients may be assigned to a sitter group based on their proximity to each other's room locations (step 830) and only then are the sitters' floating station locations determined within the HCF. In the latter case, the locations of a sitter's floating monitoring station will be determined based on distances between furthest located patient rooms in a group, usually the midpoint between those patient rooms.

Next, the sitter assignment sub-process tests the sitter response times for patient room locations within a sitter's patient group (step 832). The aim is to not only have the sitter/patient ratio between sitters being approximately equivalent, but also the maximum response times for sitters to be equivalent between sitter groups, or at least maintain the response time being below a base response time for each patient. If the sitter response times are adequate, the patients in a group are assigned to the respective sitter groups, or more particularly to a sitter's wireless sitter device 360 for that sitter group, and each sitter is designated a location for establishing a patient monitoring station from which to monitor patients (step 834). The sitter sub-process then reverts to the test for unassigned patients at step 808.

If, however, at step 832, the sitter response time for one or all of the patients is not adequate between the sitter groups, the sitter assignment sub-process attempts to correct this deficiency by redistributing the sitters to the patients, thus forming new sitter groups, ideally with adequate sitter response times. The sitter groups are shuffled (usually only once (step 836)) to find a better combination of sitter and patients within the sitter groups (step 838) and the sitter assignment sub-process reverts to step 830 for determining location the sitter monitoring stations (assuming the stations have floating, and not fixed patient monitoring locations) and again tests the sitter response times for adequacy (step 832). If the response times are adequate, the sitter sub-process then reverts to testing for unassigned patients at step 808, if the response times are not, the process moves to the shuffle count test at step 836. If the maximum number of sitter shuffles have already occurred, then the process inquires as to the availability of one or more additional sitters (step 838). If another sitter can be identified, that sitter is added to the sitter distribution and assignment process (step 840) and the process then reverts to step 804 where all sitters and their special skills, assigned equipment and gender are identified. If an additional sitter is added for the first pass of the sitter distribution and assignment process, that sitter should have the skills or training necessary needed to satisfy steps 812 and 814 of the process (merely adding a sitter without any skills/training matching the patients' requirements will not alter the outcome of the sitter response time test in step 832. The process then continues as describe above, hopefully with adequate sitter response times. If, however, at step 838, no other sitters can be identified for assignments, then the sitter assignment sub-process proceeds to step 834 where each of the sitters are assigned patients (to wireless sitter devices 360) regardless of sitter response adequacy, and each sitter is designated a patient monitoring stations from which to monitor patients (if necessary). In the last case, the HCF must compromise its established adequacy goals for sitter response times.

Once all sitters with special skill, training or equipment are assigned to patients having matching sitter requirements, then the process reverts to the sitter assignment test for unassigned patients at step 808. At this point, only patients without special sitters needs are not assigned to sitters (steps 808, 810 and 816), however all sitters, even those with special training, skills and assigned equipment, and regardless of gender, are consider for additional sitter assignments of patients. In the second pass of the sitter assignment sub-process, the number of sitters that are needed for sitter services in, for example, the HCF, is determined for any remaining patients that are not assigned to sitter (those patients without special sitter requirements) (step 826). Patients are again grouped by sitter with an attempt to keep the patient to sitter ratio approximately equal for all of the sitter groups (step 828). Because some of the sitters have already been assigned patients (those with special sitter requirements), sitters not having special skills, training or assigned equipment will receive most of the new patient assignments.

Next, the locations of the sitters' monitoring stations are determined (step 830), sitter response times tested for adequacy (step 832) and the sitter assigned patients based on a positive outcome of the response time test (step 834). The process then reverts to the sitter assignment test at step 808 and ends.

If, at step 832, the sitter response time for the patients is not adequate, the patient assignment tests for previous sitter group shuffling (step 836), shuffles the sitter groups if possible and again determines the sitter monitoring locations (step 830) and tests for response times for adequacy (step 832). Here, if the response times are adequate, the sitter sub-process then reverts to the test for unassigned patients at step 808, and the process ends as all patients are assigned to sitters.

If, at step 832 the sitter response times are not adequate, the process moves to inquire for another sitter to be added. If an additional sitter is available and can be added (step 840), the process reverts to step 804 where all sitters are identified and the process continues as described above with the additional sitter. If no other sitters are available, then the sitter assignment sub-process proceeds to step 834 where each of the patients are assigned to the sitters (to wireless sitter devices 360) regardless of response adequacy, and each sitter is designated a location for a patient monitoring station from which to monitor patients (if necessary). The process then tests for unassigned patients needing sitter services (step 808), and ends as all patients, those with special sitter requirements and those without any special sitter requirements, are all assigned to appropriate sitters.

FIGS. 9A and 9B is a flowchart of a method performed by the electronic patient sitter management system arbitrating between standard run mode and rollover conditions in accordance with one exemplary embodiment of the present invention. As mentioned above, the presently described electronic patient sitter management system is superior to the prior art local sitter paradigm, among other reasons, because the system can adjust by reassigning patients between sitters for available sitters. While at first blush, rollover events may seem to be random and infrequent, actually, the electronic patient sitter management system is predicated on rolling over patients from one sitter to others. Ensuring that the system acquires the correct mode is paramount.

The process begins by defining initial sitter groups based on the number of patients needing sitter services and the special sitter requirements of some of those patients (step 902). Next, sitter groups are defined for the HCF based on those groups for monitoring patients' rooms (step 904). The rollover policy(ies) that the HCF intends to invoke is selected from those discussed above, or a hybrid rollover policy, or primary and secondary policies to be conditionally invoked (step 908). Exemplary rollover policies are discussed above. Next, the sitters are authorized on electronic patient sitter management system and the sitter devices enabled (step 906). Patient sitters assignments, structuring sitter groups and authorizing sitters and their devices are described above with regard to the flowchart depicting in FIGS. 8A and 8B and with regard to block 710 in FIG. 7A. The steps described above are typically performed while the electronic patient sitter management system is in set up mode, however at this point the electronic patient sitter management system transitions into run or monitoring operation mode.

Once the rollover policy(ies) are identified for the HCF, the system proceeds into an infinite loop of testing for unavailable sitters and invoking temporary rollover assignments based on the outcome of that test. At each iteration, the process verifies that all authenticated sitters that were available for performing their sitter monitoring duties in the previous iteration are still available in the current iteration (step 910). As discussed elsewhere above, a sitter may become unavailable to one or all of his assigned patients for a variety of reasons: the sitter is attending an individual patient and is unavailable to the remaining assigned patients; the sitter is on break and is unavailable to all of his assigned patients; the sitter fails an alertness test and is unavailable to all of his assigned patients, etc. If, at step 910, a previously available sitter becomes unavailable, the process flows directly to step 920 for invoking a rollover policy. Invocation of rollover assignment policy(ies) is described below in FIG. 9B.

Returning to step 910, assuming all sitters that were available in the previous iteration are currently available, the system checks for rollover policies that might currently be in effect for the current iteration (step 912). Here it should be apparent that in any iteration, the electronic patient sitter management system may or may not be currently operating in a rollover mode with the associated rollover policies in effect. If a rollover policy is not currently invoked in this iteration, the process tests for a new rollover condition (step 916). Briefly returning to step 912, if a rollover policy is in effect, the process flows to step 914 where the system tests for rollover conditions that precipitated the policy, that is, if the previously unavailable sitter remains unavailable. If the condition has not abated, the process continues to step 916 and the process tests for a new rollover condition, that is, if all previously available sitters remain available. Here, the rollover process iterates between steps 912, 914 and 916, testing for a rollover policy, testing for the previously unavailable sitters becoming available and vice versa. i.e., testing for rollover conditions that caused the current rollover policy to be invoked and testing for any new rollover conditions that might have been detected this iteration.

The process continues iterating between steps 912, 914 and 916 unless one of two events are detected, a previously unavailable sitter becoming available in step 914 or a previously available sitter becomes unavailable at step 916. When a previously unavailable sitter becomes available, that is the rollover condition abates (step 914), the process rescinds the current rollover policy (step 918) and returns to step 908 where the returning sitter and sitter device is enabled/authorized and the rollover tests continue at step 912. If, on the other hand, a previously available becomes unavailable, that is a new rollover condition is detected, the process invokes a rollover policy (step 920).

Turning to FIG. 9B rollover sitter assignment is a two pass sub-process that essentially mirrors the sitter assignments passes described above in FIGS. 8A and 8B for patients having special sitter requirements and patient without any special sitter needs. The rollover process begins with the process to gather information concerning the rollover condition from either of steps 910 or 916 (step 952). A rollover condition might involve the system receiving sitter "attend patient" request command for the sitter designating an assigned patient to receive individual attention, or sitter logout request command indicating that a sitter will be unavailable to monitor any of the sitter's assigned patients, the system may receive an indication that a sitter failed an alertness test failure, also indicating that the sitter unavailable for monitoring any of the sitter's assigned patients.

With that information, the process identifies all patients that are unmonitored in the current iteration of the process (step 954). Those patients are then deleted from the sitter's assigned patients (assuming the sitter remains available for at least one assigned patient (step 956).

Next, the process flows into the two passes for temporarily rollover assigning patients that have special sitter requirements, and for those patients not having special sitter requirements, beginning with a test for patients having special sitter requirements (step 958). Assuming such patients are being unmonitored, the process identifies those unmonitored patients, along with their special sitter requirements (step 968). Next, the process identifies any available sitters with special skills, training or assigned equipment matching the patients' special sitter requirements (step 970).

Here it should be understood that sitter assignment matching for patients having special sitter needs may not always be completely successful, especially in the case of a sitter having special skill/training/equipment becoming unavailable. In some cases, no sitter match is present and the patient with special sitter needs remains unassigned in the first pass. Optimally, a patient is rollover assigned to an available sitter having a matching skill/training/equipment, if one exists, but if more than one exists, the process invokes the rollover policies to determine which sitter to assign. Although the flowchart is not clear in this area, the sitters having special skill/training/equipment are matched to patients have matching sitter requirements in a parallel process flow, one parallel pipe for each unique special sitter requirement. Some parallel requirement-skill/training/equipment pipes might have one patient and several sitters correlating to a match, other requirement-skill/training/equipment pipes may have only one sitter and several patients, while still other requirement-skill/training/equipment may have only a single sitter and a single patient. The process handles these parallel operations for each patient sitter requirement by determining the number of sitters having a special skill/training/equipment matching the sitter requirement (step 972) and then calling up the rollover policy(ies) designated in step 906 for the case where more than a single sitter matches (step 964) and then assigns the patient(s) with special sitter requirements to a plurality of available sitters having matching special skill/training/equipment based on the rollover policy(ies) (step 966). If at step 972, only a single available sitter exists, the process assigns the patient with special sitter requirements to the only available sitter having matching special skill/training/equipment (step 966). Next, the process tests for any unassigned and unmonitored patients in the current pass (step 968). Recall here that some patients with special sitter needs may not be matched to sitters having a corresponding special skill/training/equipment and so those patients are rollover assigned in the second pass for the remainder (if any) of the unassigned and unmonitored patients.

The process returns to step 960 for identifying any available sitter(s) in this iteration of the process. It should be appreciated that the available sitter(s) may be one or any available sitter(s) without any special skill/training/equipment, and/or available sitter(s) having special skill/training/equipment but no temporary rollover assigned patients from the first pass, and/or available sitter(s) having special skill/training/equipment with one or more temporary rollover assigned patient(s) from the first pass. In this pass, the designation of an available sitter having special skill/training/equipment is not considered. As in the first pass, if at step 962, only a single available sitter exists, the unmonitored patient(s) are assigned to that available sitter for monitoring (step 966). Alternatively, if more than one sitter is currently available at step 962, then the process retrieves the proper designated rollover policy(ies) for the rollover condition (step 964) and assigns the patients to the sitters based on that designated rollover policy(ies) (step 966). The process then makes a final test for unmonitored patients in this iteration of the process, subsequent to the second pass there should be no unmonitored patients, and the process returns to step 922. The process essentially continues running in the background until, for instance, the sitters' work shift end, the sitters log out en masse and the presently described electronic patient sitter management system authorizes new sitter under the process of FIGS. 8A and 8B.

Figure 10B:
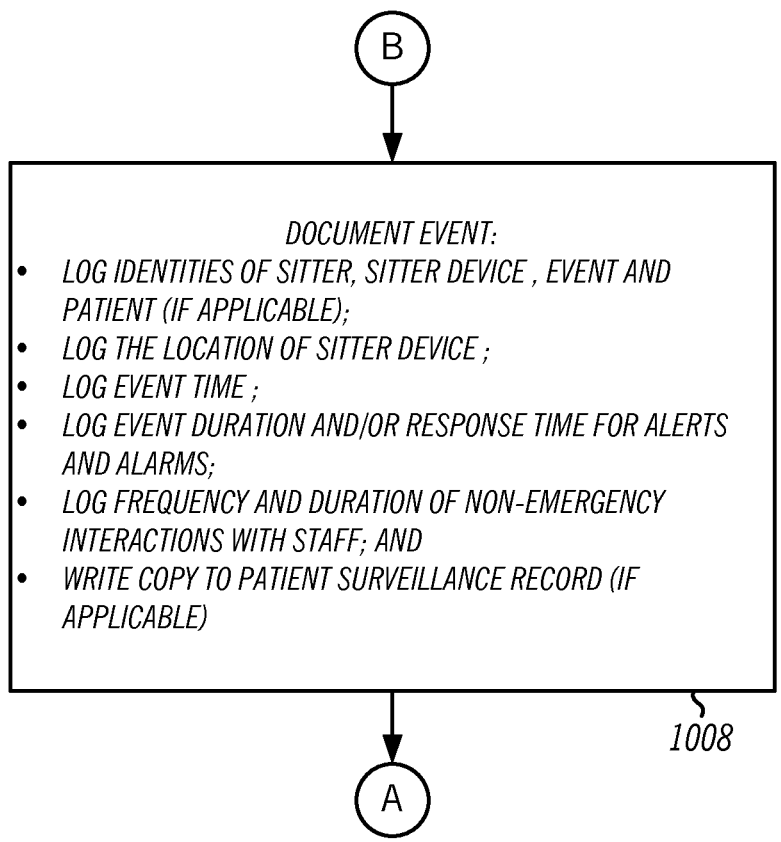
Figure 11:
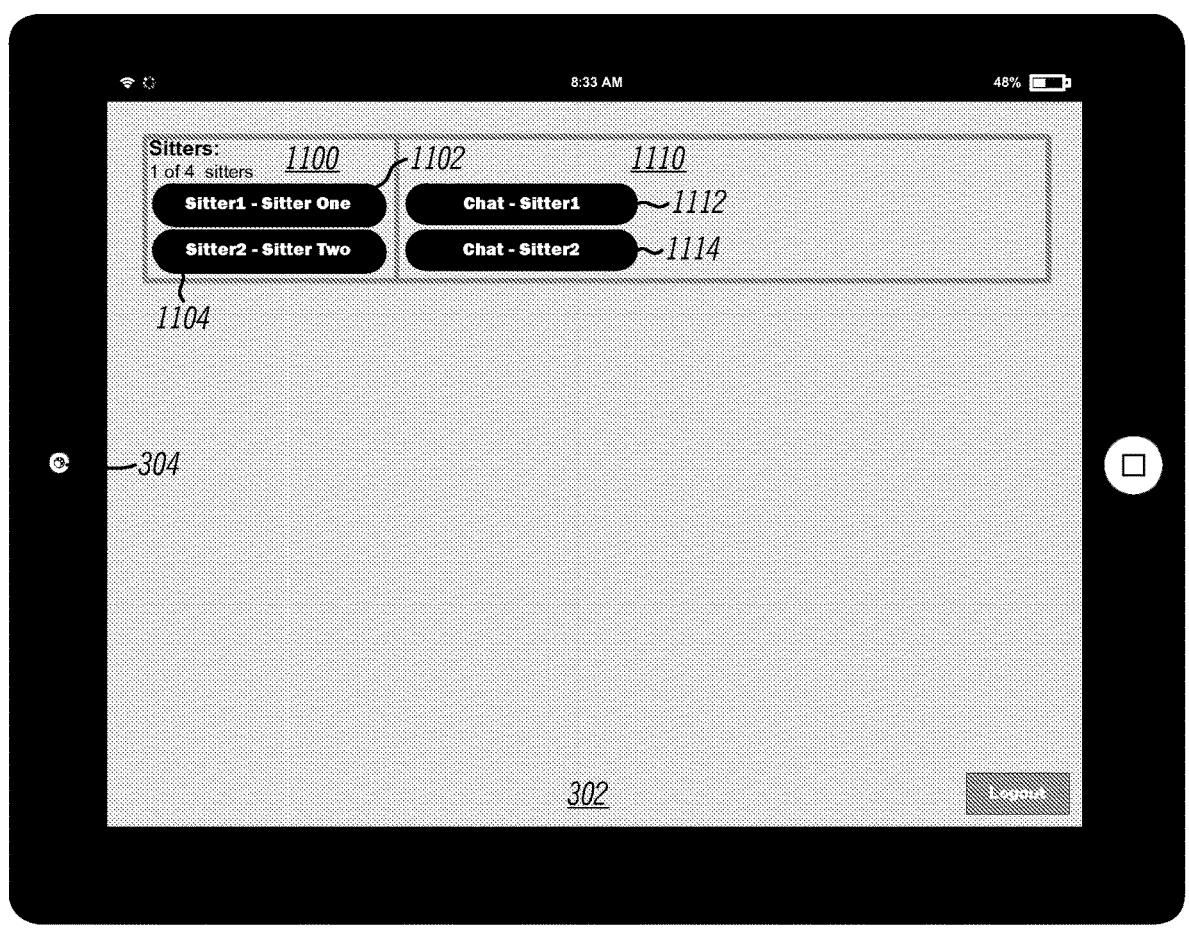
FIG. 11 is a diagram of a sitter manager patient assignment screen as presented on a sitter manager device in accordance with an exemplary embodiment of the present invention.
Figure 12:
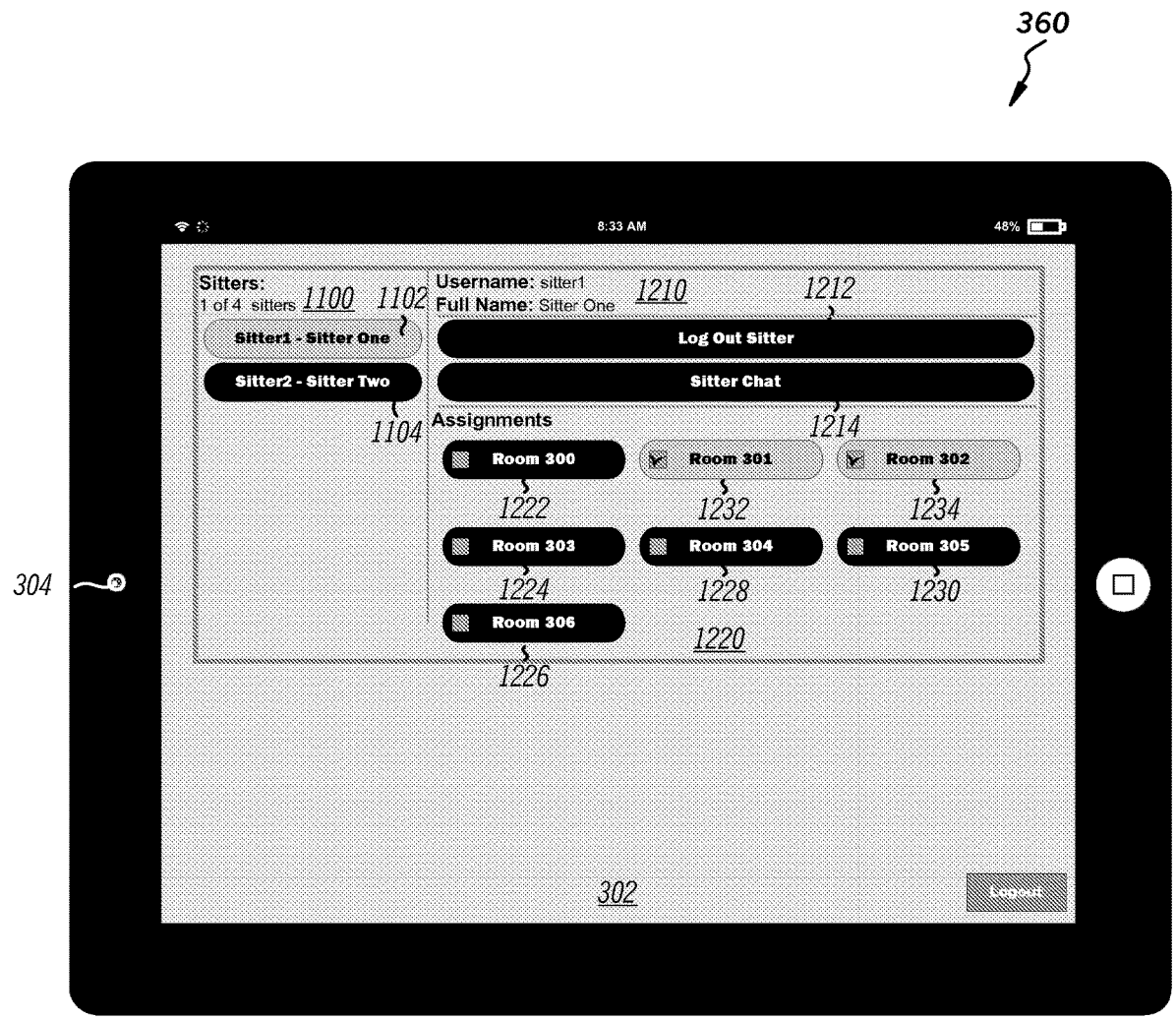
FIG. 12 is a diagram of a sitter manager patient assignment screen showing patient assignments to specifically identified sitters in accordance with an exemplary embodiment of the present invention.

FIGS. 10A and 10B depict a flowchart of method performed by the electronic patient sitter management system for logging events and issuing alerts and rollover policy in accordance with exemplary embodiments of the present invention. Before proceeding with the description of the method, the presently described electronic patient sitter management system documents log events differently depending on the type of event. Essentially, the sitter system logs identities of sitter, the sitter device, the event type, the time the event occurred and patient (if the event is patient driven), regardless of the type of event. Additionally, the system logs the event duration and/or sitter response time for alerts and alarms. Optionally, the system may log the location of sitter device, if the location information is known. In accordance with some exemplary embodiments of the present invention, the system will log frequency and duration of non-emergency interactions between the sitter and staff, mostly for quality assurance of the sitter's capabilities (see for instance sitter activity log 1430 on FIG. 14). Finally, in situations where the event might be important for the patient's medical records, or in cases where some aspect of the event might need further review, the system may save the event with the surveillance video data for the patient and/or to the patient's records.

The present process is iterative and continuous, regardless of the operational mode, i.e., set up, RUN, patient monitoring, in or out of rollover, etc. While the steps below are described as "checks," more pragmatically the system merely resides in a WAIT state for the occurrence of an event and then determines the applicability of logging the event based on the method criteria below. One test, perhaps a forerunner test, is for sitter log ins or log outs (step 1002). If a sitter logs in, the process goes to step 1008 where the log in event is logged. If, on the other hand, a sitter log out is detected, that sitter becomes unavailable for monitoring and a rollover policy is invoked (step 1016). The process reverts to step 1008 where the event is logged.

Subsequent to logging, the system may perform an optional movement test (step 1004) and if the sitter device is moving or has moved, the system determines if the device has been moved out of the sitter's designated monitoring area (step 1004). If so, the system issues an alert to, for example, the sitter manager, apprising her of the movement (step 1006). The process reverts to step 1008 where the movement event is logged. If the sitter device has not moved (step 1004) or has not moved outside the sitter monitor area (step 1010), the process checks for the occurrence sitter alert tests (step 1012). If an alert test has occurred and the sitter responds appropriately (passes the test), the test event is logged (step 1008) and the process reverts to, for example, step 1002 and continues.

If, on the other hand, the sitter fails the alertness test, the system may take one of two responses. First, the system might merely issue an alert to the sitter manager (step 1006) and log the test failure (step 1008). Alternatively, the system may instead treat the sitter as being unavailable for monitoring and invoke the appropriate rollover policy (step 1016). In that case, the system logs both the test failure and the rollover event (step 1008). Ideally, the system should not immediately treat the sitter as being unavailable unless some factors other than a single alertness test failure are present, e.g., the sitter manager set the rollover parameters, the sitter failed multiple successive alertness tests, etc.

Next, if the system receives information from a sitter device that the sitter is interacting with a single patient, and hence unavailable for monitoring the sitter's remaining patients, the system invokes the rollover policy (step 1016) and then logs receiving of the patient interaction information and the rollover event itself (step 1008). Receiving information that a sitter has invoked some other rollover policy is handled similarly to single patient interaction events. The system invokes the specified rollover policy (step 1016) and then logs both the receiving event and the rollover event (step 1008). Finally, most, if not all, sitter interactions with the sitter device are logged (step 1008) and the process iterates to step 1002.

As will be appreciated by one of skill in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects all generally referred to herein as a "circuit" or "module." Furthermore, the present invention may take the form of a computer program product on a computer-usable storage medium having computer-usable program code embodied in the medium.

Any suitable computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the in the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Moreover, the computer readable medium may include a carrier wave or a carrier signal as may be transmitted by a computer server including internets, extranets, intranets, world wide web, ftp location or other service that may broadcast, unicast or otherwise communicate an embodiment of the present invention. The various embodiments of the present invention may be stored together or distributed, either spatially or temporally across one or more devices.

The exemplary embodiments described below were selected and described in order to best explain the principles of the invention and the practical application, and to enable others of ordinary skill in the art to understand the invention for various embodiments with various modifications as are suited to the particular use contemplated. The particular embodiments described below are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A method for managing patient surveillance video in an electronic sitter system for monitoring patients, the method comprising:
receiving, at a first sitter device, a plurality of real-time patient surveillance video streams from cameras located in a plurality of patient rooms;
simultaneously displaying the plurality of real-time patient surveillance video streams at the first sitter device including a given real-time patient surveillance video stream of the plurality of real-time patient surveillance video streams;
detecting, by a motion detector device, motions within the given real-time patient surveillance video stream;
discriminating, by the motion detector device, patient motion from the detected motions;
receiving, at the first sitter device, an alert corresponding to the patient motion, wherein the alert is received subsequent to the first sitter device receiving and displaying the given real-time patient surveillance video stream; and
providing at the first sitter device a patient video zoom function that corresponds to the given real-time patient surveillance video stream.

2. The method of claim 1 wherein the patient video zoom function comprises a zoom in view of a patient in the given real-time patient surveillance video stream.

3. The method of claim 1 further comprising receiving at the first sitter device a selection of the given real-time patient surveillance video stream,
wherein providing the patient video zoom function comprises presenting, at the first sitter device, based at least in part on the receipt of the selection of the given real-time patient surveillance video stream, a separate enhanced surveillance video frame for the given real-time patient surveillance video stream, the enhanced surveillance video frame comprising the patient video zoom function.

4. The method of claim 3 further comprising viewing a patient at the first sitter device using the patient video zoom function on the enhanced surveillance video frame.

5. The method of claim 1 further comprising providing at least one interactive control for at least the given patient room that corresponds to the given real-time patient surveillance video stream, the at least one interactive control including a patient chat function between the first sitter device and the given patient room.

6. The method of claim 1 wherein the alert includes an indication that emphasizes a room surveillance frame corresponding to the given patient room.

7. The method of claim 1 further comprising predicting a patient fall based on the patient motion.

8. The method of claim 1 further comprising logging events or actions of a patient corresponding to the given patient room.

9. The method of claim 1 further comprising displaying patient information including at least a patient name and medical information.

10. An electronic sitter system coupled to a patient surveillance network, the patient surveillance network comprising a plurality of video cameras for capturing and transmitting surveillance video streams and a plurality of sensors for capturing data in patient rooms, each of the plurality of video cameras located in a patient room and aimed at an interior of the respective patient room, the electronic sitter system comprising:
a plurality of sitter devices, each sitter device configured to:
receive a plurality of patient surveillance video streams from cameras located in a plurality of patient rooms;
simultaneously display the plurality of real-time patient surveillance video streams including a given real-time patient surveillance video stream of the plurality of real-time patient surveillance video streams;
receive an alert corresponding to patient motion, the patient motion discriminated from motions detected within the given real-time patient surveillance video stream, wherein the alert is received subsequent to the sitter device receiving and displaying the given real-time patient surveillance video stream; and
provide a patient video zoom function that corresponds to the given real-time patient surveillance video stream.

11. The system of claim 10 wherein the patient video zoom function comprises a zoom in view of a patient in the given real-time patient surveillance video stream.

12. The system of claim 10 further comprising the sitter device configured to receive a selection of the given real-time patient surveillance video stream; and wherein providing the patient video zoom function comprises presenting, based at least in part on the receipt of the selection of the given real-time patient surveillance video stream, a separate enhanced surveillance video frame for the given real-time patient surveillance video stream, the enhanced surveillance video frame comprising the patient video zoom function.

13. The system of claim 12 further comprising the sitter device configured to view a patient using the patient video zoom function on the enhanced surveillance video frame.

14. The system of claim 10 further comprising the sitter device configured to provide at least one interactive control for at least the given patient room that corresponds to the given real-time patient surveillance video stream, the at least one interactive control including a patient chat function between the sitter device and the given patient room.

15. The system of claim 10 further comprising the sitter device configured to predict a patient fall based on the patient motion.

16. The system of claim 10 further comprising the sitter device configured to log events or actions of a patient corresponding to the given patient room.

17. The system of claim 10 further comprising the sitter device configured to display patient information including at least a patient name and medical information.

18. Non-transitory computer-readable media comprising program code that when executed by a programmable processor causes execution of a method for managing patient surveillance video in an electronic sitter system for monitoring patients, the computer-readable media comprising:

- computer program code for receiving a plurality of real-time patient surveillance video streams from cameras located in a plurality of patient rooms;
- computer program code for simultaneously displaying the plurality of real-time patient surveillance video streams including a given real-time patient surveillance video stream of the plurality of real-time patient surveillance video streams;
- computer program code for detecting motions within the given real-time patient surveillance video stream;
- computer program code for discriminating patient motion from the detected motions;
- computer program code for receiving an alert corresponding to the patient motion, wherein the alert is received subsequent to receiving and displaying the given real-time patient surveillance video stream; and
- computer program code for providing a patient video zoom function that corresponds to the given real-time patient surveillance video stream.

19. The non-transitory computer-readable media of claim 18 wherein the patient video zoom function comprises a zoom in view of a patient in the given real-time patient surveillance video stream.

20. The non-transitory computer-readable media of claim 18 further comprising computer program code for receiving a selection of the given real-time patient surveillance video stream, wherein providing the patient video zoom function comprises presenting, based at least in part on the receipt of the selection of the given real-time patient surveillance video stream, a separate enhanced surveillance video frame for the given real-time patient surveillance video stream, the enhanced surveillance video frame comprising the patient video zoom function.

* * * * *